(12) United States Patent
Hosoya et al.

(10) Patent No.: US 8,431,525 B2
(45) Date of Patent: Apr. 30, 2013

(54) COELENTERAMIDE ANALOGS

(75) Inventors: Takamitsu Hosoya, Tokyo (JP); Kohei Oka, Tokyo (JP); Satoshi Inouye, Yokohama (JP)

(73) Assignees: JNC Corporation, Tokyo (JP); Tokyo Institute of Technology, Tokyo (JP)

( * ) Notice: Subject to any disclaimer, the term of this patent is extended or adjusted under 35 U.S.C. 154(b) by 27 days.

(21) Appl. No.: 13/146,710

(22) PCT Filed: Feb. 8, 2010

(86) PCT No.: PCT/JP2010/051806
§ 371 (c)(1),
(2), (4) Date: Jul. 28, 2011

(87) PCT Pub. No.: WO2010/090318
PCT Pub. Date: Aug. 12, 2010

(65) Prior Publication Data
US 2011/0288280 A1    Nov. 24, 2011

(30) Foreign Application Priority Data
Feb. 9, 2009    (JP) .................... 2009-027904

(51) Int. Cl.
*A61K 38/00* (2006.01)
*C07K 1/00* (2006.01)
*C07K 14/00* (2006.01)
*C07K 16/00* (2006.01)
*C07K 17/00* (2006.01)
*C08H 1/00* (2006.01)

(52) U.S. Cl.
USPC .......................... 514/1.1; 530/408; 530/409

(58) Field of Classification Search .................. None
See application file for complete search history.

(56) References Cited

U.S. PATENT DOCUMENTS

| 7,396,655 | B2 * | 7/2008 | Inouye et al. ................ 435/8 |
| 2006/0234324 | A1 | 10/2006 | Inouye et al. |
| 2011/0070656 | A1 * | 3/2011 | Inouye ......................... 436/501 |

FOREIGN PATENT DOCUMENTS

| EP | 1 666 488 A 1 | | 6/2006 |
| JP | 2006-271327 | | 10/2006 |
| WO | 2005/014633 A 1 | | 2/2005 |
| WO | WO 2005/014633 | * | 2/2005 |

OTHER PUBLICATIONS

International Search Report mailed Mar. 16, 2010 in PCT/JP2010/051806 filed Feb. 8, 2010.
J.F. Head et al., "The crystal structure of the photoprotein aequorin 2.3 Å resolution", Nature, vol. 405, pp. 372-376, May 2000.
S. Inouye, "Blue fluorescent protein from the calcium-sensitive photoprotein aequorin is a heat resistant enzyme, catalyzing the oxidation of coelenterazine", FEBS Letters 577, pp. 105-110, Oct. 2004.
Inouye et al., "Blue fluorescent protein from the calcium-sensitive photoprotein aequorin: Catalytic properties for the oxidation of coelenterazine as an oxygenase", FEBS Letters 580, pp. 1977-1982, Mar. 2006.
O. Shimomura et al., "Chemical nature of the light emitter in bioluminescence of aequorin", Tetrahedron Letters, No. 31, pp. 2963-2966, Mar. 1973.
K. Hori et al., "Identification of the Product Excited States During the Chemiluminescent and Bioluminescent Oxidation of *Renilla* (Sea Pansy) Luciferin and Certain of Its Analogs", Biochemistry, vol. 12, No. 22, pp. 4463-4468, 1973.
F. McCapra et al., "Bioluminescence of Coelenterates: Chemiluminescent Model Compounds", J.C.S. Chem. Comm., pp. 467-468, 1973.
K. Hori et al., "Chemiluminescence of *Renilla* (Sea Pansy) Luciferin and its Analogues", J.C.S. Chem. Comm., pp. 492-493, 1973.
K. Teranishi et al., "Synthesis and Chemiluminescence of Coelenterazine (*Oplophoris* Luciferin) Analogues[1]", Bull Chem. Soc. Jpn., vol. 63, No. 11, pp. 3132-3140, Jun. 1990.
Hirano et al., "Chemiluminescence of Coelenterazine Analogues—Structures of Emitting Species", Tetrahedron Letters, vol. 33, No. 39, pp. 5771-5774, 1992.
K. Teranishi et al., "Synthesis of Hydroperoxide Via Photooxygenation for a Model Aequorin Bioluminescence", Tetrahedron Letters, vol. 35, No. 44, pp. 8181-8184, 1994.
F.Q. Chen et al., "A potential photoaffinity probe for labelling the active site of aequorin: a photolabile coelenterazine analogue with a trifluoromethyldiazirine group", J. Chem. Soc., Perkin Trans.1, pp. 2129-2134, 1995.

(Continued)

*Primary Examiner* — Cecilia J Tsang
*Assistant Examiner* — Sergio Coffa
(74) *Attorney, Agent, or Firm* — Drinker Biddle & Reath LLP

(57) ABSTRACT

There has been a need for coelenteramide analogs or the like that produce fluorescent proteins which exhibit different fluorescent characteristics from those of the existing fluorescent proteins. Disclosed is a compound represented by general formula (1) (wherein $R^1$ represents a substituted or unsubstituted aryl, a substituted or unsubstituted arylalkyl, a straight or branched alkyl which may optionally be substituted with an alicyclic group, an alicyclic group or a heterocyclic group; $R^2$ represents hydrogen or —$(SO_2)R^4$; $R^3$ represents hydrogen, hydroxyl, methoxy or acetoxy; $R^4$ represents a substituted or unsubstituted aryl, a substituted or unsubstituted arylalkyl or a straight or branched alkyl which may optionally be substituted with an alicyclic group; and $X^1$ represents —C(=S)— or —$SO_2$—).

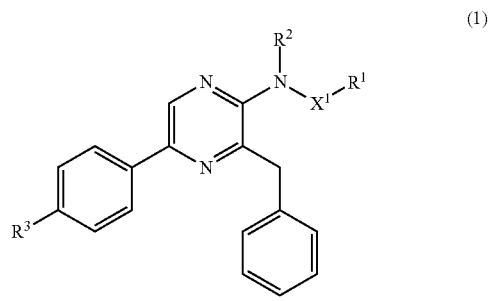

(1)

12 Claims, 4 Drawing Sheets

OTHER PUBLICATIONS

R. Saito et al., "Solvent and substituent effects on the fluorescent properties of coelenteramide analogues", J. Chem. Soc., Perkin Trans. 2, pp. 1711-1716, 1997.

K. Teranishi et al., "Synthesis and Chemiluminescent Properties of the Peroxy Acid Compound as an Intermediate of Coelenterate Luciferin Luminescence", Tetrahedron Letters, vol. 38, No. 15, pp. 2689-2692, 1997.

T. Hirano et al., "Bioluminescent Properties of Fluorinated Semi-synthetic Aequorins", Tetrahedron Letters 39, pp. 5541-5544, May 1998.

J.L. Zheng et al., "Synthesis, Chemi- and Bioluminescence Properties, and Photolysis of a Coelenterazine Analogue Having Photoreactive Azido Group", Bull. Chem. Soc. Jpn., 73, pp. 465-469, 2000.

O. Shimomura et al., "Light-emitters involved in the luminescence of coelenterazine", Luminescence, 15, pp. 51-58, 2000.

K. Teranishi, "Effect of conformation on the chemiluminescence efficiency of light-producing 2-methyl-6-(4-methoxyphenyl)imidazo[1,2-$\alpha$]pyrazin-3(7$H$)-ones", Luminescence 16, pp. 367-374, 2001.

Y. Imai et al., "Fluorescence properties of phenolate anions of coelenteramide analogues: the light-emitter structure in aequorin bioluminescence", Journal of Photochemistry and Photobiology A: Chemistry 146, pp. 95-107, 2001.

Kuse et al., "Novel synthetic route of aryl-aminopyrazine", Tetrahedron, 60, pp. 835-840, 2004.

Kondo et al., "Novel Synthetic Route of Coelenterazines -2-: Synthesis of Various Dehydrocoelenterazine Analogs", Heterocycles, vol. 65, No. 4, pp. 843-856, Feb. 2005.

K. Mori et al., "Real light emitter in the bioluminescence of the calcium-activated photoproteins aequorin and obelin: light emission from the singlet-excited state of coelenteramide phenolate anion in a contact ion pair", Tetrahedron, 62, pp. 6272-6288, May 2006.

* cited by examiner

SEQUENCE LISTING

```
<160> NUMBER OF SEQ ID NOS: 12

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)

<400> SEQUENCE: 1 atg aca agc aaa caa tac tca gtc aag ctt aca tca gac ttc gac aac      48
Met Thr Ser Lys Gln Tyr Ser Val Lys Leu Thr Ser Asp Phe Asp Asn
1               5                   10                  15 cca aga tgg att gga cga cac aag cat atg ttc aat ttc ctt gat gtc      96
Pro Arg Trp Ile Gly Arg His Lys His Met Phe Asn Phe Leu Asp Val
            20                  25                  30 aac cac aat gga aaa atc tct ctt gac gag atg gtc tac aag gca tct     144
Asn His Asn Gly Lys Ile Ser Leu Asp Glu Met Val Tyr Lys Ala Ser
        35                  40                  45 gat att gtc atc aat aac ctt gga gca aca cct gag caa gcc aaa cga     192
Asp Ile Val Ile Asn Asn Leu Gly Ala Thr Pro Glu Gln Ala Lys Arg
    50                  55                  60 cac aaa gat gct gta gaa gcc ttc ttc gga gga gct gga atg aaa tat     240
His Lys Asp Ala Val Glu Ala Phe Phe Gly Gly Ala Gly Met Lys Tyr
65                  70                  75                  80 ggt gtg gaa act gat tgg cct gca tat att gaa gga tgg aaa aaa ttg     288
Gly Val Glu Thr Asp Trp Pro Ala Tyr Ile Glu Gly Trp Lys Lys Leu
                85                  90                  95 gct act gat gaa ttg gag aaa tac gcc aaa aac gaa cca acg ctc atc     336
Ala Thr Asp Glu Leu Glu Lys Tyr Ala Lys Asn Glu Pro Thr Leu Ile
            100                 105                 110 cgt ata tgg ggt gat gct ttg ttt gat atc gtt gac aaa gat caa aat     384
Arg Ile Trp Gly Asp Ala Leu Phe Asp Ile Val Asp Lys Asp Gln Asn
        115                 120                 125 gga gcc att aca ctg gat gaa tgg aaa gca tac acc aaa gct gct ggt     432
Gly Ala Ile Thr Leu Asp Glu Trp Lys Ala Tyr Thr Lys Ala Ala Gly
    130                 135                 140
```

```
atc atc caa tca tca gaa gat tgc gag gaa aca ttc aga gtg tgc gat     480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat     528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt     576
Leu Gly Phe Trp Tyr Thr Met Asp Pro Ala Cys Glu Lys Leu Tyr Gly
            180                 185                 190 gga gct gtc ccc taa                                                 591
Gly Ala Val Pro
        195

<210> SEQ ID NO 2
<211> LENGTH: 196
<212> TYPE: PRT
<213> ORGANISM: Aequorea victoria

<400> SEQUENCE: 2

Met Thr Ser Lys Gln Tyr Ser Val Lys Leu Thr Ser Asp Phe Asp Asn
1               5                   10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
        35                  40                  45

Asp Ile Val Ile Asn Asn Leu Gly Ala Thr Pro Glu Gln Ala Lys Arg
    50                  55                  60

His Lys Asp Ala Val Glu Ala Phe Phe Gly Gly Ala Gly Met Lys Tyr
65              70                  75                  80

Gly Val Glu Thr Asp Trp Pro Ala Tyr Ile Gly Trp Lys Lys Leu
                85                  90                  95

Ala Thr Asp Glu Leu Glu Lys Tyr Ala Lys Asn Glu Pro Thr Leu Ile
            100                 105                 110

Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
    130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195

<210> SEQ ID NO 3
<211> LENGTH: 597
<212> TYPE: DNA
<213> ORGANISM: Clytia gregaria
<220> FEATURE:
<221> NAME/KEY: CDS
<222> LOCATION: (1)..(597)

<400> SEQUENCE: 3 atg gct gac act gca tca aaa tac gcc gtc aaa ctc aga ccc aac ttc     48
Met Ala Asp Thr Ala Ser Lys Tyr Ala Val Lys Leu Arg Pro Asn Phe
1               5                   10                  15 gac aac cca aaa tgg gtc aac aga cac aaa ttt atg ttc aac ttt ttg     96
```

```
                Asp Asn Pro Lys Trp Val Asn Arg His Lys Phe Met Phe Asn Phe Leu
                            20                  25                  30 gac att aac ggc gac gga aaa atc act ttg gat gaa atc gtc tcc aaa              144
Asp Ile Asn Gly Asp Gly Lys Ile Thr Leu Asp Glu Ile Val Ser Lys
            35                  40                  45 gct tcg gat gac att tgc gcc aaa ctt gga gca aca cca gaa cag acc              192
Ala Ser Asp Asp Ile Cys Ala Lys Leu Gly Ala Thr Pro Glu Gln Thr
50                  55                  60 aaa cgt cac cag gat gct gtc gaa gct ttc ttc aaa aag att ggt atg              240
Lys Arg His Gln Asp Ala Val Glu Ala Phe Phe Lys Lys Ile Gly Met
65                  70                  75                  80 gat tat ggt aaa gaa gtc gaa ttc cca gct ttt gtt gat gga tgg aaa              288
Asp Tyr Gly Lys Glu Val Glu Phe Pro Ala Phe Val Asp Gly Trp Lys
                85                  90                  95 gaa ctg gcc aat tat gac ttg aaa ctt tgg tct caa aac aag aaa tct              336
Glu Leu Ala Asn Tyr Asp Leu Lys Leu Trp Ser Gln Asn Lys Lys Ser
            100                 105                 110 ttg atc cgc gac tgg gga gaa gct gtt ttc gac att ttt gac aaa gac              384
Leu Ile Arg Asp Trp Gly Glu Ala Val Phe Asp Ile Phe Asp Lys Asp
            115                 120                 125 gga agt ggc tca atc agt ttg gac gaa tgg aag gct tat gga cga atc              432
Gly Ser Gly Ser Ile Ser Leu Asp Glu Trp Lys Ala Tyr Gly Arg Ile
130                 135                 140 tct gga atc tgc tca tca gac gaa gac gcc gaa aag acc ttc aaa cat              480
Ser Gly Ile Cys Ser Ser Asp Glu Asp Ala Glu Lys Thr Phe Lys His
145                 150                 155                 160 tgc gat ttg gac aac agt ggc aaa ctt gat gtt gat gag atg acc aga              528
Cys Asp Leu Asp Asn Ser Gly Lys Leu Asp Val Asp Glu Met Thr Arg
                165                 170                 175 caa cat ttg gga ttc tgg tac acc ttg gac ccc aac gct gat ggt ctt              576
Gln His Leu Gly Phe Trp Tyr Thr Leu Asp Pro Asn Ala Asp Gly Leu
            180                 185                 190 tac ggc aat ttt gtt cct taa                                                  597
Tyr Gly Asn Phe Val Pro
            195

<210> SEQ ID NO 4
<211> LENGTH: 198
<212> TYPE: PRT
<213> ORGANISM: Clytia gregaria

<400> SEQUENCE: 4

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
            35                  40                  45

Ala Ser Asp Asp Ile Cys Ala Lys Leu Gly Ala Thr Pro Glu Gln Thr
50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
            115                 120                 125

Gly Ser Gly Ser Ile Ser Leu Asp Glu Trp Lys Ala Tyr Gly Arg Ile
```

```
                130                 135                 140
Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 5
<211> LENGTH: 657
<212> TYPE: DNA
<213> ORGANISM: Clytia gregaria
<220> FEATURE:
<221> NAME/KEY: CDS
<222> LOCATION: (1)..(657)

<400> SEQUENCE: 5 atg tcg gct tta gct gca aga tca aga ttg caa cgc aca gca aat ttt      48
Met Ser Ala Leu Ala Ala Arg Ser Arg Leu Gln Arg Thr Ala Asn Phe
1               5                   10                  15 cac acc agc ata ctg ttg gct aca gat tca aaa tac gcg gtc aaa ctc      96
His Thr Ser Ile Leu Leu Ala Thr Asp Ser Lys Tyr Ala Val Lys Leu
            20                  25                  30 gat cct gat ttt gca aat cca aaa tgg atc aac aga cac aaa ttt atg     144
Asp Pro Asp Phe Ala Asn Pro Lys Trp Ile Asn Arg His Lys Phe Met
        35                  40                  45 ttc aac ttt ttg gac ata aac ggt aat ggg aaa atc aca tta gat gaa     192
Phe Asn Phe Leu Asp Ile Asn Gly Asn Gly Lys Ile Thr Leu Asp Glu
    50                  55                  60 atc gtc tcc aaa gct tca gac gac att tgt gct aaa ctg gat gca aca     240
Ile Val Ser Lys Ala Ser Asp Asp Ile Cys Ala Lys Leu Asp Ala Thr
65                  70                  75                  80 cca gaa cag acc aaa cgt cac cag gat gct gtt gaa gcg ttt ttc aag     288
Pro Glu Gln Thr Lys Arg His Gln Asp Ala Val Glu Ala Phe Phe Lys
                85                  90                  95 aaa atg ggc atg gat tat ggt aaa gaa gtt gca ttc cca gaa ttt att     336
Lys Met Gly Met Asp Tyr Gly Lys Glu Val Ala Phe Pro Glu Phe Ile
            100                 105                 110 aag gga tgg gaa gag ttg gcc gaa cac gac ttg gaa ctc tgg tct caa     384
Lys Gly Trp Glu Glu Leu Ala Glu His Asp Leu Glu Leu Trp Ser Gln
        115                 120                 125 aac aaa agt aca ttg atc cgt gaa tgg gga gat gct gtt ttc gac att     432
Asn Lys Ser Thr Leu Ile Arg Glu Trp Gly Asp Ala Val Phe Asp Ile
    130                 135                 140 ttc gac aaa gac gca agt ggc tca atc agt tta gac gaa tgg aag gct     480
Phe Asp Lys Asp Ala Ser Gly Ser Ile Ser Leu Asp Glu Trp Lys Ala
145                 150                 155                 160 tac gga cga atc tct gga atc tgt cca tca gac gaa gac gct gag aag     528
Tyr Gly Arg Ile Ser Gly Ile Cys Pro Ser Asp Glu Asp Ala Glu Lys
                165                 170                 175 acg ttc aaa cat tgt gat ttg gac aac agt ggc aaa ctt gat gtt gat     576
Thr Phe Lys His Cys Asp Leu Asp Asn Ser Gly Lys Leu Asp Val Asp
            180                 185                 190 gag atg acc agg caa cat tta ggc ttc tgg tac aca ttg gat cca act     624
Glu Met Thr Arg Gln His Leu Gly Phe Trp Tyr Thr Leu Asp Pro Thr
        195                 200                 205 tct gat ggt ctt tat ggc aat ttt gtt ccc taa                         657
Ser Asp Gly Leu Tyr Gly Asn Phe Val Pro
    210                 215
```

<210> SEQ ID NO 6
<211> LENGTH: 218
<212> TYPE: PRT
<213> ORGANISM: Clytia gregaria

<400> SEQUENCE: 6

Met Ser Ala Leu Ala Ala Arg Ser Arg Leu Gln Arg Thr Ala Asn Phe
1               5                   10                  15

His Thr Ser Ile Leu Leu Ala Thr Asp Ser Lys Tyr Ala Val Lys Leu
            20                  25                  30

Asp Pro Asp Phe Ala Asn Pro Lys Trp Ile Asn Arg His Lys Phe Met
        35                  40                  45

Phe Asn Phe Leu Asp Ile Asn Gly Asn Gly Lys Ile Thr Leu Asp Glu
    50                  55                  60

Ile Val Ser Lys Ala Ser Asp Asp Ile Cys Ala Lys Leu Asp Ala Thr
65                  70                  75                  80

Pro Glu Gln Thr Lys Arg His Gln Asp Ala Val Glu Ala Phe Phe Lys
                85                  90                  95

Lys Met Gly Met Asp Tyr Gly Lys Glu Val Ala Phe Pro Glu Phe Ile
            100                 105                 110

Lys Gly Trp Glu Glu Leu Ala Glu His Asp Leu Glu Leu Trp Ser Gln
        115                 120                 125

Asn Lys Ser Thr Leu Ile Arg Glu Trp Gly Asp Ala Val Phe Asp Ile
    130                 135                 140

Phe Asp Lys Asp Ala Ser Gly Ser Ile Ser Leu Asp Glu Trp Lys Ala
145                 150                 155                 160

Tyr Gly Arg Ile Ser Gly Ile Cys Pro Ser Asp Glu Asp Ala Glu Lys
                165                 170                 175

Thr Phe Lys His Cys Asp Leu Asp Asn Ser Gly Lys Leu Asp Val Asp
            180                 185                 190

Glu Met Thr Arg Gln His Leu Gly Phe Trp Tyr Thr Leu Asp Pro Thr
        195                 200                 205

Ser Asp Gly Leu Tyr Gly Asn Phe Val Pro
    210                 215

<210> SEQ ID NO 7
<211> LENGTH: 597
<212> TYPE: DNA
<213> ORGANISM: Mitrocoma cellularia
<220> FEATURE:
<221> NAME/KEY: CDS
<222> LOCATION: (1)..(597)

<400> SEQUENCE: 7 atg tca atg ggc agc aga tac gca gtc aag ctt acg act gac ttt gat      48
Met Ser Met Gly Ser Arg Tyr Ala Val Lys Leu Thr Thr Asp Phe Asp
1               5                   10                  15 aat cca aaa tgg att gct cga cac aag cac atg ttc aac ttc ctt gac      96
Asn Pro Lys Trp Ile Ala Arg His Lys His Met Phe Asn Phe Leu Asp
            20                  25                  30 atc aat tca aat ggc caa atc aat ctg aat gaa atg gtc cat aag gct     144
Ile Asn Ser Asn Gly Gln Ile Asn Leu Asn Glu Met Val His Lys Ala
        35                  40                  45 tca aac att atc tgc aag aag ctt gga gca aca gaa gaa caa acc aaa     192
Ser Asn Ile Ile Cys Lys Lys Leu Gly Ala Thr Glu Glu Gln Thr Lys
    50                  55                  60 cgt cat caa aag tgt gtc gaa gac ttc ttt ggg gga gct ggt ttg gaa     240
Arg His Gln Lys Cys Val Glu Asp Phe Phe Gly Gly Ala Gly Leu Glu

```
                                                                        65                              70                              75                              80
tat  gac  aaa  gat  acc  aca  tgg  cct  gag  tac  atc  gaa  gga  tgg  aag  agg              288
Tyr  Asp  Lys  Asp  Thr  Thr  Trp  Pro  Glu  Tyr  Ile  Glu  Gly  Trp  Lys  Arg
                        85                              90                              95 ttg  gct  aag  act  gaa  ttg  gaa  agg  cat  tca  aag  aat  caa  gtc  aca  ttg              336
Leu  Ala  Lys  Thr  Glu  Leu  Glu  Arg  His  Ser  Lys  Asn  Gln  Val  Thr  Leu
             100                             105                             110 atc  cga  tta  tgg  ggt  gat  gct  ttg  ttc  gac  atc  att  gac  aaa  gat  aga              384
Ile  Arg  Leu  Trp  Gly  Asp  Ala  Leu  Phe  Asp  Ile  Ile  Asp  Lys  Asp  Arg
             115                             120                             125 aat  gga  tcg  gtt  tcg  tta  gac  gaa  tgg  atc  cag  tac  act  cat  tgt  gct              432
Asn  Gly  Ser  Val  Ser  Leu  Asp  Glu  Trp  Ile  Gln  Tyr  Thr  His  Cys  Ala
        130                             135                             140 ggc  atc  caa  cag  tca  cgt  ggg  caa  tgc  gaa  gct  aca  ttt  gca  cat  tgc              480
Gly  Ile  Gln  Gln  Ser  Arg  Gly  Gln  Cys  Glu  Ala  Thr  Phe  Ala  His  Cys
145                             150                             155                             160 gat  tta  gat  ggt  gac  ggt  aaa  ctt  gat  gtg  gac  gaa  atg  aca  aga  caa              528
Asp  Leu  Asp  Gly  Asp  Gly  Lys  Leu  Asp  Val  Asp  Glu  Met  Thr  Arg  Gln
                       165                              170                             175 cat  ttg  gga  ttt  tgg  tat  tcg  gtc  gac  cca  act  tgt  gaa  gga  ctc  tac              576
His  Leu  Gly  Phe  Trp  Tyr  Ser  Val  Asp  Pro  Thr  Cys  Glu  Gly  Leu  Tyr
             180                             185                             190 ggt  ggt  gct  gta  cct  tat  taa                                                             597
Gly  Gly  Ala  Val  Pro  Tyr
             195
```

<210> SEQ ID NO 8
<211> LENGTH: 198
<212> TYPE: PRT
<213> ORGANISM: Mitrocoma cellularia

<400> SEQUENCE: 8

```
Met  Ser  Met  Gly  Ser  Arg  Tyr  Ala  Val  Lys  Leu  Thr  Thr  Asp  Phe  Asp
1                 5                                  10                                 15

Asn  Pro  Lys  Trp  Ile  Ala  Arg  His  Lys  His  Met  Phe  Asn  Phe  Leu  Asp
                       20                                  25                                  30

Ile  Asn  Ser  Asn  Gly  Gln  Ile  Asn  Leu  Asn  Glu  Met  Val  His  Lys  Ala
             35                                  40                                  45

Ser  Asn  Ile  Ile  Cys  Lys  Lys  Leu  Gly  Ala  Thr  Glu  Glu  Gln  Thr  Lys
50                                  55                                  60

Arg  His  Gln  Lys  Cys  Val  Glu  Asp  Phe  Phe  Gly  Gly  Ala  Gly  Leu  Glu
65                                  70                                  75                                  80

Tyr  Asp  Lys  Asp  Thr  Thr  Trp  Pro  Glu  Tyr  Ile  Glu  Gly  Trp  Lys  Arg
                       85                                  90                                  95

Leu  Ala  Lys  Thr  Glu  Leu  Glu  Arg  His  Ser  Lys  Asn  Gln  Val  Thr  Leu
             100                                 105                                 110

Ile  Arg  Leu  Trp  Gly  Asp  Ala  Leu  Phe  Asp  Ile  Ile  Asp  Lys  Asp  Arg
             115                                 120                                 125

Asn  Gly  Ser  Val  Ser  Leu  Asp  Glu  Trp  Ile  Gln  Tyr  Thr  His  Cys  Ala
        130                                 135                                 140

Gly  Ile  Gln  Gln  Ser  Arg  Gly  Gln  Cys  Glu  Ala  Thr  Phe  Ala  His  Cys
145                                 150                                 155                                 160

Asp  Leu  Asp  Gly  Asp  Gly  Lys  Leu  Asp  Val  Asp  Glu  Met  Thr  Arg  Gln
                       165                                 170                                 175

His  Leu  Gly  Phe  Trp  Tyr  Ser  Val  Asp  Pro  Thr  Cys  Glu  Gly  Leu  Tyr
             180                                 185                                 190

Gly  Gly  Ala  Val  Pro  Tyr
             195
```

```
<210> SEQ ID NO 9
<211> LENGTH: 588
<212> TYPE: DNA
<213> ORGANISM: Obelia longissima
<220> FEATURE:
<221> NAME/KEY: CDS
<222> LOCATION: (1)..(588)

<400> SEQUENCE: 9 atg tct tca aaa tac gca gtt aaa ctc aag act gac ttt gat aat cca      48
Met Ser Ser Lys Tyr Ala Val Lys Leu Lys Thr Asp Phe Asp Asn Pro
1               5                   10                  15 cga tgg atc aaa aga cac aag cac atg ttt gat ttc ctc gac atc aat      96
Arg Trp Ile Lys Arg His Lys His Met Phe Asp Phe Leu Asp Ile Asn
            20                  25                  30 gga aat gga aaa atc acc ctc gat gaa att gtg tcc aag gca tct gat     144
Gly Asn Gly Lys Ile Thr Leu Asp Glu Ile Val Ser Lys Ala Ser Asp
        35                  40                  45 gac ata tgt gcc aag ctc gaa gcc aca cca gaa caa aca aaa cgc cat     192
Asp Ile Cys Ala Lys Leu Glu Ala Thr Pro Glu Gln Thr Lys Arg His
    50                  55                  60 caa gtt tgt gtt gaa gct ttc ttt aga gga tgt gga atg gaa tat ggt     240
Gln Val Cys Val Glu Ala Phe Phe Arg Gly Cys Gly Met Glu Tyr Gly
65                  70                  75                  80 aaa gaa att gcc ttc cca caa ttc ctc gat gga tgg aaa caa ttg gcg     288
Lys Glu Ile Ala Phe Pro Gln Phe Leu Asp Gly Trp Lys Gln Leu Ala
                85                  90                  95 act tca gaa ctc aag aaa tgg gca aga aac gaa cct act ctc att cgt     336
Thr Ser Glu Leu Lys Lys Trp Ala Arg Asn Glu Pro Thr Leu Ile Arg
            100                 105                 110 gaa tgg gga gat gct gtc ttt gat att ttc gac aaa gat gga agt ggt     384
Glu Trp Gly Asp Ala Val Phe Asp Ile Phe Asp Lys Asp Gly Ser Gly
        115                 120                 125 aca atc act ttg gac gaa tgg aaa gct tat gga aaa atc tct ggt atc     432
Thr Ile Thr Leu Asp Glu Trp Lys Ala Tyr Gly Lys Ile Ser Gly Ile
    130                 135                 140 tct cca tca caa gaa gat tgt gaa gcg aca ttt cga cat tgc gat ttg     480
Ser Pro Ser Gln Glu Asp Cys Glu Ala Thr Phe Arg His Cys Asp Leu
145                 150                 155                 160 gac aac agt ggt gac ctt gat gtt gac gag atg aca aga caa cat ctt     528
Asp Asn Ser Gly Asp Leu Asp Val Asp Glu Met Thr Arg Gln His Leu
                165                 170                 175 gga ttc tgg tac act ttg gac cca gaa gct gat ggt ctc tat ggc aac     576
Gly Phe Trp Tyr Thr Leu Asp Pro Glu Ala Asp Gly Leu Tyr Gly Asn
            180                 185                 190 gga gtt ccc taa                                                     588
Gly Val Pro
        195

<210> SEQ ID NO 10
<211> LENGTH: 195
<212> TYPE: PRT
<213> ORGANISM: Obelia longissima

<400> SEQUENCE: 10

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
            20                  25                  30

Gly Asn Gly Lys Ile Thr Leu Asp Glu Ile Val Ser Lys Ala Ser Asp
        35                  40                  45
```

```
Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

Thr Ile Thr Leu Asp Glu Trp Lys Ala Tyr Gly Lys Ile Ser Gly Ile
130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 11
<211> LENGTH: 627
<212> TYPE: DNA
<213> ORGANISM: Beroe abyssicola
<220> FEATURE:
<221> NAME/KEY: CDS
<222> LOCATION: (1)..(627)

<400> SEQUENCE: 11 atg act gaa cgt ctg aac gag cag aac aac gag agt tac cgc tac ctg     48
Met Thr Glu Arg Leu Asn Glu Gln Asn Asn Glu Ser Tyr Arg Tyr Leu
1               5                   10                  15 aga agc gtg gga aac cag tgg cag ttc aac gta gag gac ctc cac ccc     96
Arg Ser Val Gly Asn Gln Trp Gln Phe Asn Val Glu Asp Leu His Pro
                20                  25                  30 aag atg ttg tcc cgt ctc tac aag aga ttc gat act ttc gat cta gac    144
Lys Met Leu Ser Arg Leu Tyr Lys Arg Phe Asp Thr Phe Asp Leu Asp
            35                  40                  45 agt gac ggt aag atg gag atg gac gag gtc ttg tac tgg ccc gac agg    192
Ser Asp Gly Lys Met Glu Met Asp Glu Val Leu Tyr Trp Pro Asp Arg
        50                  55                  60 atg agg cag ctg gta aac gct act gat gag cag gtt gag aag atg cgg    240
Met Arg Gln Leu Val Asn Ala Thr Asp Glu Gln Val Glu Lys Met Arg
65                  70                  75                  80 gat gct gtg aga gtt ttc ttt ttg cac aag gga gtg gag cca gta aac    288
Asp Ala Val Arg Val Phe Phe Leu His Lys Gly Val Glu Pro Val Asn
                85                  90                  95 ggt ctc ctc aga gag gac tgg gtg gaa gct aac aga gtc ttc gct gag    336
Gly Leu Leu Arg Glu Asp Trp Val Glu Ala Asn Arg Val Phe Ala Glu
            100                 105                 110 gct gag aga gaa aga gag cga cga gga gaa cct tct ctt atc gca ctt    384
Ala Glu Arg Glu Arg Glu Arg Arg Gly Glu Pro Ser Leu Ile Ala Leu
        115                 120                 125 ctc tcc aac tct tac tac gat gta ctg gat gat gac ggt gat ggt act    432
Leu Ser Asn Ser Tyr Tyr Asp Val Leu Asp Asp Asp Gly Asp Gly Thr
130                 135                 140 gtt gac gtc gat gaa tta aag acc atg atg aaa gca ttt gat gtg ccc    480
Val Asp Val Asp Glu Leu Lys Thr Met Met Lys Ala Phe Asp Val Pro
```

```
                    145                 150                 155                 160
cag gaa gct gcc tac acc ttc ttc gag aag gca gac act gac aag agt        528
Gln Glu Ala Ala Tyr Thr Phe Phe Glu Lys Ala Asp Thr Asp Lys Ser
                165                 170                 175 gga aag ttg gag aga aca gaa cta gtt cat ctc ttt aga aag ttt tgg        576
Gly Lys Leu Glu Arg Thr Glu Leu Val His Leu Phe Arg Lys Phe Trp
                180                 185                 190 atg gag cct tac gat cca cag tgg gac gga gtc tac gct tat aag tac        624
Met Glu Pro Tyr Asp Pro Gln Trp Asp Gly Val Tyr Ala Tyr Lys Tyr
                195                 200                 205 taa                                                                     627

<210> SEQ ID NO 12
<211> LENGTH: 208
<212> TYPE: PRT
<213> ORGANISM: Beroe abyssicola

<400> SEQUENCE: 12

Met Thr Glu Arg Leu Asn Glu Gln Asn Asn Glu Ser Tyr Arg Tyr Leu
1               5                   10                  15

Arg Ser Val Gly Asn Gln Trp Gln Phe Asn Val Glu Asp Leu His Pro
                20                  25                  30

Lys Met Leu Ser Arg Leu Tyr Lys Arg Phe Asp Thr Phe Asp Leu Asp
            35                  40                  45

Ser Asp Gly Lys Met Glu Met Asp Glu Val Leu Tyr Trp Pro Asp Arg
    50                  55                  60

Met Arg Gln Leu Val Asn Ala Thr Asp Glu Gln Val Glu Lys Met Arg
65                  70                  75                  80

Asp Ala Val Arg Val Phe Phe Leu His Lys Gly Val Pro Val Asn
                85                  90                  95

Gly Leu Leu Arg Glu Asp Trp Val Glu Ala Asn Arg Val Phe Ala Glu
            100                 105                 110

Ala Glu Arg Glu Arg Glu Arg Gly Glu Pro Ser Leu Ile Ala Leu
        115                 120                 125

Leu Ser Asn Ser Tyr Tyr Asp Val Leu Asp Asp Gly Asp Gly Thr
    130                 135                 140

Val Asp Val Asp Glu Leu Lys Thr Met Met Lys Ala Phe Asp Val Pro
145                 150                 155                 160

Gln Glu Ala Ala Tyr Thr Phe Phe Glu Lys Ala Asp Thr Asp Lys Ser
                165                 170                 175

Gly Lys Leu Glu Arg Thr Glu Leu Val His Leu Phe Arg Lys Phe Trp
            180                 185                 190

Met Glu Pro Tyr Asp Pro Gln Trp Asp Gly Val Tyr Ala Tyr Lys Tyr
        195                 200                 205
```

COELENTERAMIDE ANALOGS

CROSS REFERENCE TO RELATED APPLICATIONS

This application is the National Stage of International Application No. PCT/JP2010/051806, filed Feb. 8, 2010, which claims benefit of Japanese Application No. 2009-027904, filed Feb. 9, 2009, which are herein incorporated by reference in their entirety.

TECHNICAL FIELD

The present invention relates to coelenteramide analogs, fluorescent proteins comprising coelenteramide analogs, and so on.

BACKGROUND ART

Coelenteramide (CTMD) is an oxidation product of coelenterazine. CTMD is produced in the luminescence process of the calcium-binding photoproteins from coelenterates and in the luminescence process of coelenterazine (CTZ) type luciferases from *Renilla, Gaussia*, etc.

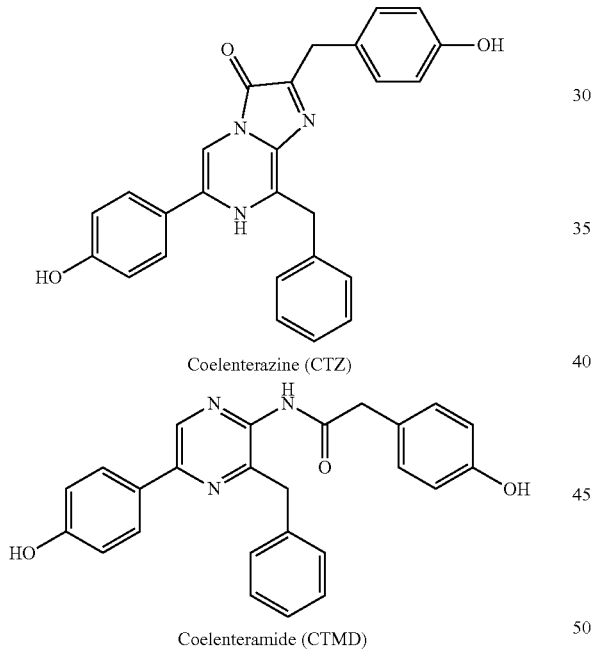

The calcium-binding photoprotein is a member of the photoproteins which emits light upon specific binding with $Ca^{2+}$ and is a complex of the peroxide of coelenterazine and an apoprotein (Non-Patent Literature 1. Head, J. F. et al. (2000) Nature 405: 372-376). Among the calcium-binding photoproteins, a representative photoprotein is aequorin, which is derived from luminous *Aequorea victoria*. In addition to aequorin, obelin, mitrocomin, clytin-I, clytin-II, etc. are known. Their luminescence mechanisms are considered to be basically the same. After the luminescence reaction of aequorin by the addition of $Ca^{2+}$, the aequorin solution shows blue fluorescence. It is therefore considered that a complex of CTMD which is the oxidation product of CTZ and apoaequorin-$Ca^{2+}$ would be formed, and this complex is referred to as BFP (Blue Fluorescent Protein). In recent years, the process for the quantitative preparation of BFP from recombinant aequorin has been established (Non-Patent Literatures 2 and 3: Inouye, S. (2004) FEBS Lett. 577:105-110, Inouye, S, and Sasaki, S (2006) FEBS Lett. 580: 1977-1982). It has been shown that BFP is a fluorescent protein with heat stability and has a luciferase activity when CTZ serves as a substrate. On the other hand, it was also shown that a greenish fluorescent protein (gFP) is produced by removing $Ca^{2+}$ from apoaequorin-$Ca^{2+}$. Furthermore, the method for regenerating aequorin having luminescence activity has been also established to form gFP by adding CTZ. BFP is a only protein that has the fluorescence ability and luciferase activity and can be regenerated to aequorin. Accordingly, BFP has possibilities to apply as a reporter protein in the field of cell biology and is remarkable protein.

The following fluorescent coelenteramide-related compounds are disclosed in Non-Patent Literatures 4 to 21.

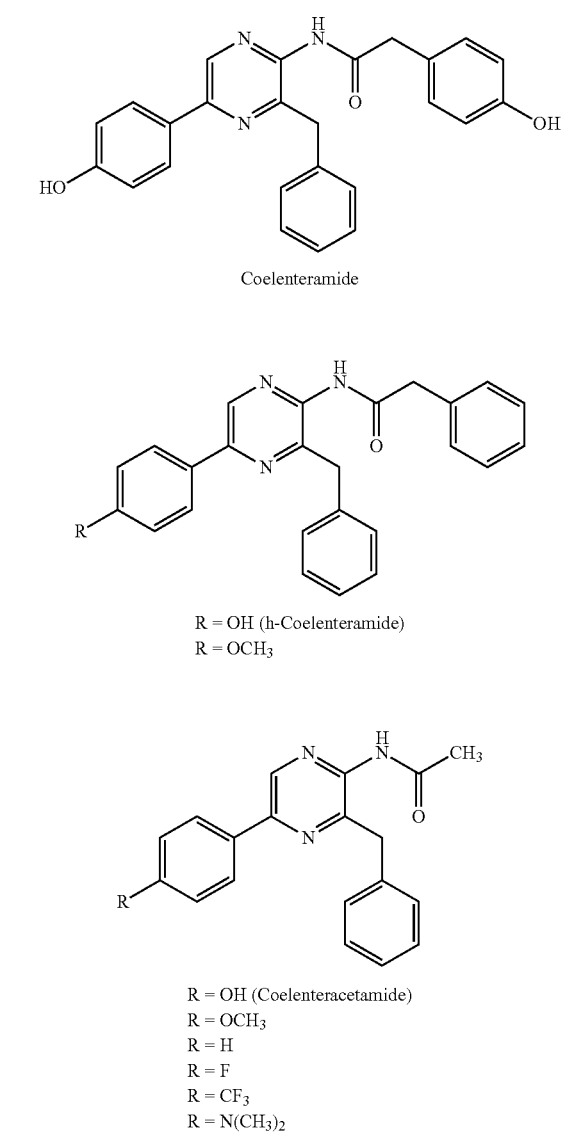

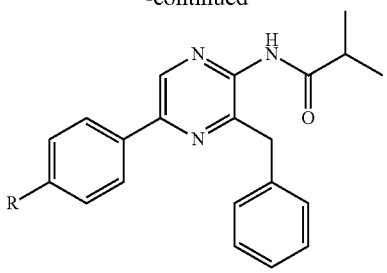
R = OCH₂Ph
R = OH
R = H
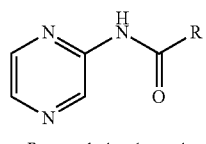
R = methyl or benzyl
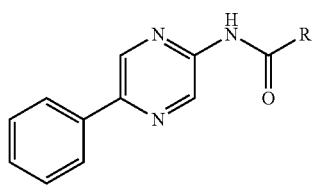
R = methyl or benzyl
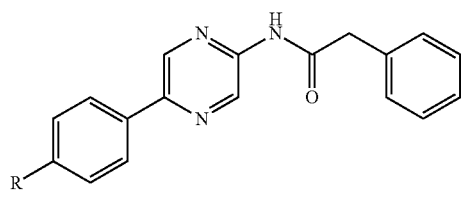
R = OH or OCH₃,
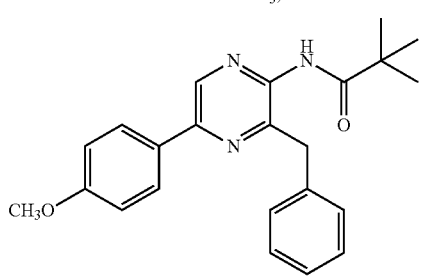
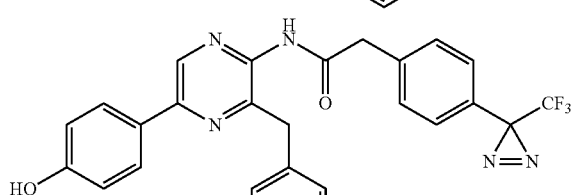
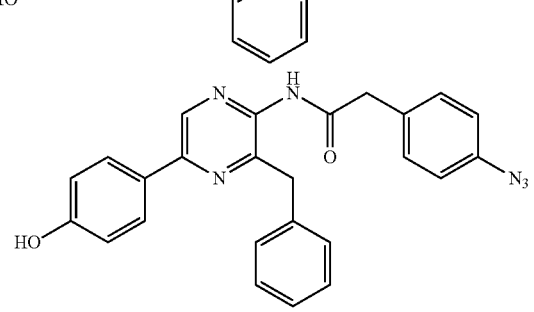
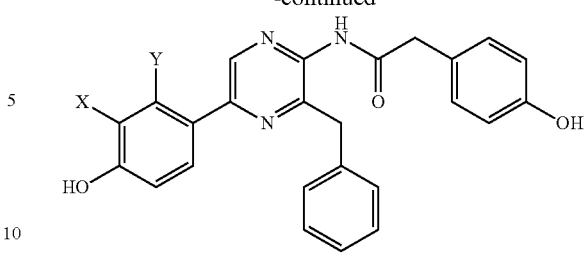
X = F, Y = H
X = Y = F
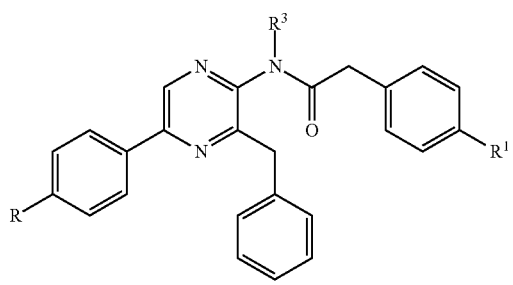
R¹ = OH, R² = OCH₃, R³ = H
R¹ = H, R² = OH, R³ = CH₃
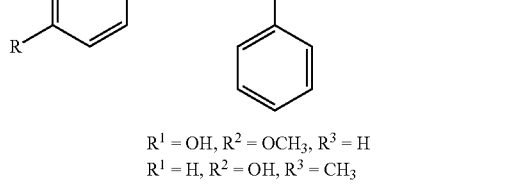
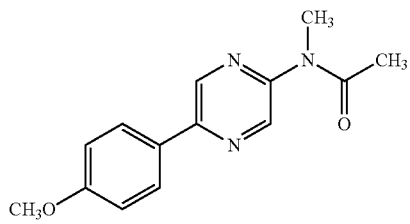
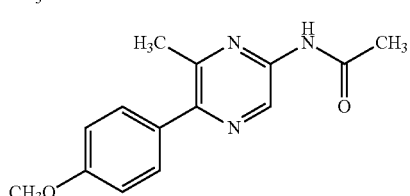
n = 1, 2, 3
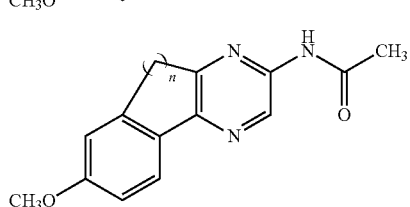
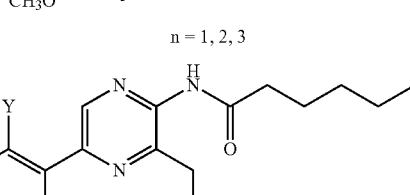
R = OH, X = H, Y = H
R = OCH₃, X = H, Y = H
R = OH, X = F, Y = H
R = OH, X = H, Y = F
R = OH, X = F, Y = F -continued

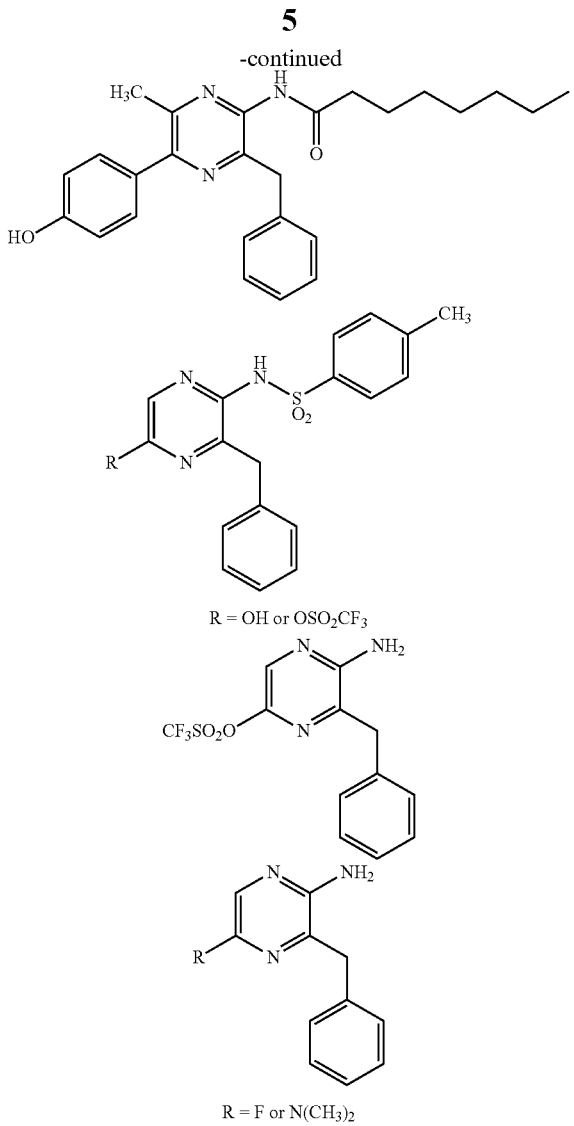

R = OH or OSO$_2$CF$_3$

R = F or N(CH$_3$)$_2$

The structures of the coelenteramide-related compounds described above and their fluorescence properties are described in Non-Patent Literatures 4 to 21.

CITATION LIST

Patent Literature

[Patent Literature 1] PCT International Publication Pamphlet WO2005/014633

Non-Patent Literature

[Non-Patent Literature 1] Head, J. F. et al. Nature 405, 372-376 (2000)
[Non-Patent Literature 2] Inouye, S. FEBS Lett. 577, 105-110 (2004)
[Non-Patent Literature 3] Inouye, S, and Sasaki, S. FEBS Lett. 580, 1977-1982 (2006)
[Non-Patent Literature 4] O. Shimomura, F. H. Johnson, Tetrahedron Lett., 31, 2963 (1973).
[Non-Patent Literature 5] K. Hori, J. E. Wampler, J. C. Matthews, M. J. Cormier, Biochemistry, 12, 4463 (1973).
[Non-Patent Literature 6] F. McCapra, M. J. Manning, J. Chem. Soc., Chem. Commun., 467 (1973).
[Non-Patent Literature 7] K. Hori, J. E. Wampler, M. J. Cormier, J. Chem. Soc., Chem. Commun., 492 (1973).
[Non-Patent Literature 8] K. Teranishi, T. Goto, Bull. Chem. Soc. Jpn., 63, 3132 (1990).
[Non-Patent Literature 9] T. Hirano, Y. Gomi, T. Takahashi, K. Kitahara, C. F. Qi, I. Mizogushi, S. Kyushin, M. Ohashi, Tetrahedron Lett., 33, 5771 (1992).
[Non-Patent Literature 10] K. Teranishi, K. Ueda, H. Nakao, M. Hisamatsu, T. Yamada, Tetrahedron Lett., 35, 8181 (1994).
[Non-Patent Literature 11] F. Q. Chen, J. L. Zheng, T. Hirano, H. Niwa, Y. Ohmiya, M. Ohashi, J. Chem. Soc., Perkin Trans. 1, 2129 (1995).
[Non-Patent Literature 12] R. Saito, T. Hirano, H. Niwa, M. Ohashi, J. Chem. Soc., Perkin Trans. 2, 1711 (1997).
[Non-Patent Literature 13] K. Teranishi, M. Hisamatsu, T. Yamada, Tetrahedron Lett., 38, 2689 (1997).
[Non-Patent Literature 14] T. Hirano, Y. Ohmiya, S. Maki, H. Niwa, M. Ohashi, Tetrahedron Lett., 39, 5541 (1998).
[Non-Patent Literature 15] F. Q. Chen, J. L. Zheng, T. Hirano, Y. Ohmiya, S. Maki, H. Niwa, M. Ohashi, Bull. Chem. Soc. Jpn., 73, 465 (2000).
[Non-Patent Literature 16] O. Shimomura, K. Teranishi, Luminescence, 15, 51 (2000).
[Non-Patent Literature 17] K. Teranishi, Luminescence, 16, 367 (2001).
[Non-Patent Literature 18] Y. Imai, T. Shibata, S. Maki, H. Niwa, M. Ohashi, T. Hirano, J. Photochem. Photobiol., A, 146, 95 (2001).
[Non-Patent Literature 19] M. Kuse, N. Kondo, Y. Ohyabu, M. Isobe, Tetrahedron, 60, 835 (2004).
[Non-Patent Literature 20] N. Kondo, M. Kuse, T. Mutarapat, N. Thasana, M. Isobe, Heterocycles, 65, 843 (2005).
[Non-Patent Literature 21] K. Mori, S. Maki, H. Niwa, H. Ikeda, T. Hirano, Tetrahedron, 62, 6272 (2006).

SUMMARY OF THE INVENTION

Problems to be Solved by the Invention

Under the situations described above, there has been a need for coelenteramide analogs, which have different fluorescence properties from those of the existing ones, fluorescent proteins comprising such coelenteramide analogs, and so on.

Means of Solving the Problems

The present inventors have made extensive investigations to solve the problems described above and as a result, have found that some thioamide-based coelenteramide analogs and some sulfonamide-based coelenteramide analogs exhibit different fluorescence properties from those of the existing ones, and the like. The present invention has thus come to be accomplished.

That is, the present invention provides the following coelenteramide analogs, fluorescent proteins, and so on.

(1) A compound represented by general formula (1) below:

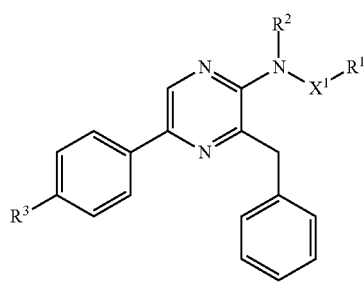

(1)

wherein:

$R^1$ is a substituted or unsubstituted aryl, a substituted or unsubstituted arylalkyl, a straight or branched alkyl which may optionally be substituted with an alicyclic group, an alicyclic group or a heterocyclic group;

$R^2$ is hydrogen or $-(SO_2)R^4$;

$R^3$ is hydrogen, hydroxy, methoxy or acetoxy;

$R^4$ is a substituted or unsubstituted aryl, a substituted or unsubstituted arylalkyl, or a straight or branched alkyl which may optionally be substituted with an alicyclic group;

and, $X^1$ is $-C(=S)-$ or $-SO_2-$.

(2) The compound according to (1) above, wherein $R^1$ in the general formula (1) is phenyl, p-methylphenyl, p-hydroxyphenyl, p-methoxyphenyl, p-acetoxyphenyl, p-nitrophenyl, benzyl, α-hydroxybenzyl, 4-methylbenzyl, 4-hydroxybenzyl, 4-methoxybenzyl, 4-acetoxybenzyl, 4-nitrobenzyl, phenylethyl, methyl, ethyl, propyl, 2-methylpropyl, 2-methylpropanyl, cyclohexylmethyl, cyclohexylethyl, adamantylmethyl, cyclopentylmethyl, cyclohexyl or thiophen-2-yl.

(3) The compound according to (1) or (2) above, wherein $R^2$ in the general formula (1) is hydrogen, benzenesulfonyl, p-toluenesulfonyl, 4-hydroxyphenylsulfonyl, 4-methoxyphenylsulfonyl, 4-acetoxyphenylsulfonyl, 4-nitrophenylsulfonyl, benzylsulfonyl, α-hydroxybenzylsulfonyl, 4-methylbenzylsulfonyl, 4-hydroxybenzylsulfonyl, 4-methoxybenzylsulfonyl, 4-acetoxybenzylsulfonyl, 4-nitrobenzylsulfonyl, phenylethylsulfonyl, methanesulfonyl, ethylsulfonyl, propylsulfonyl, 2-methylpropylsulfonyl, 2-methylpropanylsulfonyl, cyclohexylmethylsulfonyl, cyclohexylethylsulfonyl, adamantylmethylsulfonyl or cyclopentylmethylsulfonyl.

(4) The compound according to any one of (1) to (3) above, which is selected from the group consisting of the compounds described below.

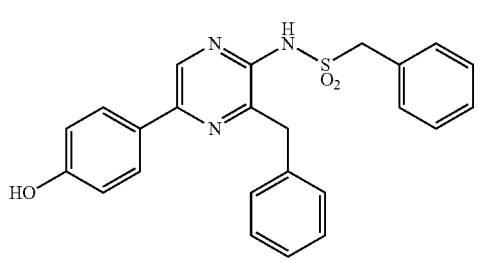

-continued

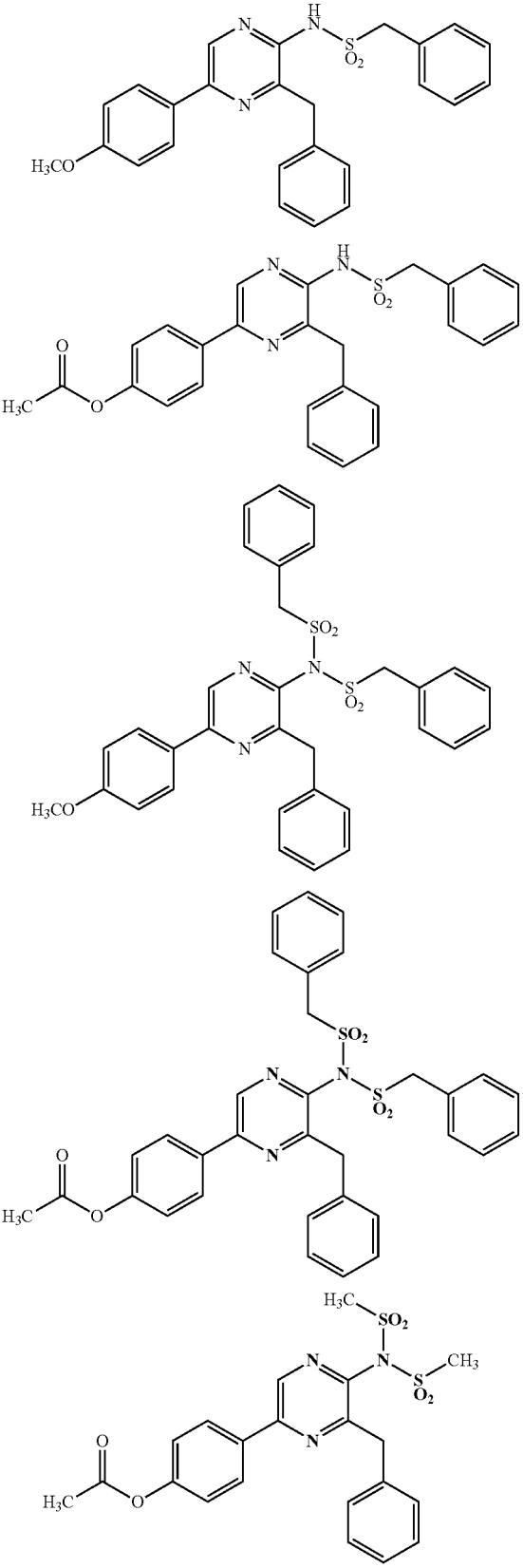

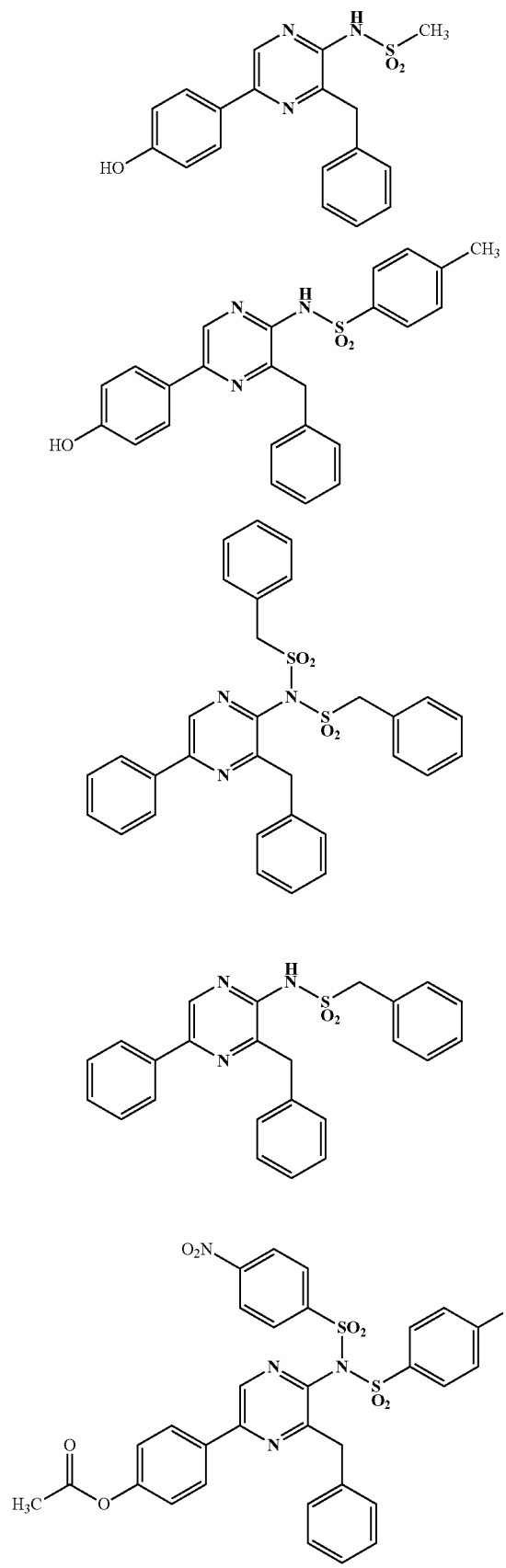
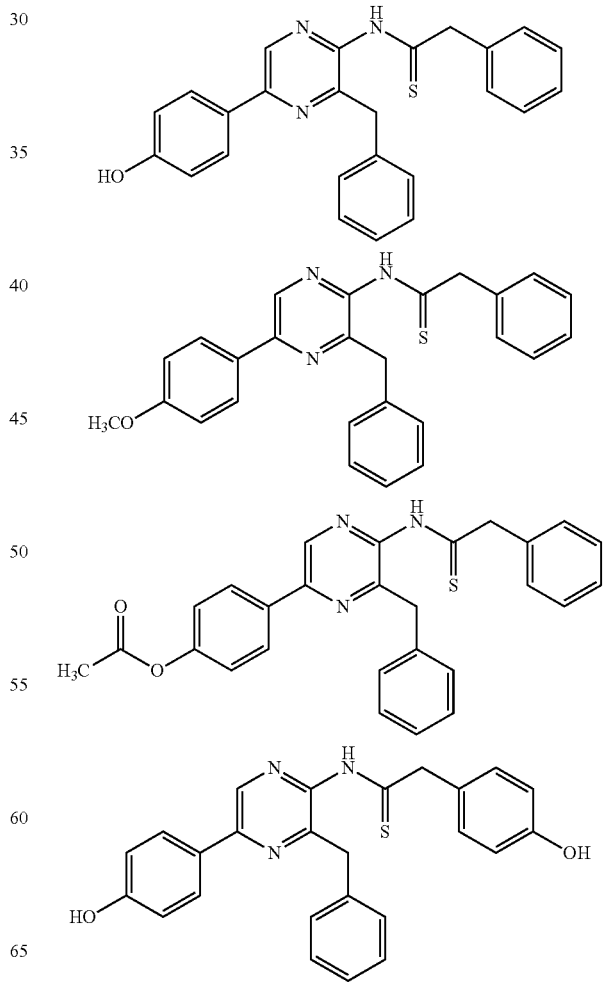
(5) The compound according to any one of (1) to (3) above, which is selected from the group consisting of the compounds described below.

-continued

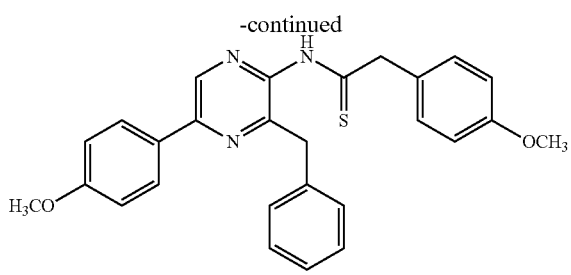

(5a) The compound according to any one of (1) to (3) above, which is selected from the group consisting of the compounds described below.

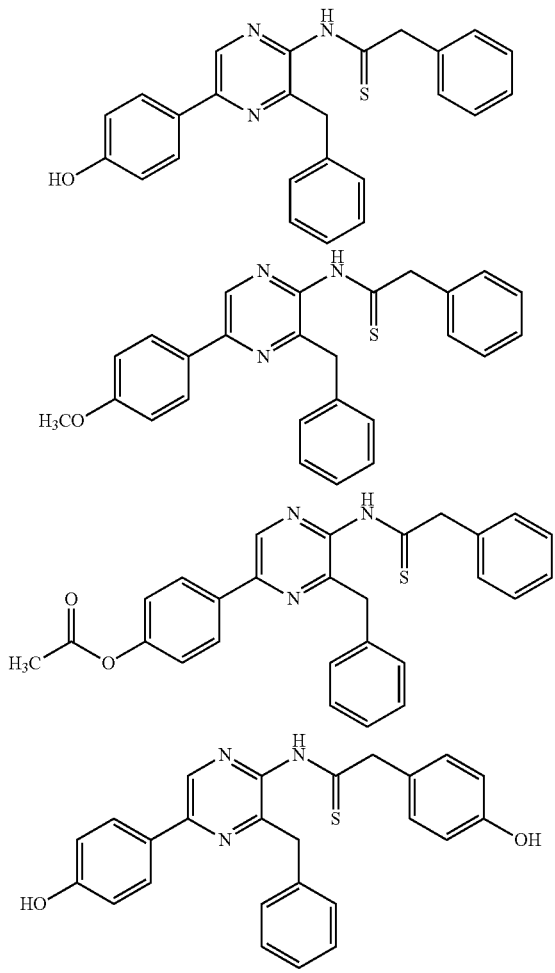

(6) A blue fluorescent protein comprising the compound according to any one of (1) to (5a) above, the apoprotein of a calcium-binding photoprotein and a calcium ion or a divalent or trivalent ion substitutable for a calcium ion.

(7) A process for producing a blue fluorescent protein, which comprises reacting the compound according to any one of (1) to (5a) above with the apoprotein of a calcium-binding photoprotein in the presence of a calcium ion or a divalent or trivalent ion substitutable for a calcium ion.

(8) The process according to (7) above, wherein the reaction is performed in the presence of a reducing agent.

(9) A greenish fluorescent protein comprising the compound according to any one of (1) to (5a) above and the apoprotein of a calcium-binding photoprotein.

(10) A process for producing a greenish fluorescent protein, which comprises treating the blue fluorescent protein according to (6) above with a chelating agent for removing a calcium ion or a divalent or trivalent ion substitutable for a calcium ion.

(11) A process for producing a calcium-binding photoprotein, which comprises reacting the greenish fluorescent protein according to (9) above with coelenterazine or an analog thereof.

(12) The process according to (11) above, wherein the reaction of the fluorescent protein with coelenterazine or an analog thereof is performed in the presence of a reducing agent.

Effect of the Invention

In some embodiments of the present invention, coelenteramide analogs exhibit different fluorescence properties from those of conventional ones. In a preferred embodiment of the present invention, coelenteramide analogs show relatively high fluorescence intensity in an aqueous solvent.

MODE FOR CARRYING OUT THE INVENTION

Figure 1:
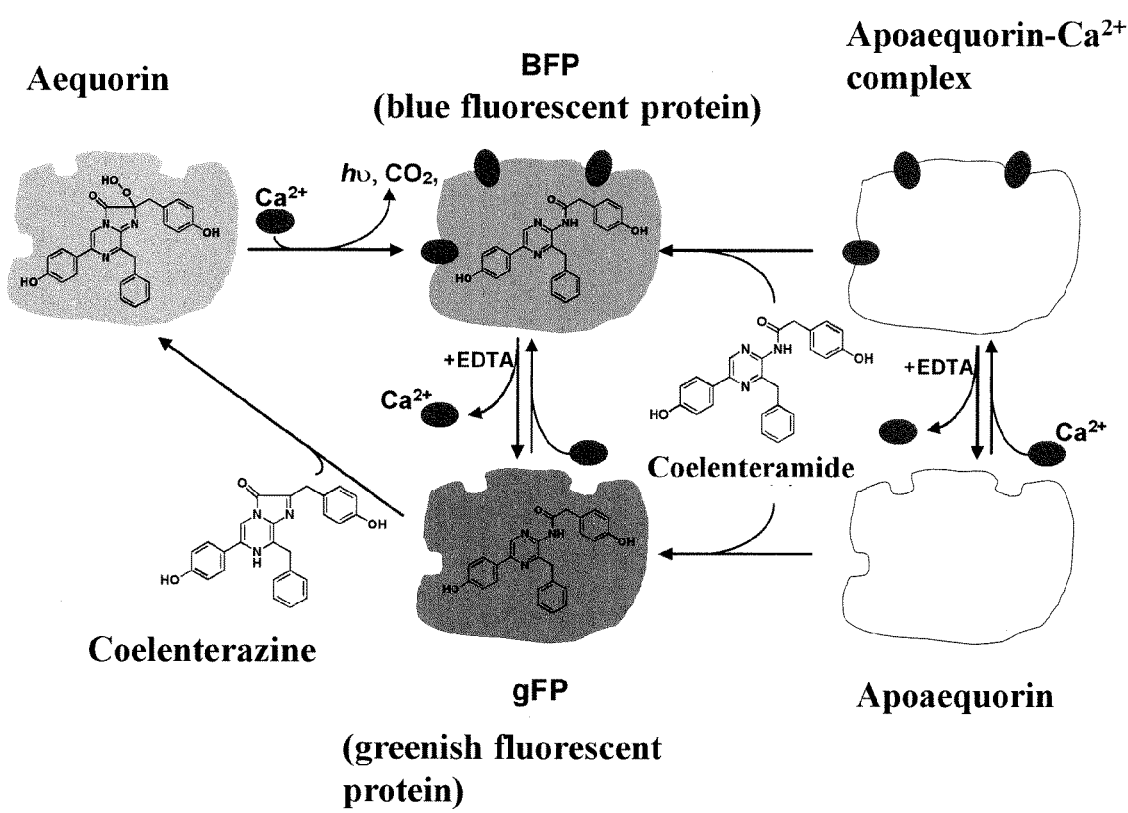
FIG. 1 shows a scheme for producing BFP, gFP, aequorin, etc. from coelenteramide.

Hereinafter the present invention is described in detail.

1. Coelenteramide Analogs

The present invention provides the compounds represented by general formula (1) below (coelenteramide analogs of the invention).

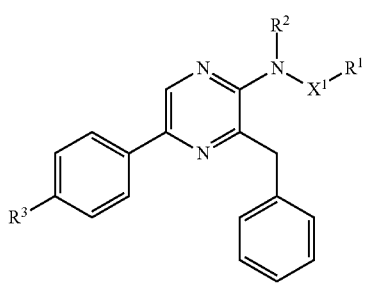

wherein:
$R^1$ is a substituted or unsubstituted aryl, a substituted or unsubstituted arylalkyl, a straight or branched alkyl which may optionally be substituted with an alicyclic group, an alicyclic group or a heterocyclic group;
$R^2$ is hydrogen or $-(SO_2)R^4$;

$R^3$ is hydrogen, hydroxy, methoxy or acetoxy;
$R^4$ is a substituted or unsubstituted aryl, a substituted or unsubstituted arylalkyl, or a straight or branched alkyl which may optionally be substituted with an alicyclic group; and,
$X^1$ is —C(=S)— or —SO$_2$—.

The "substituted or unsubstituted aryl" in $R^1$ is, for example, an aryl having 1 to 5 substituents or an unsubstituted aryl. The substituent includes, for example, at least one selected from the group consisting of a halogen (fluorine, chlorine, bromine or iodine, etc.), hydroxy, an alkyl having 1 to 6 carbon atoms, an alkoxyl having 1 to 6 carbon atoms, amino, and a dialkylamino having 1 to 6 carbon atoms, etc. In some embodiments of the present invention, the substituent is hydroxy. Specific examples of the "substituted or unsubstituted aryl" are phenyl, p-hydroxyphenyl, p-methoxyphenyl, p-acetoxyphenyl, p-nitrophenyl, p-aminophenyl, p-dimethylaminophenyl, etc., preferably, phenyl, p-hydroxyphenyl, p-methoxyphenyl, p-acetoxyphenyl, p-nitrophenyl, etc. In some embodiments of the present invention, the "substituted or unsubstituted aryl" is a substituted aryl, which is, e.g., p-hydroxyphenyl, p-methoxyphenyl, p-acetoxyphenyl, p-nitrophenyl, etc.

The "substituted or unsubstituted arylalkyl" in $R^1$ is, for example, an arylalkyl having 1 to 5 substituents or an unsubstituted arylalkyl. The substituent includes, for example, a halogen (fluorine, chlorine, bromine or iodine, etc.), hydroxy, an alkyl having 1 to 6 carbon atoms, an alkoxyl having 1 to 6 carbon atoms, amino, a dialkylamino having 1 to 6 carbon atoms, etc. Examples of the "substituted or unsubstituted arylalkyl" include, for example, benzyl, α-hydroxybenzyl, 4-methylbenzyl, 4-hydroxybenzyl, 4-methoxybenzyl, 4-acetoxybenzyl, 4-nitrobenzyl, phenylethyl-4-hydroxybenzyl, 4-dimethylaminobenzyl, etc., preferably, benzyl, α-hydroxybenzyl, 4-methylbenzyl, 4-hydroxybenzyl, 4-methoxybenzyl, 4-acetoxybenzyl, 4-nitrobenzyl, phenylethyl, etc. In some embodiments of the present invention, the "substituted or unsubstituted arylalkyl" is a hydroxy-substituted arylalkyl and examples are α-hydroxybenzyl, 4-hydroxybenzyl, etc. In another embodiment of the present invention, the "substituted or unsubstituted arylalkyl" is an unsubstituted arylalkyl, which is, e.g., benzyl, phenylethyl, etc.

The "straight or branched alkyl which may optionally be substituted with an alicyclic group" in $R^1$ is an unsubstituted straight or branched alkyl, or a straight or branched alkyl which is substituted with, e.g., 1 to 10 alicyclic groups. Examples of the alicyclic group include, for example, cyclohexyl, cyclopentyl, adamantyl, cyclobutyl, cyclopropyl, etc. Preferably, the alicyclic group is cyclohexyl, cyclopentyl, adamantyl, etc. Examples of the "straight or branched alkyl which may optionally be substituted with an alicyclic group" include methyl, ethyl, propyl, 2-methylpropyl, 2-methylpropanyl, cyclohexylmethyl, cyclohexylethyl, adamantylmethyl, cyclopentylmethyl, cyclobutylmethyl, cyclopropylmethyl, etc., preferably, methyl, ethyl, propyl, 2-methylpropyl, 2-methylpropanyl, cyclohexylmethyl, cyclohexylethyl, adamantylmethyl, cyclopentylmethyl, etc. In some embodiments of the present invention, the "straight or branched alkyl which may optionally be substituted with an alicyclic group" is a straight alkyl which may optionally be substituted with an alicyclic group and examples are methyl, ethyl, propyl, adamantylmethyl, cyclopentylmethyl, cyclohexylmethyl, cyclohexylethyl, etc.

The "alicyclic group" in $R^1$ includes, for example, cyclohexyl, cyclopentyl, adamantyl, cyclobutyl, cyclopropyl, etc. Preferably, the alicyclic group is cyclohexyl, etc.

The "heterocyclic group" in $R^1$ includes, for example, a group derived from a 5- to 7-membered ring containing, besides carbon atoms, 1 to 3 atoms selected from the group consisting of N, O and S as the atoms constituting the ring and bonded via carbon atoms, a group formed by fusing 2 or more of such rings and bonded via carbon, or a group formed by fusing such a ring to a benzene ring and bonding via carbon atoms. Examples of the "heterocyclic group" are thiophen-2-yl, 2-furanyl, 4-pyridyl, etc. In some embodiments of the present invention, the "heterocyclic group" is a heterocyclic group containing sulfur, e.g., thiophen-2-yl.

In a preferred embodiment of the present invention, $R^1$ is phenyl, p-methylphenyl, p-hydroxyphenyl, p-methoxyphenyl, p-acetoxyphenyl, p-nitrophenyl, benzyl, α-hydroxybenzyl, 4-methylbenzyl, 4-hydroxybenzyl, 4-methoxybenzyl, 4-acetoxybenzyl, 4-nitrobenzyl, phenylethyl, methyl, ethyl, propyl, 2-methylpropyl, 2-methylpropanyl, cyclohexylmethyl, cyclohexylethyl, adamantylmethyl, cyclopentylmethyl, cyclohexyl, thiophen-2-yl, etc. In a more preferred embodiment of the present invention, $R^1$ is p-methylphenyl, p-nitrophenyl, benzyl, methyl, etc.

In "—(SO$_2$)R$^4$" shown by $R^2$, the "substituted or unsubstituted aryl" in $R^4$ is an aryl having, e.g., 1 to 5 substituents or an unsubstituted aryl. The substituent includes, for example, at least one selected from the group consisting of a halogen (fluorine, chlorine, bromine or iodine, etc.), hydroxy, an alkyl having 1 to 6 carbon atoms, an alkoxyl having 1 to 6 carbon atoms, amino, a dialkylamino having 1 to 6 carbon atoms, and the like. In some embodiments of the present invention, the substituent is hydroxy. Specific examples of the "substituted or unsubstituted aryl" are phenyl, p-hydroxyphenyl, p-methoxyphenyl, p-acetoxyphenyl, p-nitrophenyl, p-hydroxybenzyl, p-dimethylaminobenzyl, etc., preferably, phenyl, p-hydroxyphenyl, p-methoxyphenyl, p-acetoxyphenyl, p-nitrophenyl, etc. In some embodiments of the present invention, the "substituted or unsubstituted aryl" is a substituted aryl and examples are p-hydroxyphenyl, p-methoxyphenyl, p-acetoxyphenyl, p-nitrophenyl, etc.

The "substituted or unsubstituted arylalkyl" in $R^4$ is an arylalkyl having, e.g., 1 to 6 substituents or an unsubstituted arylalkyl. The substituent includes, for example, a halogen (fluorine, chlorine, bromine or iodine, etc.), hydroxy, an alkyl having 1 to 6 carbon atoms, an alkoxyl having 1 to 6 carbon atoms, amino, a dialkylamino having 1 to 6 carbon atoms, etc. Examples of the "substituted or unsubstituted arylalkyl" are benzyl, α-hydroxybenzyl, 4-methylbenzyl, 4-hydroxybenzyl, 4-methoxybenzyl, 4-acetoxybenzyl, 4-nitrobenzyl, phenylethyl, 4-hydroxybenzyl, 4-dimethylaminobenzyl, etc., preferably, benzyl, α-hydroxybenzyl, 4-methylbenzyl, 4-hydroxybenzyl, 4-methoxybenzyl, 4-acetoxybenzyl, 4-nitrobenzyl, phenylethyl, etc. In some embodiments of the present invention, the "substituted or unsubstituted arylalkyl" is an arylalkyl substituted with hydroxy and examples are α-hydroxybenzyl, 4-hydroxybenzyl, etc. In another embodiment of the present invention, the "substituted or unsubstituted arylalkyl" is an unsubstituted arylalkyl and examples are benzyl, phenylethyl, etc.

The "straight or branched alkyl which may optionally be substituted with an alicyclic group" in $R^4$ is an unsubstituted straight or branched alkyl, or a straight or branched alkyl which is substituted with, e.g., 1 to 10 alicyclic groups. Examples of the alicyclic group include, for example, cyclohexyl, cyclopentyl, adamantyl, cyclobutyl, cyclopropyl, etc. Preferably, the alicyclic group is cyclohexyl, cyclopentyl, adamantyl, etc. Examples of the "straight or branched alkyl which may optionally be substituted with an alicyclic group" include methyl, ethyl, propyl, 2-methylpropyl, 2-methylpropanyl, cyclohexylmethyl, cyclohexylethyl, adamantylmethyl, cyclopentylmethyl, cyclobutylmethyl, cyclopropylmethyl, etc., preferably, methyl, ethyl, propyl, 2-methylpropyl, 2-methylpropanyl, cyclohexylmethyl, cyclohexylethyl, adamantylmethyl, cyclopentylmethyl, etc. In some embodiments of the present invention, the "straight or branched alkyl which may optionally be substituted with an alicyclic group" is a straight alkyl which may optionally be substituted with an alicyclic group and examples are methyl, ethyl, propyl, adamantylmethyl, cyclopentylmethyl, cyclohexylmethyl, cyclohexylethyl, etc.

In a preferred embodiment of the present invention, $R^2$ is hydrogen, benzenesulfonyl, p-toluenesulfonyl, 4-hydroxyphenylsulfonyl, 4-methoxyphenylsulfonyl, 4-acetoxyphenylsulfonyl, 4-nitrophenylsulfonyl, benzylsulfonyl, α-hydroxybenzylsulfonyl, 4-methylbenzylsulfonyl, 4-hydroxybenzylsulfonyl, 4-methoxybenzylsulfonyl, 4-acetoxybenzylsulfonyl, 4-nitrobenzylsulfonyl, phenylethylsulfonyl, methanesulfonyl, ethyl sulfonyl, propylsulfonyl, 2-methylpropylsulfonyl, 2-methylpropanylsulfonyl, cyclohexylmethylsulfonyl, cyclohexylethylsulfonyl, adamantylmethylsulfonyl, cyclopentylmethylsulfonyl, etc. In a more preferred embodiment of the present invention, $R^2$ is hydrogen, benzylsulfonyl, methanesulfonyl, nitrobenzenesulfonyl, etc.

In some embodiments of the present invention, the compound represented by general formula (1) is a compound represented by general formula (2) below (the sulfonamide-based coelenteramides of the present invention):

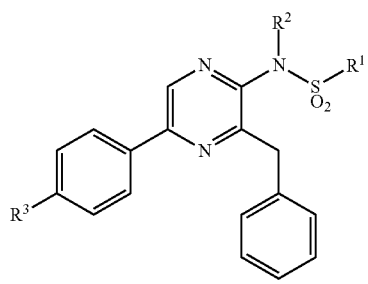

(2)

wherein $R^1$, $R^2$ and $R^3$ are the same as defined above.

Preferably, the compound represented by general formula (2) is a compound selected from the group consisting of the compounds described below.

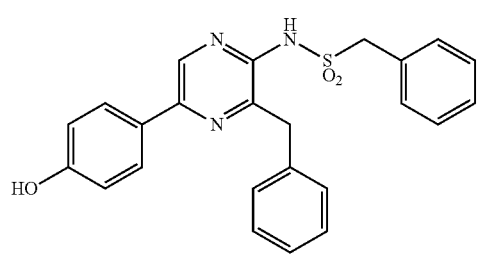

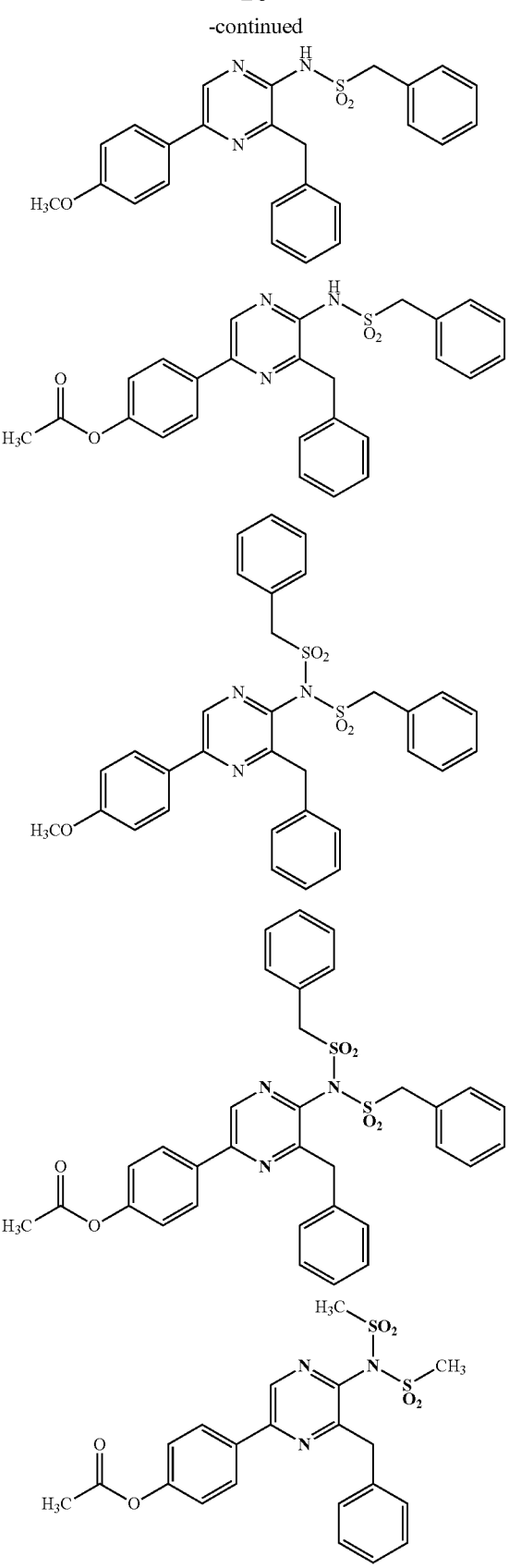

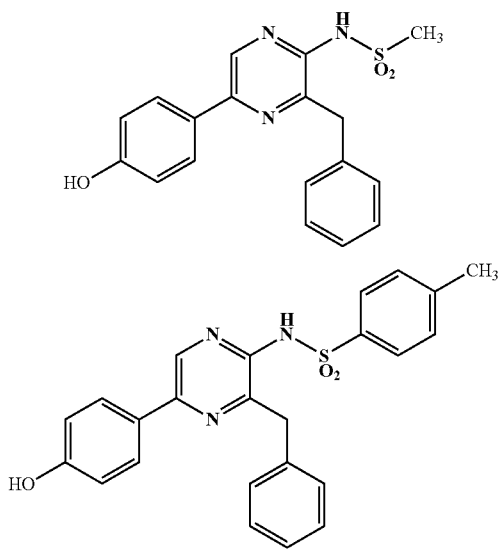
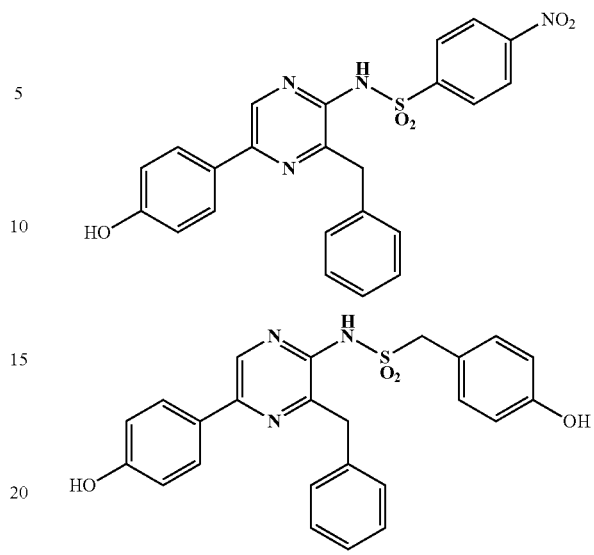
More preferably, the compound represented by general formula (2) is a compound selected from the group consisting of the compounds described below.
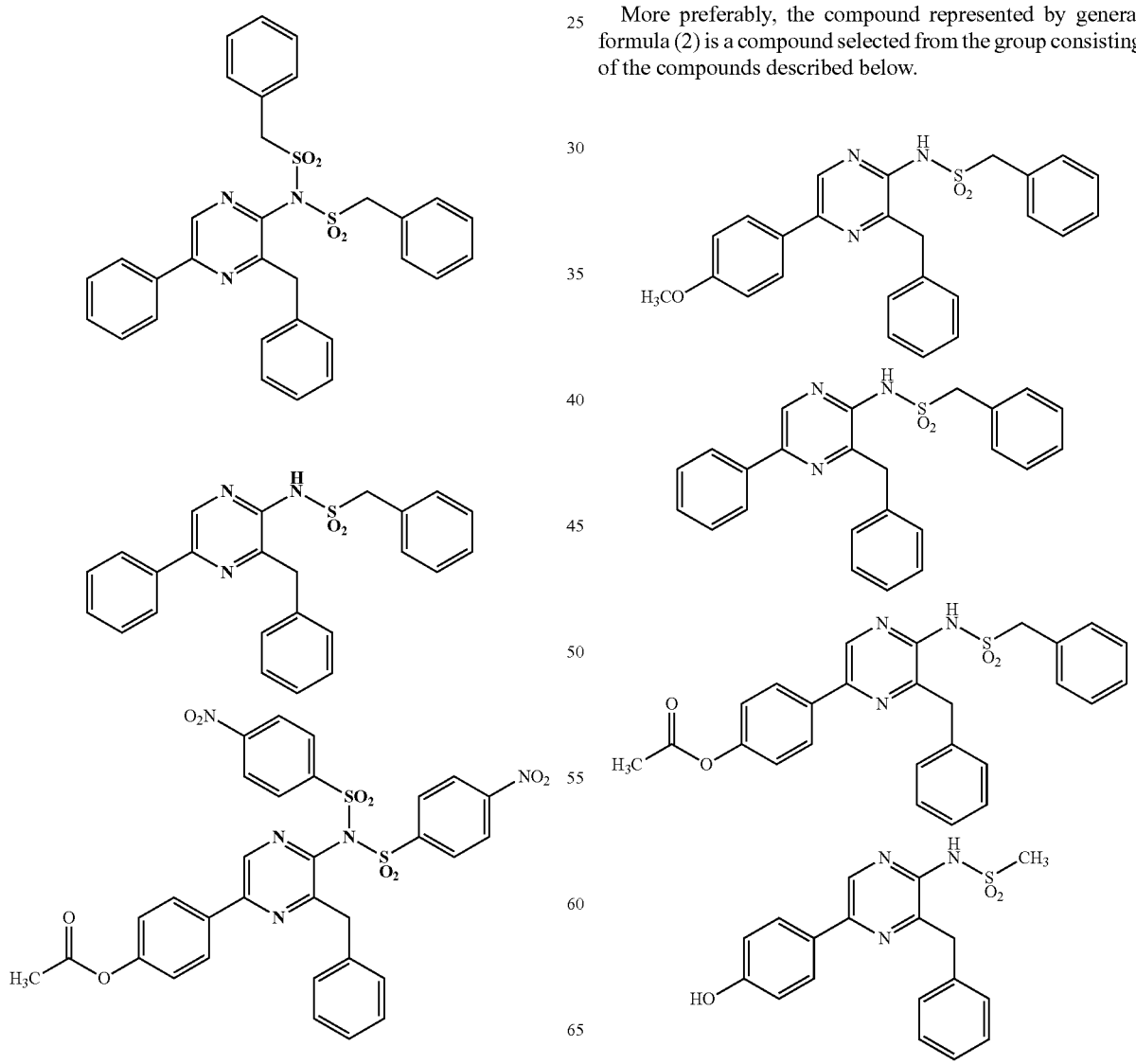

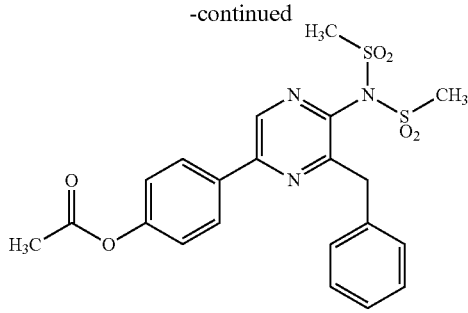

Most preferably, the compound represented by general formula (2) is a compound selected from the group consisting of the compounds described below.

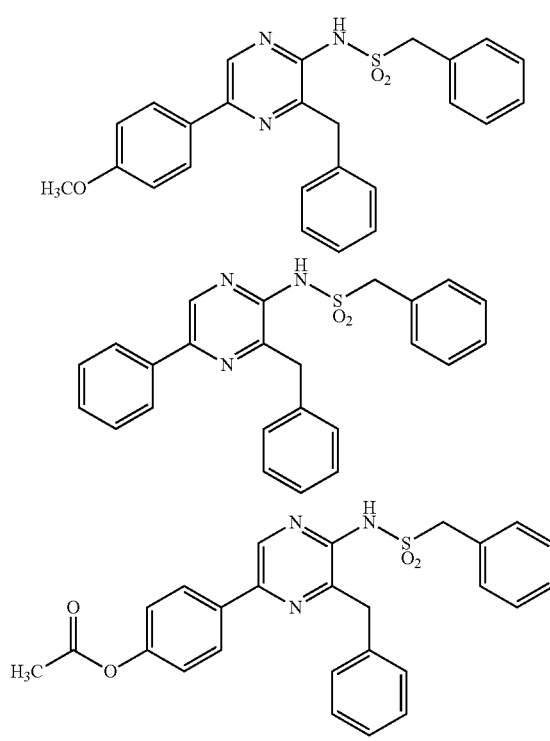

In another embodiment of the present invention, the compound represented by general formula (1) is a compound represented by general formula (3) described below (the thioamide-based coelenteramides of the present invention):

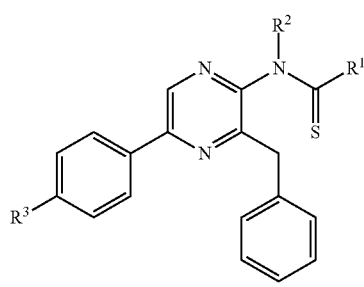

wherein $R^1$, $R^2$ and $R^3$ are the same as defined above.

Preferably, the compound represented by general formula (3) is a compound selected from the group consisting of the compounds described below.

More preferably, the compound represented by general formula (3) is a compound selected from the group consisting of the compounds described below.

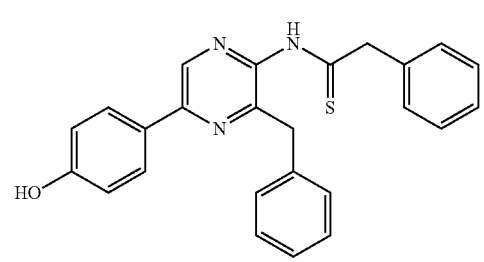

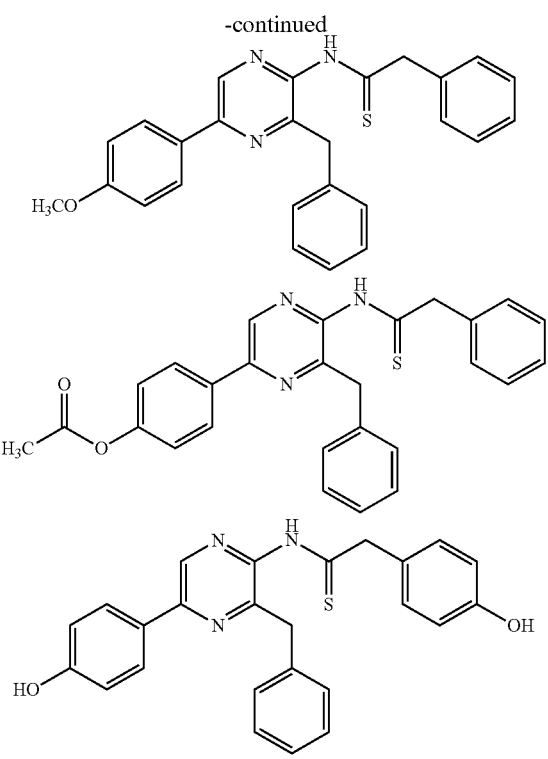

2. Process for Producing Coelenteramide Analogs
2.1. Process for Producing Sulfonamide-Based Coelenteramide Analogs A process for producing the sulfonamide-based coelenteramide represented by general formula (2) below among coelenteramide analogs of the present invention is described below:

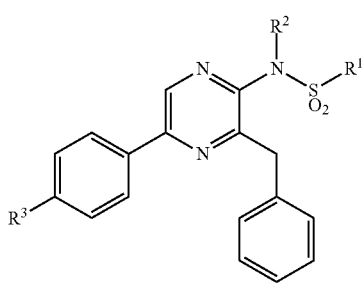

(2)

wherein $R^1$, $R^2$ and $R^3$ are the same as defined above.

The sulfonamide-based coelenteramide represented by general formula (2) can be produced, e.g., by reacting a compound represented by general formula (4):

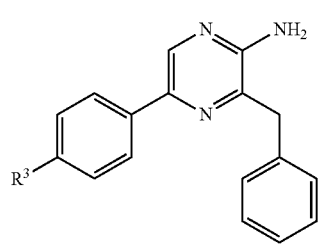

(4)

(wherein $R^3$ is the same as defined above) with a compound represented by general formula (5):

(5)

(wherein $R^1$ is the same as defined above).

The compound represented by general formula (4) can be produced by publicly known methods for production. The compound represented by general formula (4) can be produced, e.g., by the method described in Kishi, Y. et al., Tetrahedron Lett., 13, 2747-2748 (1972), or Adamczyk, M. et al., Org. Prep. Proced. Int., 33, 477-485 (2001), or by modifications of these methods. More specifically, the compound represented by general formula (4) can be produced as follows. That is, the compound can be produced either by first performing a cyclization reaction of a substituted phenylglyoxal aldoxime and a glycinonitrile derivative using a Lewis acid catalyst such as titanium tetrachloride, etc. to form a pyrazine oxide and then performing catalytic hydrogenation using Raney Ni, etc. as a catalyst, or by the Suzuki-Miyaura coupling of a 2-amino-5-bromopyrazine derivative and a substituted phenylboronic acid or a substituted phenylboronic acid pinacol ester.

The compound represented by general formula (5) may also be produced by publicly known methods for production, or is commercially available. Specifically, the compound can be produced, e.g., either by 1) reacting the corresponding substituted benzylsulfonic acid or its salt with an excess of thionyl chloride, heating the mixture under reflux and then concentrating under reduced pressure, or 2) reacting the corresponding substituted benzylsulfonic acid or its salt with oxalyl dichloride based on the corresponding carboxylic acid in a solvent such as dichloromethane in the presence of a catalytic amount of N,N-dimethylformamide (DMF) and then concentrating under reduced pressure, or 3) reacting a substituted benzyl Grignard reagent with sulfuryl chloride, or by modifications of these methods. Alternatively, benzylsulfonyl chloride can be purchased from Tokyo Chemical Industry Co., Ltd., Wako Pure Chemical Industries, Ltd., Kanto Chemical Co., Inc., etc.

Herein, the solvent used in the process for producing the compound represented by general formula (2) is not particularly limited and various solvents may be used, so long as they are other than aqueous solvent or alcohols. Examples are pyridine, dichloromethane, chloroform, acetonitrile, tetrahydrofuran, ethyl acetate, acetone, toluene, dioxane, ether, etc. These solvents may be used alone or in admixture.

In the process for producing the compound represented by general formula (2), the reaction temperature and reaction time are not particularly limited and are at −20° C. to 200° C. for 0.25 to 72 hours, preferably, −20° C. to 100° C. for 0.5 to 36 hours, and more preferably, 0° C. to 50° C. for 1 to 24 hours.

Furthermore, some of the compounds represented by general formula (2) wherein $R^2$ is H can be produced by subjecting the compound wherein $R^2$ is $SO_2R^1$, i.e., the disulfonic acid compound to alkaline hydrolysis and selectively cleaving one of the sulfonamide bonds or by its modifications.

2.2. Thioamide-Based Coelenteramide Analog

A process for producing the thioamide-based coelenteramide represented by general formula (3) below among coelenteramide analogs of the present invention is described below:

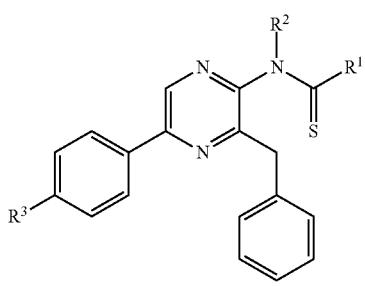
(3)

wherein $R^1$, $R^2$ and $R^3$ are the same as defined above

The thioamide-based coelenteramide represented by general formula (3) can be produced, e.g., by reacting a compound represented by general formula (6):

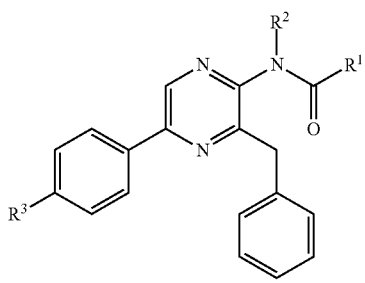
(6)

(wherein $R^1$, $R^2$ and $R^3$ are the same as defined above) with a Lawesson's reagent or phosphorus pentasulfide (tetraphosphorus decasulfide).

The compound represented by general formula (6) can be produced by publicly known methods for production. Specifically, the compound can be produced, e.g., by reacting the compound represented by general formula (4) and an acid halide represented by general formula (7) or an analog thereof:

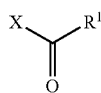
(7)

(wherein $R^1$ is the same as defined above, and X is a halogen (e.g., fluorine, chlorine, bromine or iodine) or $R^1C(=O)-$) either in an organic solvent in the presence of a base, or in a basic organic solvent, or by modifications thereof.

Herein, the solvent used in the process of producing the compound represented by general formula (3) is not particularly limited unless it is an aqueous solvent, an alcohol, a ketone and an ester. Examples of the solvent include toluene, benzene, dioxane, tetrahydrofuran, ether, dichloromethane, chloroform, pyridine and the like, which can be used alone or as an admixture thereof.

Further in the process of producing the compound represented by general formula (3), the reaction temperature and reaction time are not particularly limited and include, for example, 0° C. to 200° C. for 0.5 to 72 hours, preferably room temperature to 200° C. for 1 to 48 hours, and more preferably, 60° C. to 150° C. for 2 to 24 hours.

3. Fluorescent Protein

As shown in FIG. 1, blue fluorescent protein (BFP) can be produced by reacting coelenteramide or its analog with an apoprotein such as apoaequorin, etc. On the other hand, greenish fluorescent protein (gFP) can be produced by treating BFP with the chelating agent for removing calcium ions or divalent or trivalent ions substitutable for calcium ions.

3.1. Blue Fluorescent Protein (BFP)

3.1.1. Process for Producing Blue Fluorescent Protein (BFP)

The blue fluorescent protein (BFP) of the present invention is a complex in which coelenteramide analog of the present invention is coordinated to an apoprotein of a calcium-binding photoprotein. That is, a BFP of the present invention comprises coelenteramide analog of the invention, the apoprotein of a calcium-binding photoprotein and the divalent or trivalent ion substitutable for calcium ion a BFP can give fluorescence under the excitation of light and can also produce luminescence by bringing BFP into contact with coelenterazine or its analog.

According to the present invention, BFP is produced from coelenteramide analog of the present invention as follows. That is, coelenteramide analog of the present invention (e.g., the compound represented by general formula (1)) is reacted with the apoprotein of calcium-binding photoprotein in the presence of the divalent or trivalent ion substitutable for calcium ion to produce BFP.

Coelenteramide analog of the present invention used to produce BFP in the present invention is as described above. Coelenteramide analog of the present invention includes, for example, the compounds produced by the processes described above.

The divalent or trivalent ion substitutable for calcium ion, which is used to produce BFP in the present invention, refers to a divalent or trivalent ion that causes a luminescence reaction by reacting with a calcium-binding photoprotein in place of calcium ion. In other words, the divalent or trivalent ion has the function equivalent to calcium ion on the calcium-binding photoprotein. Examples of calcium ion or the divalent or trivalent ion substitutable for calcium ion include calcium ion ($Ca^{2+}$), magnesium ion ($Mg^{2+}$), strontium ion ($Sr^{2+}$), barium ion ($Ba^{2+}$), lead ion ($Pb^{2+}$), cobalt ion ($Co^{2+}$), nickel ion ($Ni^{2+}$), cadmium ion ($Cd^{2+}$), yttrium ion ($Y^{3+}$), lanthanum ion ($La^{3+}$), samarium ion ($Sm^{3+}$), europium ion ($Eu^{3+}$), dysprosium ion ($Dy^{3+}$), thulium ion ($Tm^{3+}$), ytterbium ion ($Yb^{3+}$) and the like. Among them, the divalent metal ions are preferred, more preferably the divalent metal ions rather than transition metals, e.g., $Ca^{2+}$, $Sr^{2+}$, $Pb^{2+}$, etc.

Examples of the apoprotein in the calcium-binding photoprotein used to produce BFP according to the present invention include apoaequorin, apoclytin-I, apoclytin-II, apobelin, apomitrocomin, apomineopsin, apobervoin, and the like. In some embodiments of the present invention, the apoprotein is apoaequorin, apoclytin-I, apoclytin-II, apomitrocomin, etc., e.g., apoaequorin. These apoproteins can be obtained from natural sources or genetically engineered. Furthermore, the amino acid sequence can be mutated from the natural sequence by gene recombination technology, as long as the apoproteins are capable of forming BFP.

The nucleotide sequences and amino acid sequences of the apoproteins of photoproteins obtained from the nature (natural apoproteins) are as follows. That is, the nucleotide sequence and amino acid sequence of natural apoaequorin are represented by SEQ ID NO: 1 and SEQ ID NO: 2. The nucleotide sequence and amino acid sequence of natural apoclytin-I are represented by SEQ ID NO: 3 and SEQ ID NO: 4. The nucleotide sequence and amino acid sequence of natural apoclytin-II are represented by SEQ ID NO: 5 and SEQ ID NO: 6. The nucleotide sequence and amino acid sequence of natural apomitrocomin are represented by SEQ ID NO: 7 and SEQ ID NO: 8. The nucleotide sequence and amino acid sequence of natural apobelin are represented by SEQ ID NO: 9 and SEQ ID NO: 10. The nucleotide sequence and amino acid sequence of natural apobervoin are represented by SEQ ID NO: 11 and SEQ ID NO: 12.

The apoprotein mutated by recombinant technology is a protein selected from the group consisting of (a) to (c) below:

(a) a protein comprising the amino acid sequence of natural apoprotein in which 1 or more amino acids are deleted, substituted, inserted and/or added, and having the activity or function of the apoprotein of a calcium-binding photoprotein;

(b) a protein comprising an amino acid sequence which is 90% or more homologous to the amino acid sequence of natural apoprotein, and having the activity or function of the apoprotein of a calcium-binding photoprotein; and, (c) a protein comprising an amino acid sequence encoded by a polynucleotide that hybridizes under stringent conditions to a polynucleotide comprising a nucleotide sequence complementary to the nucleotide sequence of natural apoprotein, and having the activity or function of the apoprotein of a calcium-binding photoprotein.

Examples of the "natural apoprotein" described above are apoaequorin, apoclytin-I, apoclytin-II, apobelin, apomitrocomin, apomineopsin, apobervoin, etc. In an embodiment of the present invention, the apoprotein is apoaequorin, apoclytin-I, apoclytin-II, apomitrocomin, etc., preferably apoaequorin. The amino acid sequences and nucleotide sequences of these natural apoproteins are as described above.

The "activity or function of the apoprotein in a calcium-binding photoprotein" means the activity or function that, e.g., a protein binds to the peroxide of coelenterazine or the peroxide of coelenterazine analog to produce the calcium-binding photoprotein. Specifically, "the protein binds to the peroxide of coelenterazine or the peroxide of coelenterazine analog to produce the calcium-binding photoprotein" not only means that (1) the protein binds to the peroxide of coelenterazine or the peroxide of coelenterazine analog to produce the photoprotein, but also means that (2) the protein is brought into contact with coelenterazine or its derivative in the presence of oxygen to produce a photoprotein (complex) comprising the protein and the peroxide of coelenterazine or the peroxide of coelenterazine analog. As used herein, the term "contact" means that the protein and coelenterazine or its analog are allowed to be present in the same reaction system, and includes, for example, the protein being added to a container charged with coelenterazine or its analog, coelenterazine or its analog being added to a container charged with the protein, the protein being mixed with coelenterazine or its analog, and the like. The "coelenterazine analog" refers to a compound capable of constituting a calcium-binding photoprotein such as aequorin, etc. together with the apoprotein, as in coelenterazine. Examples of coelenterazine or its analog include coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like. It is later described how these coelenterazines and analogs thereof are made available.

The range of "1 or more" in "the amino acid sequence in which 1 or more amino acids are deleted, substituted, inserted and/or added" is, for example, 1 to 20, 1 to 15, 1 to 10, 1 to 9, 1 to 8, 1 to 7, 1 to 6 (1 to several), 1 to 5, 1 to 4, 1 to 3, 1 to 2, and 1. In general, the less the number of amino acids deleted, substituted, inserted or added, the more preferable. In the deletion, substitution, insertion and addition of the amino acid residues described above, two or more may occur concurrently. Such domains can be acquired using site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

The range of "90% or more" in the "amino acid sequence which is 90% or more homologous" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. It is generally preferred for the numerical value indicating the degree of homology to be higher. The homology between amino acid sequences or nucleotide sequences can be determined using an analysis program such as BLAST (see, e.g., Altzchul, S. F. et al., J. Mol. Biol., 215, 403 (1990), etc.) or the like. When BLAST is used, the default parameters for the respective programs are employed.

The "polynucleotide that hybridizes under stringent conditions" refers to a polynucleotide (e.g., DNA) which is obtained by, for example, colony hybridization, plaque hybridization or Southern hybridization using as the probe a polynucleotide consisting of a nucleotide sequence complementary to the nucleotide sequence of natural apoprotein or all or part of the polynucleotide encoding the amino acid sequence of natural apoprotein. Specific examples include a polynucleotide which can be identified by performing hybridization at 65° C. in the presence of 0.7 to 1.0 mol/L NaCl using a filter on which the polynucleotide from the colony or plaque is immobilized, then washing the filter at 65° C. with 0.1- to 2-fold SSC (saline-sodium citrate) solution (a 1-fold SSC solution is composed of 150 mmol/L sodium chloride and 15 mmol/L sodium citrate).

Hybridization may be performed in accordance with modifications of the methods described in textbooks, e.g., Sambrook, J. et al.: Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc.

As used herein, "stringent conditions" may refer to less stringent conditions, moderately stringent conditions and highly stringent conditions. The "less stringent conditions" are, for example, the conditions under 5×SSC, 5×Denhardt's solution, 0.5% (w/v) SDS and 50% (v/v) formamide at 32° C. The "moderately stringent conditions" are, for example, the conditions under 5×SSC, 5×Denhardt's solution, 0.5% (w/v) SDS and 50% (v/v) formamide at 42° C. The "highly stringent conditions" are, for example, the conditions under 5×SSC, 5×Denhardt's solution, 0.5% (w/v) SDS and 50% (v/v) formamide at 50° C. The more stringent the conditions are, the higher the complementarity required for double strand formation. Specifically, for example, under these conditions, a polynucleotide (e.g., DNA) of higher homology is expected to be obtained efficiently at higher temperatures, although multiple factors are involved in hybridization stringency, including temperature, probe concentration, probe length, ionic strength, time and base concentration; those skilled in the art may appropriately choose these factors to realize a similar stringency.

Where a kit commercially available is used for the hybridization, for example, AlkPhos Direct Labeling Reagents (manufactured by Amersham Pharmacia) may be used. In this case, incubation with a labeled probe is performed overnight in accordance with the protocol attached to the kit, the membrane is then washed with a primary wash buffer containing 0.1% (w/v) SDS at 55° C., and finally the hybridized DNA can be detected.

Other hybridizable polynucleotides include, as calculated by an analysis program such as BLAST or the like using the default parameters, DNAs having a homology of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide encoding the amino acid sequence of the apoprotein. The homology of amino acid sequences or nucleotide sequences can be determined using the method described above.

The recombinant apoprotein which can be used in the present invention includes, for example, recombinant aequorin described in Shimomura, O. and Inouye, S. Protein Express. Purif (1999) 16: 91-95, recombinant clytin-I described in Inouye, S. and Sahara, Y. Protein Express. Purif (2007) 53: 384-389, recombinant clytin-II described in Inouye, S. J. Biochem. (2008) 143: 711-717, and the like.

In some embodiments of the present invention, all cysteine residues in the apoprotein are substituted with serine residues. When free SH groups of the cysteine residues in the apoprotein are oxidized to form S—S bonds, BFP loses luminescent activity. Thus, the apoprotein in which the cysteine residues are substituted with serine residues to disable the ability to form S—S bonds does not lose a great deal of the luminescent activity but continues to keep the activity because of the failure to form S—S bonds.

The amount of coelenteramide analog of the present invention used to produce BFP is not particularly limited and is in a range of, e.g., 1 mol to 5 mol, preferably 1 mol to 2 mol, more preferably 1 mol to 1.2 mol, based on 1 mol of the apoprotein.

In the production of BFP, the reaction of coelenteramide analog of the present invention and the apoprotein with calcium ion or divalent or trivalent ion substitutable for calcium ion is preferably performed in the presence of a reducing agent. Examples of the reducing agent as used herein include dithiothreitol (DTT), mercaptoethanol, etc. The amount of the reducing agent used to produce BFP is not particularly limited so long as the amount does not affect the regeneration of BFP. Preferably, the reducing agent is in a concentration sufficient to prevent the formation of S—S bonds among three cysteine residues in the apoaequorin. Such a concentration is, for example, 1 mM dithiothreitol or 0.1% (v/v) mercaptoethanol in a final concentration.

In the process for producing BFP, the reaction temperature and time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

Thus, BFP obtained can be further purified. Purification of BFP may be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination thereof 3.1.2. Application of Blue Fluorescent Protein (BFP)

(1) Use as Luminescent Catalyst

BFP of the present invention acts on a luminescence substrate to produce light and can thus be used as a luminescent catalyst. Accordingly, the present invention provides a luminescence method, which comprises contacting coelenterazine or its analog with BFP of the present invention. As used herein, the term "contact" means that BFP and coelenterazine or its analog are allowed to be present in the same reaction system and includes, for example, BFP being added to a container charged with coelenterazine or its analog, coelenterazine or its analog being added to a container charged with BFP, BFP being mixed with coelenterazine or its analog, and the like.

The luminescence substrate used for the light-emitting method of the present invention includes, for example, coelenterazine or its analog. The "coelenterazine analog" refers to a compound capable of constituting a calcium-binding photoprotein such as aequorin, etc. together with the apoprotein, as in coelenterazine. Examples of coelenterazine or its analog used as the luminescence substrate include coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like, preferably coelenterazine, h-coelenterazine and e-coelenterazine. These coelenterazine and analogs thereof can be produced by the method described in, e.g., Shimomura et al. (1988) Biochem. J. 251, 405-410, Shimomura et al. (1989) Biochem. J. 261, 913-920, or Shimomura et al. (1990) Biochem. J. 270, 309-312, or modifications thereof. Alternatively, they are commercially available from Chisso Corporation, Wako Pure Chemical Industries, Promega Inc., etc. and these commercial products may also be used for the light-emitting method of the present invention.

When these coelenterazine and analogs thereof are brought into contact with BFP, light is produced upon the oxidation of coelenterazine or analogs thereof into their corresponding coelenteramide or analogs thereof by the catalytic reaction of the contacted BFP (whereby carbon dioxide is released). The emission time of luminescence is generally 0.5 to 3 hours. However, the emission time can be more prolonged or the emission time can be further shortened, depending upon the conditions chosen.

(2) Use as Reporter Protein

BFP of the present invention may also be used as a reporter protein to determine the transcription activity of a promoter, etc. A polynucleotide encoding an apoprotein is fused to a target promoter or other expression control sequence (e.g., an enhancer, etc.) to construct a vector. The vector is transformed to a host cell. Coelenteramide analog of the present invention and calcium ion or divalent or trivalent ion substitutable for calcium ion are brought into contact with the transformant. By detecting the fluorescence from the fluorescent protein of the present invention, the activity of the target promoter or other expression control sequence can be determined. As used herein, the term "contact" means that a host cell and coelenteramide analog as well as calcium ions or divalent or trivalent ions substitutable for calcium ions are allowed to be present in the same culture system or reaction system, and includes, for example, coelenteramide analog and calcium ions or divalent or trivalent ions substitutable for calcium ions being added to a culture container charged with a host cell, a host cell being mixed with coelenteramide analog and calcium ions or divalent or trivalent ions substitutable for calcium ions, a host cell being cultured in the presence of coelenteramide analog and calcium ions or divalent or trivalent ions substitutable for calcium ions, and the like.

(3) Use as Detection Marker

BFP of the present invention can be used as a detection marker with its fluorescence. The detection marker of the present invention can be used to detect a target substance in, e.g., immunoassay, hybridization assay, etc. BFP of the present invention can be used in the form bound to a target substance (protein, nucleic acid, etc.) by methods conventionally used, such as chemical modifications. Detection using such a detection marker may be performed in a conventional manner.

The detection marker of the invention may also be used to determine distribution of the target substance described above, for example, by expressing the marker as a fused protein of an apoprotein with the target substance, then inserting the fused protein into a cell by a technique such as microinjection, and contacting the protein with coelenteramide analog of the invention and calcium ions or divalent or trivalent ions substitutable for calcium ions. As used herein, the term "contact" means that a cell and coelenteramide analog as well as calcium ions or divalent or trivalent ions substitutable for calcium ions are allowed to be present in the same culture system or reaction system, and includes, for example, coelenteramide analog and calcium ions or divalent or trivalent ions substitutable for calcium ions being added to a culture container charged with a cell, a cell being mixed with coelenteramide analog and calcium ions or divalent or trivalent ions substitutable for calcium ions, a host cell being cultured in the presence of coelenteramide analog and calcium ions or divalent or trivalent ions substitutable for calcium ions, and the like.

Measurement of the distribution of such a target substance, etc. may also be performed by using a detection method such as luminescence imaging. Aside from the transformation to a cell by a technique such as microinjection, the apoprotein may also be used after expression in a cell.

(4) Material for Amusement Supplies

BFP of the present invention generates fluorescence under the excitation of light. Therefore, BFP of the present invention can be advantageously used as a fluorescence material for amusement supplies. Examples of such amusement supplies are fluorescent soap bubbles, fluorescent ice bars, fluorescent candies, fluorescent color paints, etc. The amusement supplies of the invention can be prepared in a conventional manner.

3.2. Greenish Fluorescent Protein (gFP)

3.2.1. Production of Greenish Fluorescent Protein (gFP)

The greenish fluorescent protein (gFP) of the present invention is a complex in which coelenteramide analog of the present invention is coordinated to the apoprotein of a calcium-binding photoprotein. That is, the gFP of the present invention comprises coelenteramide analog of the invention and the apoprotein of a calcium binding photoprotein. The gFP can generate fluorescence under the excitation of light.

The gFP of the present invention is produced by removing from BFP described above calcium ions or divalent or trivalent ions substitutable for calcium ions. Calcium ions or divalent or trivalent ions substitutable for calcium ions can be removed from BFP by treating the chelating agent for calcium ions or divalent or trivalent ions substitutable for calcium ions.

In the present invention, the chelating agent used to produce gFP can be any ones and is not particularly limited, so long as it strongly binds to calcium ions or divalent or trivalent ions substitutable for calcium ions. Examples of the chelating agent include ethylenediaminetetraacetic acid (EDTA), ethylene glycol-bis(β-aminoethyl ether)-N,N,N',N'-tetraacetic acid (EGTA), trans-1,2-diaminocyclohexane-N,N,N',N'-tetraacetic acid (CyDTA), N-(2-hydroxyethyl)iminodiacetic acid (HIDA) and the like. Herein, the divalent or trivalent ions substitutable for calcium ions are the same as described above.

The amount of the chelating agent used to produce the gFP is not particularly limited unless its concentration affects regeneration of the gFP. Since it is demonstrated that 3 mol of calcium ions bind to 1 mol of ion apoaequorin, the amount of, e.g., 3 mol or more is preferred.

In the process for producing the gFP, the reaction temperature and reaction time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

The thus produced gFP may be further purified. Purification of the gFP may be performed by conventional methods for separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination thereof 3.2.2 Use of Greenish Fluorescent Protein (gFP)

(1) Use as Reporter Protein

The gFP of the present invention may also be used as a reporter protein to determine the transcription activity of a promoter, etc. A polynucleotide encoding an apoprotein is fused to a target promoter or other expression control sequence (e.g., an enhancer, etc.) to construct a vector. The vector is transformed to a host cell. Coelenteramide analog of the present invention is brought into contact with the transformant to form BFP. Then, the chelating agent for removing calcium ions or divalent or trivalent ions substitutable for calcium ions is brought into contact thereto to form gFP. By detecting the fluorescence intensity from the gFP of the present invention, the activity of the target promoter or other expression control sequence can be determined.

(2) Use as Detection Marker

The gFP of the present invention can be used as a detection marker with its fluorescence. The detection marker of the present invention can be used to detect a target substance in, e.g., immunoassay, hybridization assay, etc. The gFP of the present invention can be used in the form bound to a target substance (protein, nucleic acid, etc.) by methods conventionally used, such as chemical modification. Detection using such a detection marker can be carried out in a conventional manner. The detection marker of the invention may also be used to determine the distribution of a target substance, for example, by expressing the marker as a fused protein of an apoprotein with the target substance, then inserting the fused protein into a cell by a technique such as microinjection, and contacting the protein with coelenteramide analog of the invention to produce BFP, then contacting with the chelating agent for removing calcium ions or divalent or trivalent ions substitutable for calcium ions to produce the gFP. Measurement of the distribution of such a target substance may also be performed by using a detection method such as luminescence imaging, etc. Aside from the transformation to a cell by a technique such as microinjection, the apoprotein may also be used after expression in a cell.

(3) Material for Amusement Supplies

The gFP of the present invention can be advantageously used as a fluorescence material for amusement supplies. Examples of such amusement supplies are fluorescent soap bubbles, fluorescent ice bars, fluorescent candies, fluorescent color paints, etc. The amusement supplies of the invention can be prepared in a conventional manner.

4. Calcium-Binding Photoprotein

As shown in FIG. 1, the calcium-binding photoproteins such as aequorin, etc. can be produced by reacting gFP with coelenterazine or its analog in the presence of the chelating agent for calcium ions or divalent or trivalent ions substitutable for removing calcium ions such as EDTA, etc.

4.1. Production of Calcium-Binding Photoprotein

The calcium-binding photoprotein of the invention can be produced from the gFP of the present invention. That is, the calcium-binding photoprotein of the invention can be obtained by reacting gFP with coelenterazine or its analog as a luminescence substrate.

The reaction of gFP with coelenterazine or its analog is carried out by contacting gFP with coelenterazine or its analog. As used herein, the term "contact" means that the gFP of the invention and coelenterazine or its analog are allowed to be present in the same reaction system, and includes, for example, the gFP of the invention being added to a container containing coelenterazine or its analog, coelenterazine or its analog of the invention being added to a container containing the gFP of the invention, the gFP of the invention being mixed with coelenterazine or its analog, and the like.

Examples of coelenterazine or its analog used to produce the calcium-binding photoprotein of the invention include coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like, preferably coelenterazine, h-coelenterazine and e-coelenterazine. It is described above how to obtain these coelenterazines and analogs thereof.

The amount of coelenterazine or its analog used to produce the calcium-binding photoprotein is not particularly limited and may be, e.g., 1.2 mol or more, based on 1 mol of gFP.

In the process for producing the calcium-binding photoprotein, the reaction temperature and time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

The reaction of the fluorescent protein with coelenterazine or its analog is carried out preferably in the presence of the chelating agent for removing calcium ions or divalent or trivalent ions substitutable for calcium ions. The chelating agent used to produce the gFP in the present invention is the same as described above.

In a more preferred embodiment of the present invention, the reaction of the fluorescent protein and coelenterazine or its analog is carried out in the presence of a reducing agent. Examples of the reducing agent used herein include dithiothreitol (DTT), mercaptoethanol, etc. The amount of the reducing agent used to produce the calcium binding photoprotein is not particularly limited so long as the amount does not affect the regeneration. Preferably, the reducing agent is in a concentration sufficient to prevent the formation of S—S bonds by the presence of cysteine residues at the three positions of apoaequorin. Such a concentration is, for example, 1 mM dithiothreitol or 0.1% (v/v) mercaptoethanol in a final concentration.

4.2. Use of Calcium-Binding Photoprotein (1) Detection or Quantitative Determination of Calcium Ions The calcium-binding photoprotein of the invention is a photoprotein (holoprotein) which emits light by the action of calcium ions. Thus, the photoprotein of the invention can be used for the detection or quantitative determination of calcium ions.

For the detection or quantitative determination of calcium ions, the photoprotein consisting of an apoprotein and the peroxide of coelenterazine analog is used. The photoprotein can be produced according to the process described above. The detection or quantitative determination of calcium ions may be performed by adding a sample solution directly to a solution of the photoprotein and measuring the luminescence generated. Alternatively, calcium ions may also be detected or quantified by adding a solution of the photoprotein to a sample solution and measuring the luminescence generated.

The detection or quantification of calcium ions may be performed by measuring the luminescence of the photoprotein of the invention through the action of calcium ions, using a luminometer. Luminometers which may be used include commercially available instruments, such as a Centro LB 960 (manufactured by Berthold, Inc.). The concentration of calcium ion can be quantitatively determined by preparing a luminescence standard curve for known calcium ion concentrations using the photoprotein.

(2) Bioluminescence Resonance Energy Transfer (BRET) Method

The calcium-binding photoprotein of the present invention can be used for analyses, including an analysis of biological functions, an assay for enzyme activity, etc., based on the principle of intermolecular interactions by the bioluminescence resonance energy transfer (BRET) method.

For example, using the photoprotein of the invention as a donor protein and an organic compound or a fluorescent protein as an acceptor protein, the interactions between the proteins can be detected by causing bioluminescence resonance energy transfer (BRET) between them. In an embodiment of the present invention, the organic compound used as an acceptor protein is Hoechst 3342, Indo-1, DAP1, etc. In another embodiment of the present invention, the fluorescent protein used as an acceptor protein is a greenish fluorescent protein (GFP), a blue fluorescent protein (BFP), a mutant GFP fluorescent protein, phycobilin, etc. In a preferred embodiment of the present invention, the physiological functions to be analyzed include an orphan receptor (in particular, a G-protein conjugated receptor), apoptosis, transcription regulation by gene expression, etc. In a more preferred embodiment of the present invention, the enzyme to be analyzed is protease, esterase, kinase, or the like.

Analysis of the physiological functions by the BRET method may be performed by publicly known methods, for example, by modifications of the methods described in Biochem. J. 2005, 385, 625-637, Expert Opin. Ther Tarets, 2007 11: 541-556, etc. Assay for the enzyme activity may be performed by publicly known methods, for example, by modifications of the methods described in Nat Methods 2006, 3:165-174, Biotechnol J. 2008, 3:311-324, etc.

All literatures and publications mentioned in this specification are herein incorporated in their entirety by reference into the specification, irrespective of their purposes. The specification includes all of the contents as disclosed in the claims, specification and drawings of Japanese Patent Application No. 2009-27904 (filed Feb. 9, 2009), based on which the priority of the present application is enjoyed.

The objects, characteristics, and advantages of the present invention as well as the idea thereof are apparent to those skilled in the art from the descriptions given herein, and those skilled in the art can easily implement the present invention. It is to be understood that the best mode to carry out the invention and specific examples are to be taken as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

1. Overview

Based on the basic skeleton of CTMD, h-coelenterathioamide and h-coelenterasulfonamide were synthesized by the synthesis scheme described below. For comparison, h-coelenteramide was also synthesized.

<h-Coelenterathioamide and h-Coelenterasulfonamide>

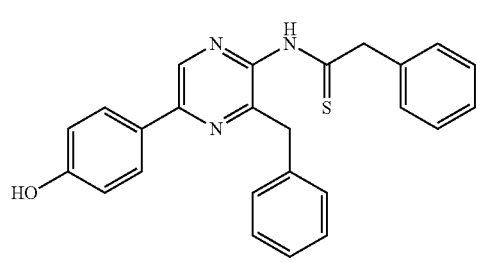

(c-14)

h-Coelenterathioamide

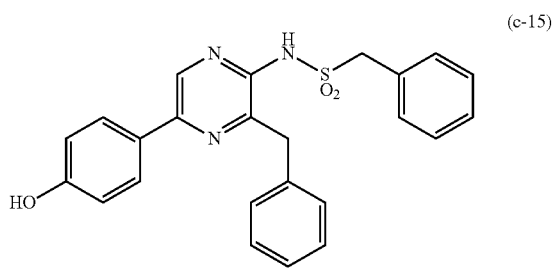

(c-15)

h-Coelenterasulfonamide

<h-Coelenteramide>

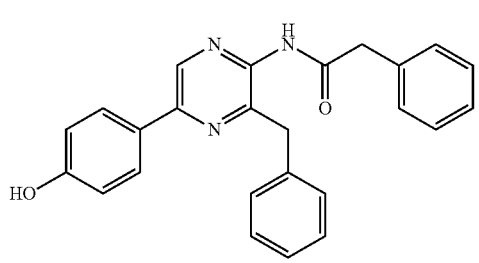

(c-13)

h-Coelenteramide

<Synthetic Routes>

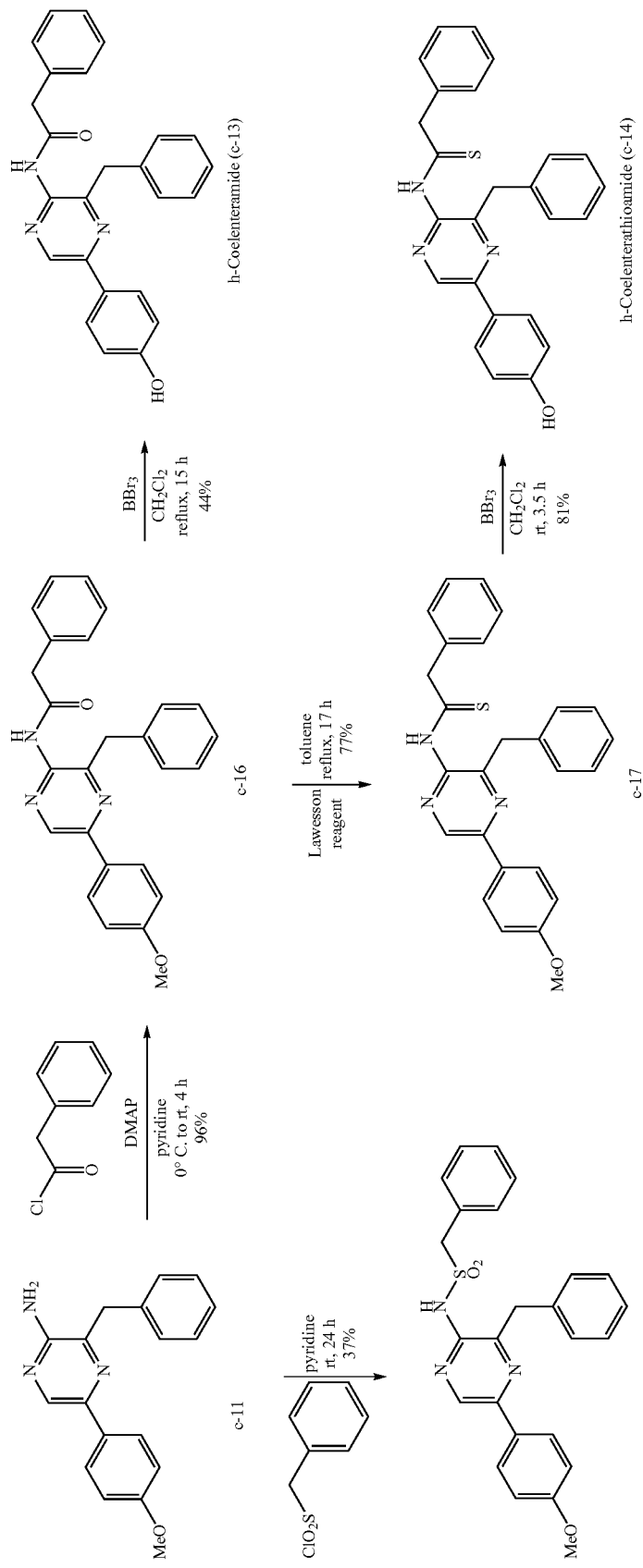

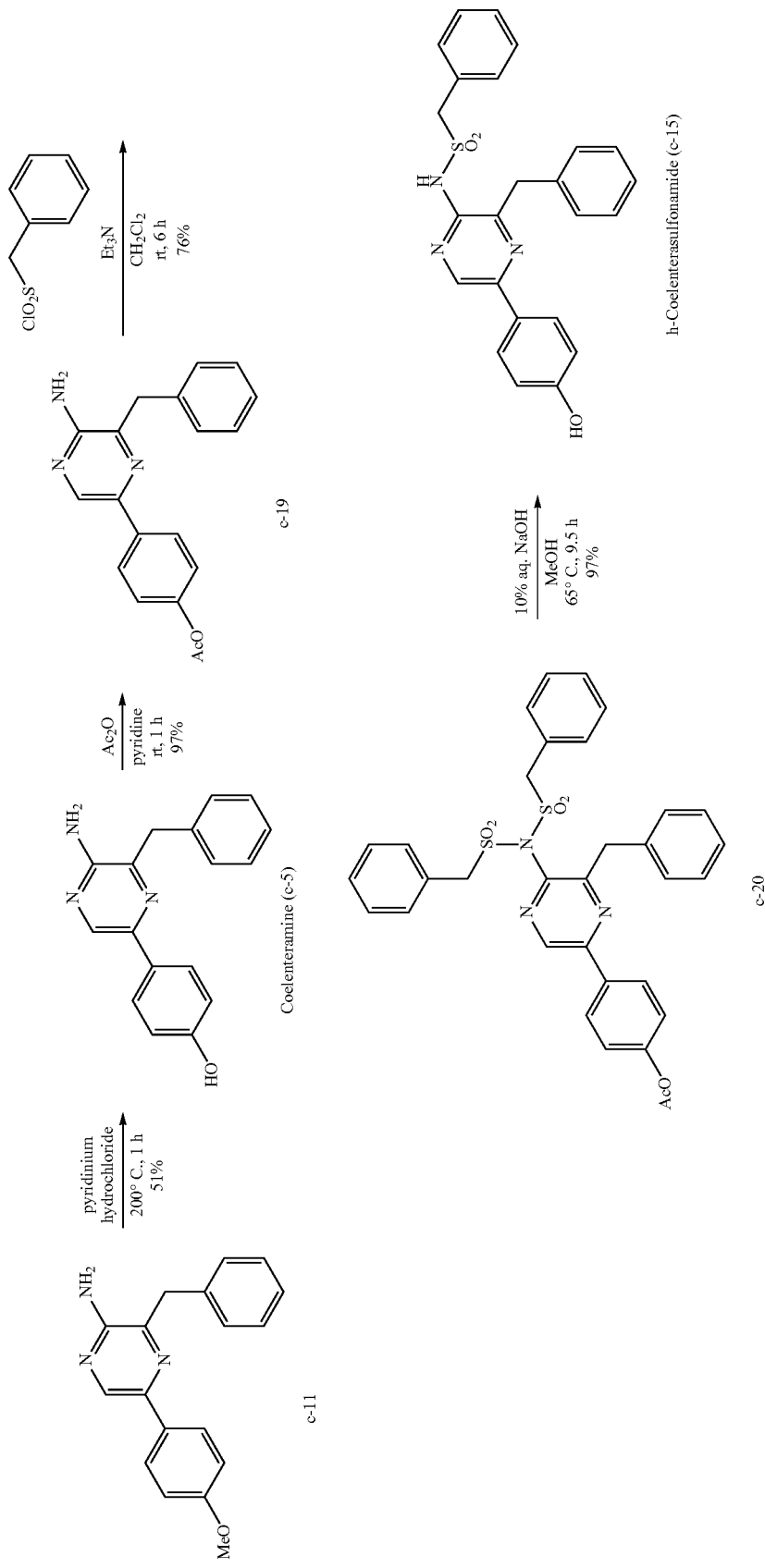

Furthermore, various CTMD derivatives were synthesized by the following process of synthesis, using h-coelenterathioamide, h-coelenterasulfonamide and h-coelenteramide.
<CTMD Derivatives>
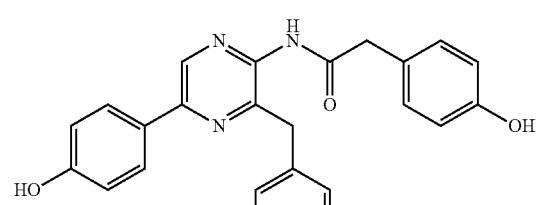
Coelenteramide
(c-4)
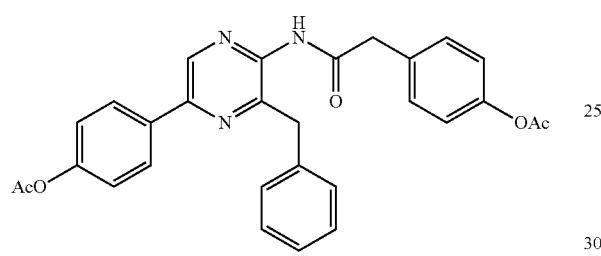
c-29
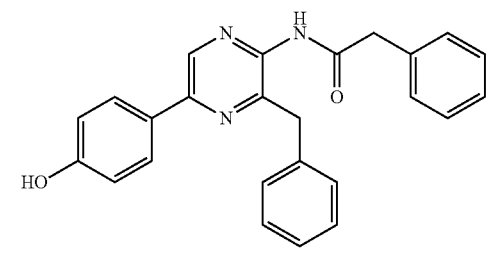
(c-13)
h-Coelenteramide
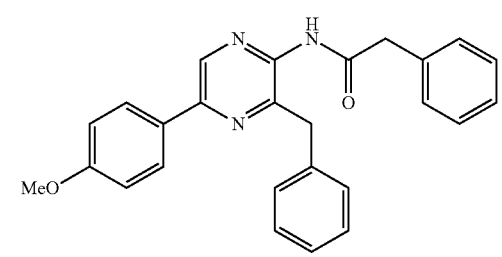
c-16
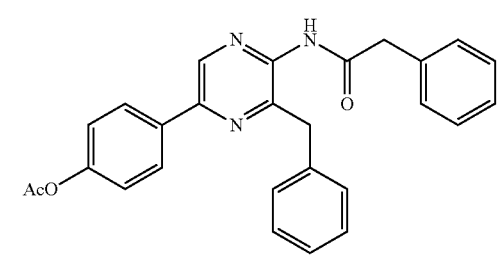
c-30
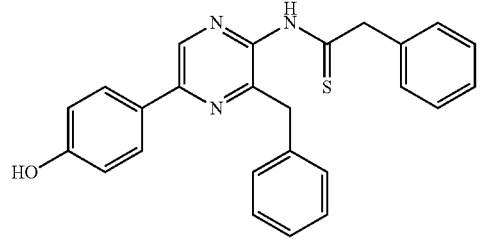
(c-14)
h-Coelenterathioamide
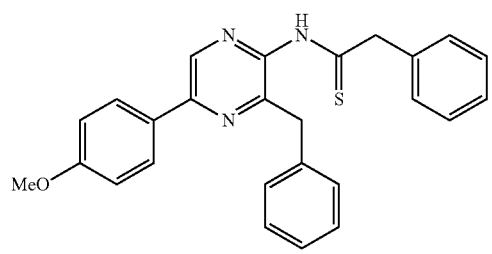
c-17
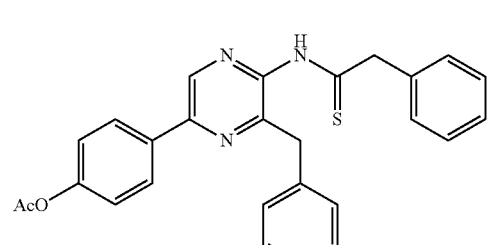
c-31
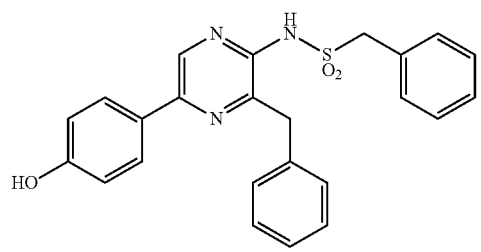
(c-15)
h-Coelenterasulfonamide
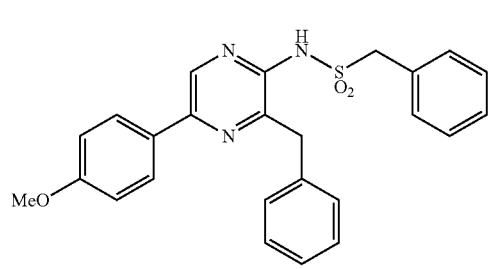
c-18
c-32

-continued
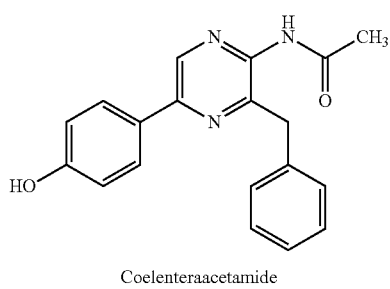
Coelenteraacetamide (c-25)
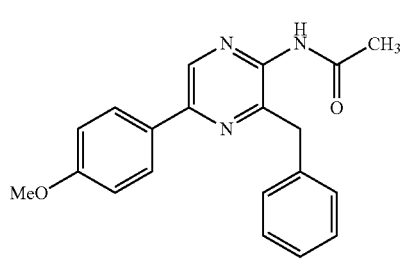
c-24
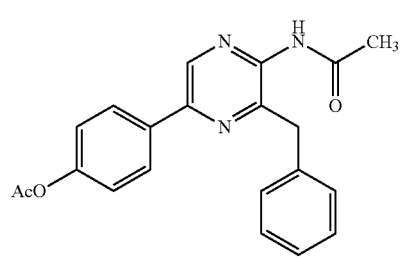
c-33
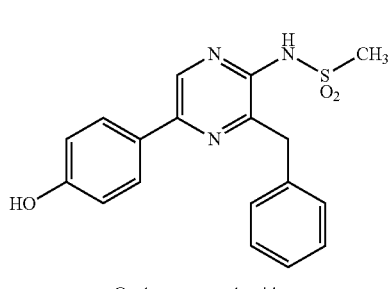
Coelenteramesylamide (c-34)
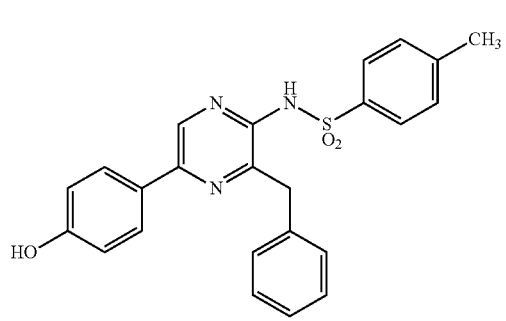
Coelentera-p-tosylamide (c-35)
-continued
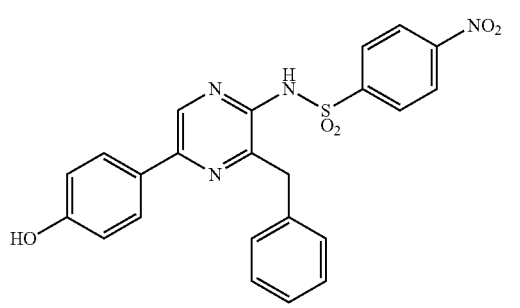
Coelentera-p-nosylamide (c-36)
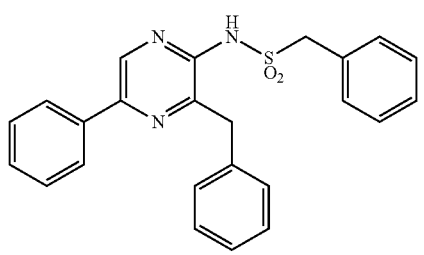
Dideoxycoelenterasulfonamide (c-37)
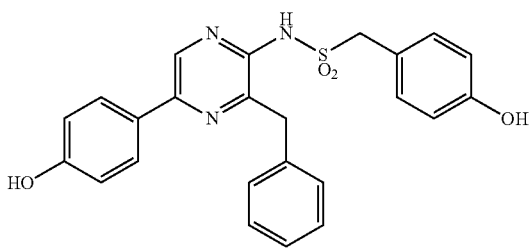
Coelenterasulfonamide (c-38)
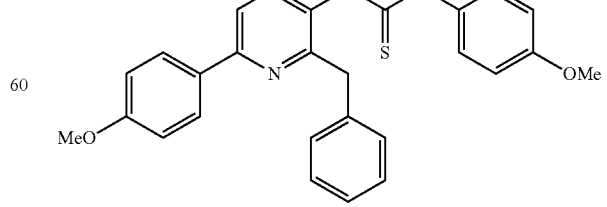
c-48
c-44

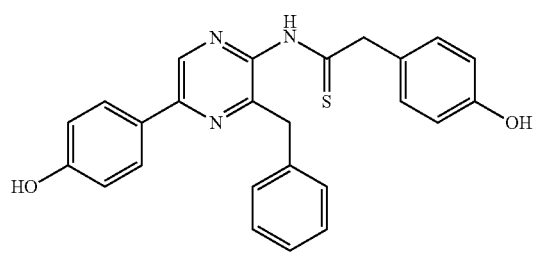
Coelenterathioamide (c-45)
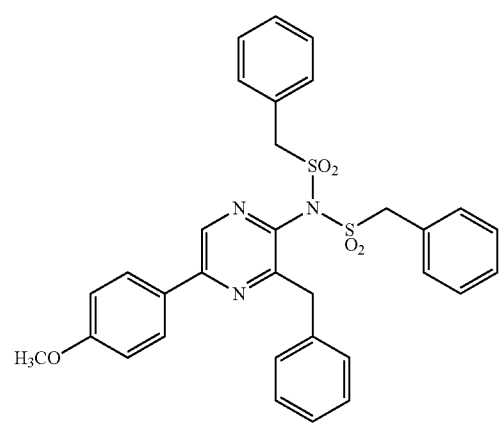
(c-21)
(c-20)
(c-39)
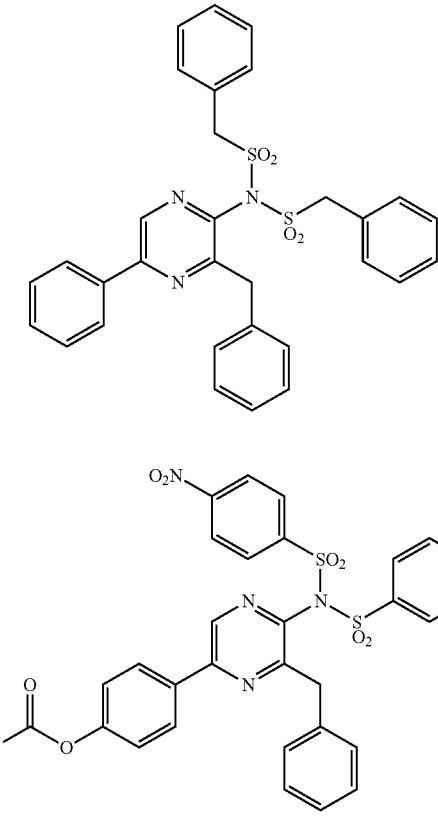
c-42
c-40
<Process for Synthesis of CTMD Derivatives>
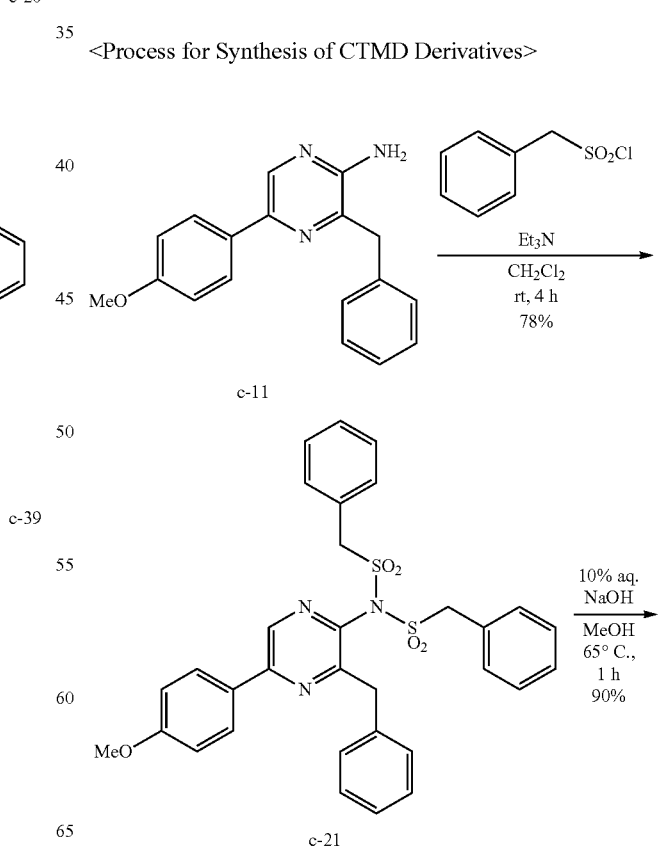

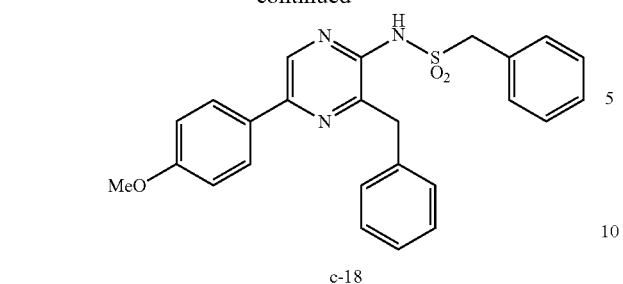
c-18
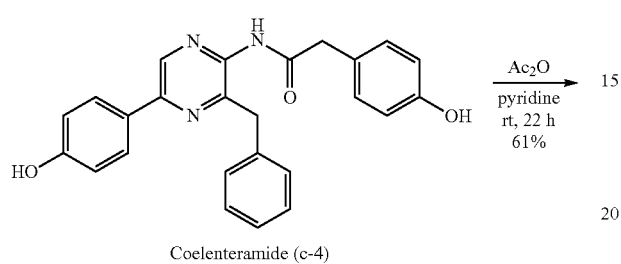
Coelenteramide (c-4)
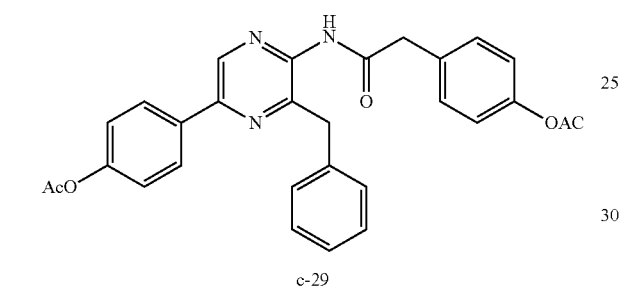
c-29
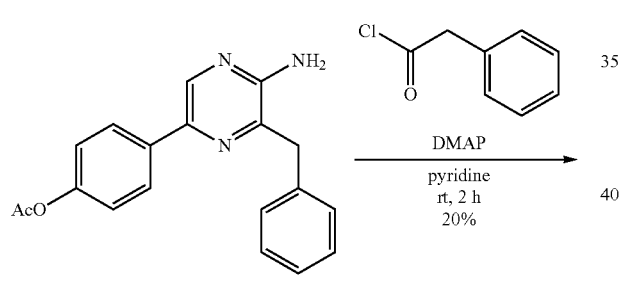
c-19
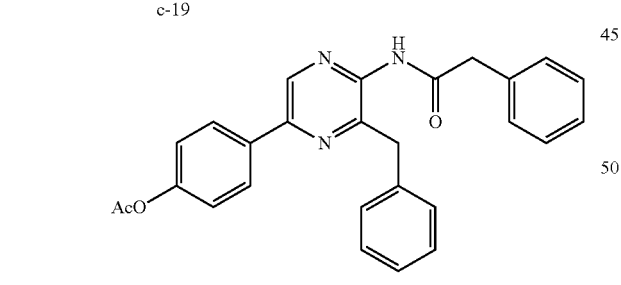
c-30
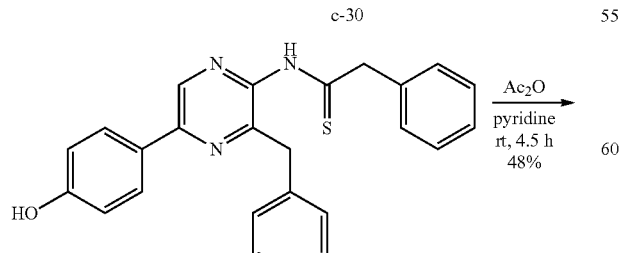
h-Coelenterathioamide (c-14)
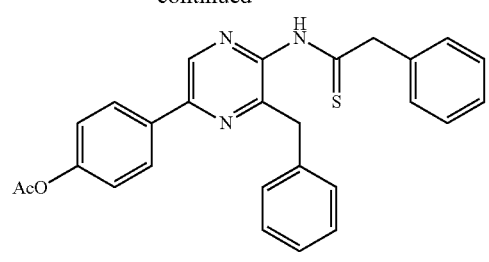
c-31
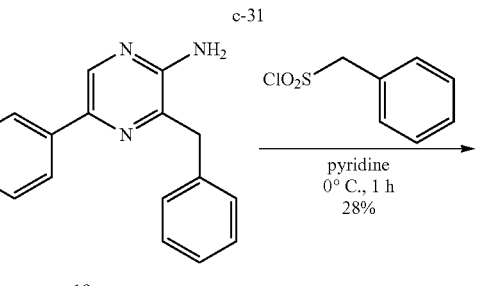
c-19
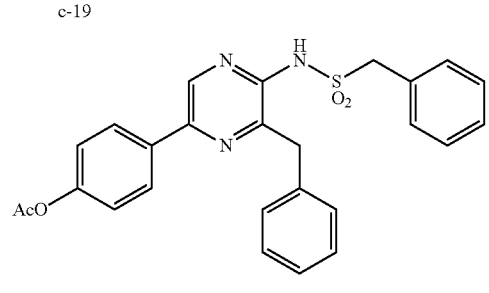
c-32
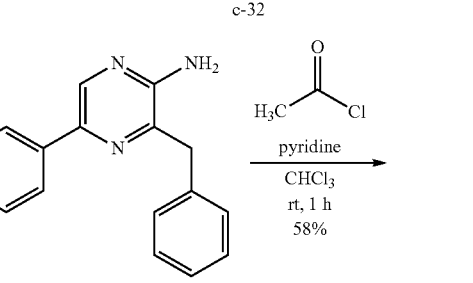
Coelenteramine (c-5)
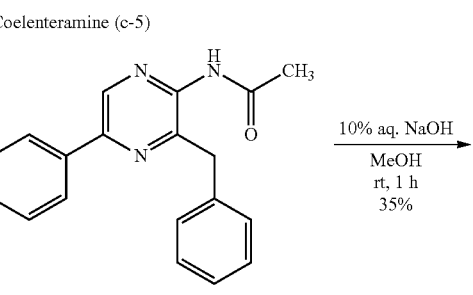
c-33
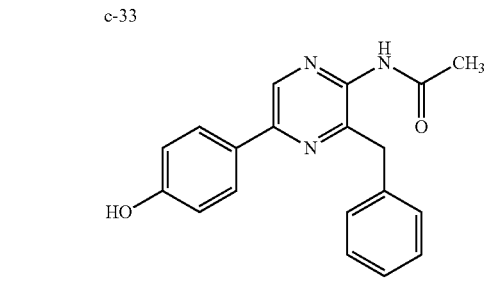
Coelenteracetamide (c-25)

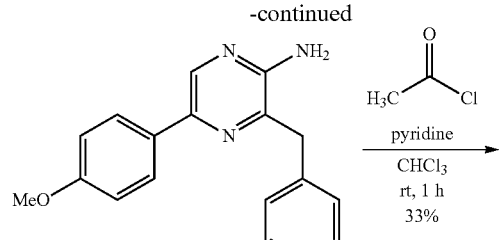
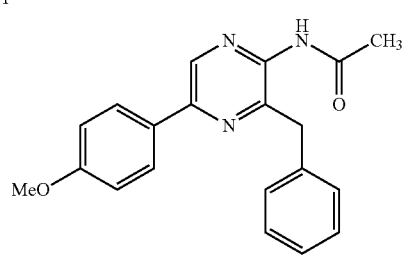
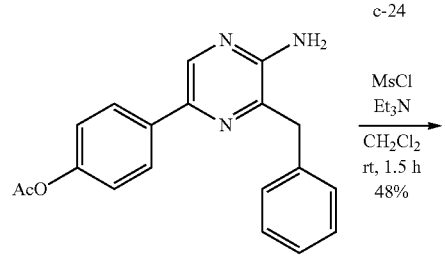
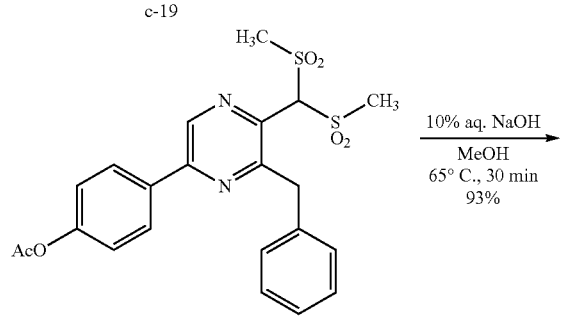
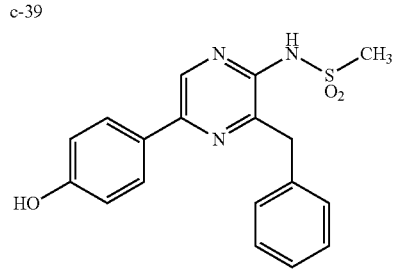
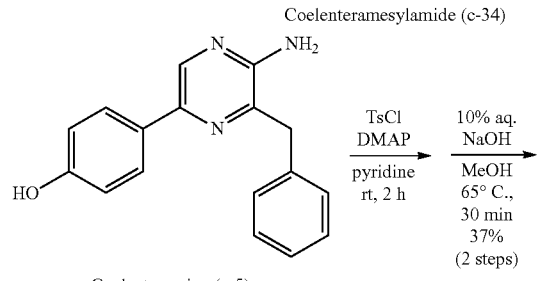
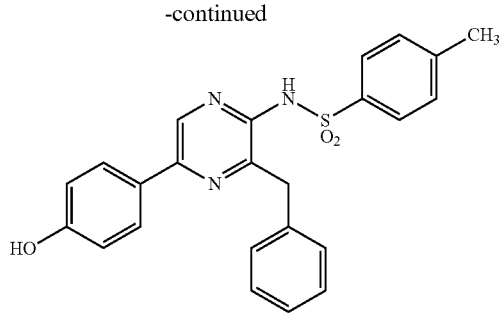
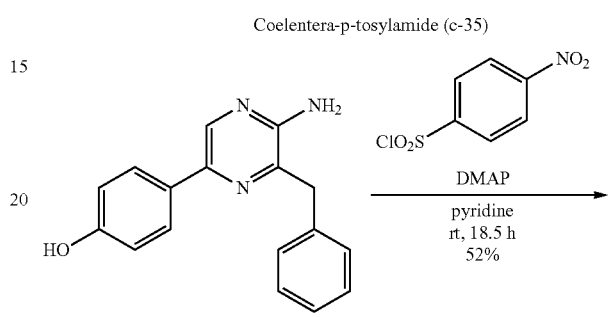
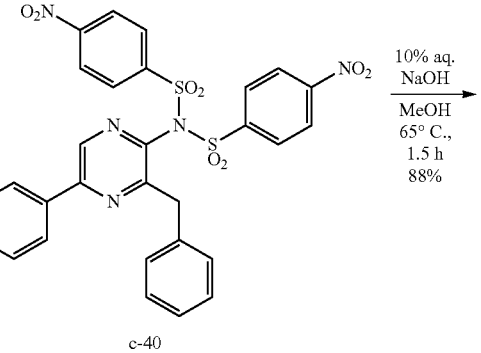
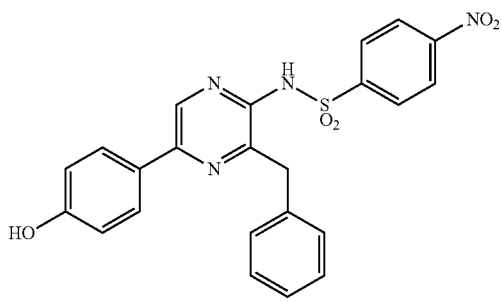
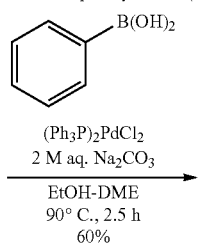

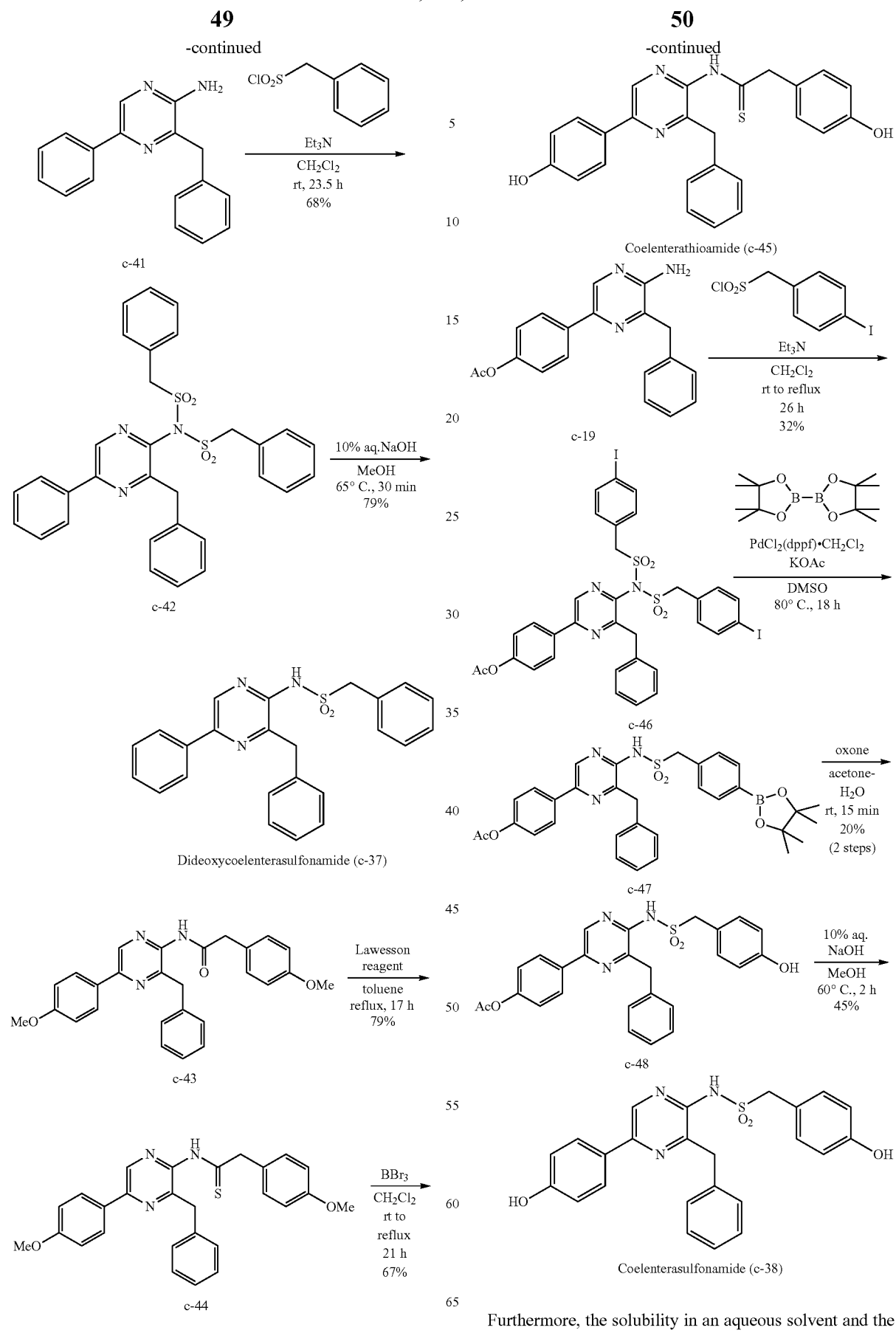
Furthermore, the solubility in an aqueous solvent and the fluorescence quantum yield in an aqueous solvent and in an organic solvent were determined to evaluate the fluorescence intensity of the compound synthesized.

2. Synthesis Examples

Material and Process (1) Chemicals

All chemicals were used as commercially available, unless otherwise indicated.

Solvents for reactions, extractions and chromatography including ethyl acetate, n-hexane, dichloromethane, anhydrous dichloromethane, chloroform, methanol, ethanol, diethyl ether, acetone, toluene and 1,2-dimethoxyethane (Wako) were used as commercially available.

Reaction reagents given below were used.

Phenylacetyl chloride (Wako), 4-(dimethylamino)pyridine (Wako), 1.0 M boron tribromide/dichloromethane solution (Aldrich), Lawesson's reagent (Aldrich), benzylsulfonyl chloride (Wako), acetic anhydride (Wako), triethylamine (Wako), sodium hydroxide (Wako), anhydrous pyridine (Wako), acetyl chloride (Wako), methanesulfonyl chloride (Wako), p-toluenesulfonyl chloride (Kanto), p-nitrobenzenesulfonyl chloride (Aldrich), phenyl boronate (Acros organics), sodium carbonate (Wako), and dichlorobis(triphenylphosphine) palladium (II) (Aldrich).

(2) Chromatography

Silicagel 60 $F_{254}$ (Cat. No. 1.05715.) manufactured by MERCK, Inc. was used as thin layer chromatography (TLC) for analysis. Spots were detected by the method using an ultraviolet lamp (254 nm or 365 nm), iodine adsorption, and dipping in an acidic aqueous solution of phosphomolybdic acid followed by baking on a hot plate. For preparative flash column chromatography, Silicagel 60N, Cat. No. 37563-85, with 40-50 μm mesh manufactured by Kanto Chemical Co., Inc., or Silicagel 60N, Cat. No. 37565-84, with 63-200 μm mesh manufactured by Kanto Chemical Co., Inc. was used as normal phase silica gel. In EXAMPLES, the ratios of solvent mixtures for chromatography are by v/v, unless otherwise indicated.

(3) Measurement of Physical Properties

Melting point (Mp.) was determined using a micro melting point measuring apparatus MP-J3 manufactured by YANACO, Inc.

Ultraviolet absorption spectra (UV) and OD values (330 nm) were measured at 25° C. with V-560 manufactured by Jasco. A 30 μM methanol solution and a phosphate buffer aqueous solution of pH 7.4 (PB) of each sample were prepared. Measurements were performed in a quartz cell (light path length of 10 mm). In the case of a sparingly soluble compound, the compound was first dissolved in a small volume of DMSO and the resulting solution was diluted with each solvent to prepare the sample. When DMSO was used, its content ratio was described. All measurements were made under the conditions of 0.5 nm band width, medium response and 200 nm/min scan speed.

Nuclear magnetic resonance spectra (NMR spectra) at $^1H$ (400 MHz) were determined in DMSO-$d_6$ using a Unity Plus 400 manufactured by Varian Corp. The peak of non-deuterated dimethylsulfoxide remained in DMSO-$d_6$ as a solvent for measurements was set at δ 2.49 as a standard for $^1H$ NMR chemical shifts.

Nuclear magnetic resonance spectra (NMR spectra) at $^{13}C$ (75.5 MHz) were determined in DMSO-$d_6$ using a MERCURY 300 manufactured by Varian Corp. The peak in DMSO-$d_6$ as a solvent for measurements was set to δ 39.5 as a standard for $^{13}C$ NMR chemical shifts. For the compound where the peaks were overlapped, heavy methanol was added to separate the peaks, indicating to that effect.

Infrared spectroscopic spectra (IR) were measured by diffuse reflectance spectroscopy on a SHIMADZU-made IRPrestige-21 spectrometer equipped with DRS-8000A.

High resolution mass spectrometric spectra (HRMS) were measured on JMS-700 manufactured by JEOL by the electron impact ionization (EI) method, the fast atom bombardment (FAB$^+$) method, or the electrospray ionization (ESI$^+$) method using MicrOTOF manufactured by Brucker, Inc.

The elemental analyses were performed by using CHN CORDER MT-5 manufactured by YANACO, Inc.

Synthesis Example 1

3-Benzyl-5-(4-methoxyphenyl)-2-(phenylacetylamino)pyrazine (c-16)

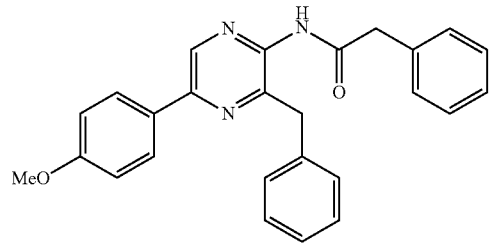 [SMILES: COc1ccc(-c2cnc(NC(=O)Cc3ccccc3)c(Cc3ccccc3)n2)cc1]

Under an argon atmosphere, 2-amino-3-benzyl-5-(4-methoxyphenyl)pyrazine (c-11) (prepared by the method described in Adamczyk, M. et al., Org. Prep. Proced. Int., 33, 477-485 (2001)) (400 mg, 1.37 mmol) was dissolved in pyridine (4 mL) and to this was added 4-(dimethylamino)pyridine (17.3 mg, 142 μmol), and then cooled to 0° C. To this was added phenylacetyl chloride (540 μL, 4.08 mmol) and stirred for 3.5 h after warming to room temperature. To this was added saturated aqueous solution of sodium bicarbonate to stop the reaction and extracted 3 times with dichloromethane. The organic layer was washed with saturated aqueous solution of sodium sulfate and then dried over anhydrous sodium sulfate. After removing anhydrous sodium sulfate by filtration, the filtrate was concentrated under reduced pressure. The residue was purified by silica gel column chromatography (20 g, dichloromethane/ethyl acetate=15/1) to give 3-benzyl-5-(4-methoxyphenyl)-2-(phenylacetylamino)pyrazine (c-16) as a pale yellow solid (540 mg, 96.2%). $R_f$=0.25 (dichloromethane/ethyl acetate=15/1). Mp. 197.5-202° C. UV (MeOH) $\lambda_{max}$ (log ε) 330 (4.20), 293 (4.20), 274 (4.18). UV (pH 7.4 PB, 1% DMSO) $\lambda_{max}$ (log ε) 333.5 (3.73), 280.5 (3.85). $^1H$ NMR (400 MHz, DMSO-$d_6$) δ 3.68 (s, 2H), 3.81 (s, 3H), 4.03 (s, 2H), 7.01-7.08 (m, 4H), 7.11-7.24 (m, 3H), 7.24-7.30 (m, 1H), 7.32-7.38 (m, 4H), 8.01-8.06 (AA'BB', 2H), 8.88 (s, 1H), 10.52 (s, 1H). $^{13}C$ NMR (75.5 MHz, DMSO-$d_6$/CD$_3$OD=2/1) δ 40.2, 42.9, 55.5, 114.8 (2C), 126.7, 127.2, 128.4 (2C), 128.6, 128.7 (2C), 128.8 (2C), 129.4 (2C), 129.7 (2C), 136.0, 137.5, 138.7, 143.9, 149.0, 151.2, 161.3, 170.6. IR (KBr, cm$^{-1}$) 706, 837, 1034, 1179, 1248, 1296, 1413, 1439, 1449, 1497, 1545, 1574, 1609, 1670, 3281, 3381. HRMS (FAB$^+$) m/z 410.1876 (M+H, $C_{26}H_{24}N_3O_2$ requires 410.1869).

Synthesis Example 2

3-Benzyl-5-(4-hydroxyphenyl)-2-(phenylacetylamino)pyrazine (h-coelenteramide) (c-13)

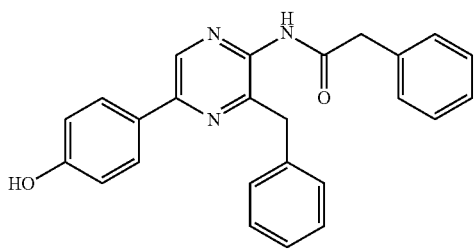 [SMILES: O=C(Cc1ccccc1)Nc1ncc(-c2ccc(O)cc2)nc1Cc1ccccc1]

Under an argon atmosphere, 3-benzyl-5-(4-methoxyphenyl)-2-(phenylacetylamino)pyrazine (c-16) (250 mg, 611 was dissolved in anhydrous dichloromethane (15 mL) and to this was added 1.0 M solution of boron tribromide in dichloromethane (2.15 mL, 2.15 mmol) while stirring at room temperature, and heated to reflux for 15 h. After refluxing, it was cooled to room temperature, and to this was added saturated aqueous solution of sodium bicarbonate to stop the reaction, and concentrated under reduced pressure using a rotary evaporator to remove dichloromethane. The suspension was filtered and the residue was dried to give 270 mg of the crude product as a pale yellow solid. Recrystallization from methanol gave 3-benzyl-5-(4-hydroxyphenyl)-2-(phenylacetylamino)pyrazine (h-coelenteramide) (c-13) as a colorless solid (107 mg, 44.1%). $R_f$=0.20 (dichloromethane/ethyl acetate=4/1). Mp. 259-261° C. UV (MeOH) $\lambda_{max}$ (log ϵ) 332 (4.38), 294.5 (4.38), 276 (4.35). UV (pH 7.4 PB, 1% DMSO) $\lambda_{max}$ (log ϵ) 345.5 (3.52), 303 (3.57). $^1$H NMR (400 MHz, DMSO-$d_6$) δ 3.67 (s, 2H), 4.01 (s, 2H), 6.84-6.89 (AA'BB', 2H), 7.02 (d, J=6.9 Hz, 2H), 7.11-7.23 (m, 4H), 7.23-7.30 (m, 1H), 7.32-7.37 (m, 4H), 7.90-7.95 (AA'BB', 2H), 8.82 (s, 1H), 9.87 (s, 1H), 10.48 (s, 1H). $^{13}$C NMR (75.5 MHz, DMSO-$d_6$) δ 39.7, 42.4, 115.8 (2C), 126.2, 126.4, 126.7, 128.1 (2C), 128.3 (2C), 128.4 (2C), 128.9 (2C), 129.3 (2C), 135.6, 136.9, 138.3, 143.3, 148.6, 150.5, 159.1, 169.9. IR (KBr, cm$^{-1}$) 662, 702, 712, 727, 843, 1157, 1173, 1231, 1281, 1321, 1355, 1368, 1452, 1495, 1523, 1541, 1584, 1595, 1611, 1668, 3063, 3169, 3264. HRMS (FAB$^+$) m/z 396.1706 (M+H, $C_{25}H_{22}N_3O_2$ requires 396.1712).

Synthesis Example 3

3-Benzyl-5-(4-methoxyphenyl)-2-(phenylthioacetylamino)pyrazine (c-17)

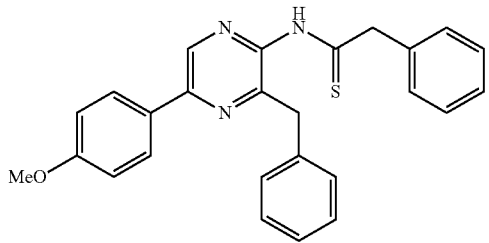 [SMILES: COc1ccc(-c2cnc(NC(=S)Cc3ccccc3)c(Cc3ccccc3)n2)cc1]

Under an argon atmosphere, 3-benzyl-5-(4-methoxyphenyl)-2-(phenylacetylamino)pyrazine (c-16) (539 mg, 1.32 mmol) was suspended in anhydrous toluene (50 mL) and to this was added Lawesson's reagent (320 mg, 790 µmol) while stirring at room temperature, and then heated to reflux for 17 h. After refluxing, it was cooled to room temperature, and concentrated under reduced pressure with a rotary evaporator. The residue was purified by silica gel column chromatography (55 g, n-hexane/ethyl acetate=3/1) to give 3-benzyl-5-(4-methoxyphenyl)-2-(phenylthioacetylamino)pyrazine (c-17) as a yellow amorphous powder (430 mg, 76.6%). $R_f$=0.33 (n-hexane/ethyl acetate=7/3). Mp. 45-47° C. UV (MeOH) $\lambda_{max}$ (log ϵ) 334 (4.23), 295 (4.16), 272 (4.25). UV (pH 7.4 PB) $\lambda_{max}$(log ϵ) 360.5 (4.22), 283.5 (4.16). $^1$H NMR (400 MHz, DMSO-$d_6$) δ 3.81 (s, 3H), 3.92 (s, 2H), 4.14 (s, 2H), 7.01 (d, J=6.8 Hz, 2H), 7.04-7.10 (AA'BB', 2H), 7.12-7.24 (m, 3H), 7.29 (t, J=7.3 Hz, 1H), 7.37 (t, J=7.3 Hz, 2H), 7.51 (d, J=7.1 Hz, 2H), 8.05-8.10 (AA'BB', 2H), 8.99 (s, 1H), 12.20 (s, 1H). $^{13}$C NMR (75.5 MHz, DMSO-$d_6$) δ 39.3, 51.6, 55.3, 114.5 (2C), 126.3, 127.0, 127.6, 128.2 (2C), 128.3 (2C), 128.4 (2C), 128.9 (2C), 129.0 (2C), 136.9, 137.9, 138.0, 145.0, 149.6, 152.1, 160.9, 204.6. IR (KBr, cm$^{-1}$) 700, 835, 1028, 1115, 1175, 1252, 1292, 1319, 1369, 1422, 1437, 1493, 1516, 1607, 2961, 3395. HRMS (FAB$^+$) m/z 426.1646 (M+H, $C_{26}H_{24}N_3OS$ requires 426.1640).

Synthesis Example 4

3-Benzyl-5-(4-hydroxyphenyl)-2-(phenylthioacetylamino)pyrazine (h-coelenterathioamide) (c-14)

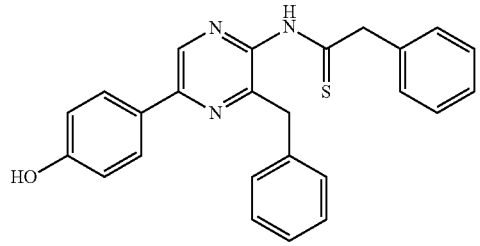

Under an argon atmosphere, 3-benzyl-5-(4-methoxyphenyl)-2-(phenylthioacetylamino)pyrazine (c-17) (114 mg, 267 µmol) was dissolved in anhydrous dichloromethane (2 mL), and then cooled to 0° C. To this was added 1.0 M solution of boron tribromide in dichloromethane (1.35 mL, 1.35 mmol) and stirred for 3.5 h after warming to room temperature. To this was added saturated aqueous solution of sodium bicarbonate to stop the reaction and concentrated under reduced pressure with a rotary evaporator to remove dichloromethane. The suspension was filtered and the residue was dried to give 105 mg of the crude product as a red solid, which was purified by silica gel chromatography (8.2 g, n-hexane/ethyl acetate=3/2) to give 3-benzyl-5-(4-hydroxyphenyl)-2-(phenylthioacetylamino)pyrazine (h-coelenterathioamide) (c-14) as an orange solid (88.9 mg, 80.9%). $R_f$=0.21 (n-hexane/ethyl acetate=3/2). Mp. 195-198° C. UV (MeOH) $\lambda_{max}$ (log ϵ) 336.5 (4.24), 297 (4.18), 273.5 (4.26). UV (pH 7.4 PB) $\lambda_{max}$ (log ϵ) 336.5 (4.12), 270 (4.20). $^1$H NMR (400 MHz, DMSO-$d_6$) δ 3.90 (s, 2H), 4.13 (s, 2H), 6.84-6.90 (AA'BB', 2H), 6.99 (d, J=7.1 Hz, 2H), 7.10-7.24 (m, 3H), 7.26 (t, J=7.1 Hz, 1H), 7.36 (t, J=7.1 Hz, 2H), 7.50 (d, J=7.1 Hz, 2H), 7.93-7.99 (AA'BB', 2H), 8.91 (s, 1H), 9.94 (s, 1H), 12.17 (s, 1H). $^{13}$C NMR (75.5 MHz, DMSO-$d_6$) δ 39.4, 51.6, 115.9 (2C), 126.1, 126.3, 127.0, 128.3 (2C), 128.36 (2C), 126.44 (2C), 128.9 (2C), 129.0 (2C), 136.9, 137.6, 138.1, 144.6, 150.0, 152.0, 159.5, 204.5. IR (KBr, cm$^{-1}$) 702, 839, 1140, 1169, 1207, 1234, 1283, 1319, 1360, 1435, 1450, 1472, 1491, 1522, 1607, 3069, 3478. HRMS (FAB$^+$) m/z 412.1490 (M+H, $C_{25}H_{22}N_3OS$ requires 412.1484).

Synthesis Example 5

3-Benzyl-2-benzylsulfonylamino-5-(4-methoxyphenyl)pyrazine (c-18)

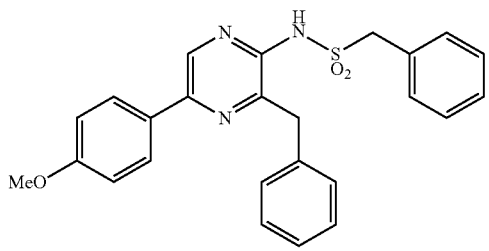 [SMILES: COc1ccc(-c2cnc(NS(=O)(=O)Cc3ccccc3)c(Cc3ccccc3)n2)cc1]

Under an argon atmosphere, 2-amino-3-benzyl-5-(4-methoxyphenyl)pyrazine (c-11) (prepared by the method described in Adamczyk M. et al., Org. Prep. Proced. Int., 33, 477-485 (2001)) (99.5 mg, 342 µmol) was dissolved in pyridine (1 mL) and cooled to 0° C. To this was added benzylsulfonyl chloride (84.7 mg, 444 µmol) and stirred for an hour after warming to room temperature. To this was added benzylsulfonyl chloride (13.8 mg, 72.3 µmol) and the mixture was stirred for 2.5 h. To this was further added benzylsulfonyl chloride (13.9 mg, 72.9 pimp and the mixture was stirred for 15 h. To this was further added benzylsulfonyl chloride (13.1 mg, 68.7 µmol) and the mixture was stirred for 5.5 h. To this was added 2 M hydrochloric acid to stop the reaction, and after separating the aqueous layer and organic layer, it was extracted 3 times with dichloromethane. The organic layer was washed with saturated aqueous solution of sodium sulfate and then dried over anhydrous sodium sulfate. After removing anhydrous sodium sulfate by filtration, the organic layer was concentrated under reduced pressure. The residue was purified by column chromatography (7 g, n-hexane/ethyl acetate=7/3→ethyl acetate). The resulting solid was recrystallized from ethyl acetate to give 3-benzyl-2-benzylsulfonylamino-5-(4-methoxyphenyl)pyrazine (c-18) as a colorless solid (56.0 mg, 36.8%). $R_f$=0.32 (n-hexane/ethyl acetate=7/3). Mp. 213-215° C. UV (MeOH, 0.3% DMSO) $\lambda_{max}$ (log ε) 334.5 (4.04), 290 (4.21), 276.5 (4.23). UV (pH 7.4 PB, 0.3% DMSO) $\lambda_{max}$ (log ε) 348.5 (3.90), 293 (3.95). $^1$H NMR (400 MHz, DMSO-d$_6$) δ 3.80 (s, 3H), 4.22 (s, 2H), 4.91 (s, 2H), 7.02-7.07 (AA'BB', 2H), 7.14-7.21 (m, 1H), 7.24-7.27 (m, 4H), 7.36 (s, 5H), 7.99 (d, J=7.3 Hz, 2H), 8.88 (s, 1H), 10.46 (s, 1H). $^{13}$C NMR (75.5 MHz, DMSO-d$_6$) δ 38.0, 55.3, 59.6, 114.4 (2C), 126.3, 127.6 (2C), 128.1, 128.3 (2C), 128.4, 128.5 (2C), 129.0 (2C), 129.9, 130.9 (2C), 136.2, 138.1, 144.6, 145.8, 146.0, 160.3. IR (KBr, cm$^{-1}$) 459, 538, 586, 698, 748, 785, 831, 893, 912, 926, 1032, 1121, 1132, 1177, 1215, 1256, 1287, 1319, 1395, 1452, 1495, 1516, 1609, 3231. HRMS (FAB$^+$) m/z 446.1548 (M+H, $C_{25}H_{24}N_3O_3S$ requires 446.1548).

Synthesis Example 6

5-(4-Acetoxyphenyl)-2-amino-3-benzylpyrazine (c-19)

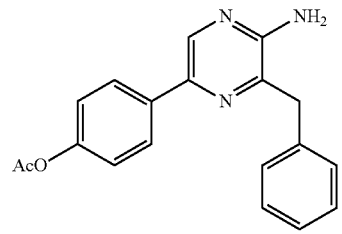 [SMILES: CC(=O)Oc1ccc(-c2cnc(N)c(Cc3ccccc3)n2)cc1]

Under an argon atmosphere, 2-amino-3-benzyl-5-(4-hydroxyphenyl)pyrazine (coelenteramine) (c-5) (prepared by the method described in Adamczyk, M. et al., Org. Prep. Proced. Int., 33, 477-485 (2001)) (303 mg, 1.09 mmol) was dissolved in pyridine (2 mL) and cooled to 0° C. To this was added acetic anhydride (133 µL, 1.40 mmol) and stirred for an hour after warming to room temperature. To the mixture was added saturated aqueous solution of sodium bicarbonate and ethyl acetate to stop the reaction. After separating the aqueous layer and organic layer, it was extracted 3 times with ethyl acetate. The organic layer was washed 3 times with water and once with saturated brine, and then dried over anhydrous sodium sulfate. After removing anhydrous sodium sulfate by filtration, the filtrate was concentrated under reduced pressure with a rotary evaporator. The residue was purified by column chromatography (50 g, n-hexane/ethyl acetate=1/1) to give 5-(4-acetoxyphenyl)-2-amino-3-benzylpyrazine (c-19) as a pale yellow solid (337 mg, 96.7%). $R_f$=0.31 (n-hexane/ethyl acetate=3/2). Mp. 183.5-185.5° C. $^1$H NMR (400 MHz, DMSO-d$_6$) δ 2.27 (s, 3H), 4.07 (s, 2H), 6.42 (s, 2H), 7.12-7.17 (AA'BB', 2H), 7.19 (d, J=7.2 Hz, 1H), 7.27 (t, J=7.5 Hz, 2H), 7.33 (d, J=7.0 Hz, 2H), 7.90-7.95 (AA'BB', 2H), 8.41 (s, 1H). IR (KBr, cm$^{-1}$) 513, 596, 640, 654, 710, 746, 851, 910, 1016, 1136, 1167, 1198, 1217, 1373, 1423, 1452, 1466, 1493, 1508, 1535, 1630, 1746, 3148, 3289.

Synthesis Example 7

5-(4-Acetoxyphenyl)-3-benzyl-2-bis(benzylsulfonyl)aminopyrazine (c-20)

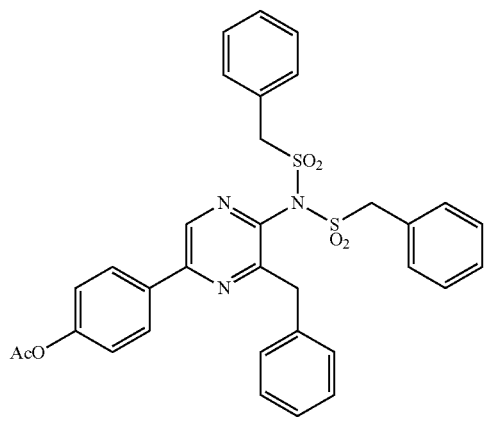 [SMILES: CC(=O)Oc1ccc(-c2cnc(N(S(=O)(=O)Cc3ccccc3)S(=O)(=O)Cc3ccccc3)c(Cc3ccccc3)n2)cc1]

Under an argon atmosphere, 5-(4-acetoxyphenyl)-2-amino-3-benzylpyrazine (c-19) (367 mg, 1.15 mmol) was dissolved in anhydrous dichloromethane (9 mL) and to this was added triethylamine (480 μL, 3.44 mmol), and cooled to 0° C. To this was added benzylsulfonyl chloride (658 mg, 3.45 mmol) and stirred for 4.5 h after warming to room temperature. To this was further added benzylsulfonyl chloride (658 mg, 3.45 mmol) and the mixture was stirred for 1.5 h. To this was added 2 M hydrochloric acid to stop the reaction and after separating the aqueous layer and organic layer, the organic layer was washed once with water and once with saturated brine, and then dried over anhydrous sodium sulfate. After removing anhydrous sodium sulfate by filtration, the filtrate was concentrated under reduced pressure with a rotary evaporator. The residue was purified by silica gel column chromatography (23 g, n-hexane/ethyl acetate=4/1→7/3) to give 5-(4-acetoxyphenyl)-3-benzyl-2-bis(benzylsulfonyl)aminopyrazine (c-20) as a yellow amorphous (487 mg, 67.4%). $R_f$=0.53 (n-hexane/ethyl acetate=3/2). Mp. 84-86.5° C. UV (MeOH) $\lambda_{max}$ (log ε) 307 (4.26), 293.5 (4.21), 259.5 (4.19). UV (pH 7.4 PB) $\lambda_{max}$ (log ε) 320 (4.30), 298.5 (4.25), 265 (4.29). $^1$H NMR (400 MHz, DMSO-$d_6$) δ 2.29 (s, 3H), 3.90 (s, 2H), 5.00 (s, 1H), 5.03 (s, 1H), 5.18 (s, 1H), 5.22 (s, 1H), 7.13-7.17 (m, 2H), 7.18-7.23 (m, 1H), 7.25-7.33 (m, 4H), 7.39-7.45 (m, 10H), 8.09-8.14 (AA'BB', 2H), 9.21 (s, 1H). $^{13}$C NMR (75.5 MHz, DMSO-$d_6$) δ 20.9, 37.4, 61.0 (1C×2), 122.7 (2C), 126.4, 126.8 (1C×2), 128.2 (2C), 128.5 (2C), 128.8 (2C×2), 129.3, 129.6 (2C), 131.6 (2C×2), 132.1, 137.5, 139.2, 141.0, 151.3, 152.5, 155.6, 169.0. IR (KBr, cm$^{-1}$) 509, 534, 611, 696, 777, 876, 912, 1144, 1163, 1198, 1354, 1375, 1416, 1433, 1757. HRMS (FAB$^+$) m/z 628.1582 (M+H, $C_{33}H_{30}N_3O_6S_2$ requires 628.1576).

Synthesis Example 8

3-Benzyl-2-benzylsulfonylamino-5-(4-hydroxyphenyl)pyrazine (h-coelenterasulfonamide) (c-15)

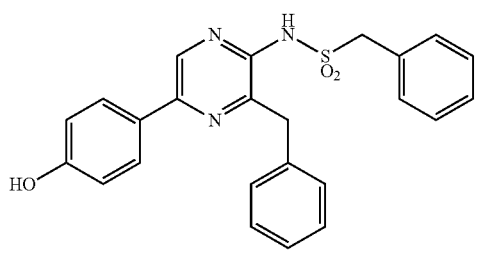 [SMILES: O=S(=O)(Cc1ccccc1)Nc1ncc(-c2ccc(O)cc2)nc1Cc1ccccc1]

5-(4-Acetoxyphenyl)-3-benzyl-2-bis(benzylsulfonyl)aminopyrazine (c-20) (435 mg, 694 μmol) was dissolved in methanol (8 mL) and to this was added 10% (w/v) aqueous solution of sodium hydroxide (1.9 mL) while stirring at room temperature, and stirred at 65° C. for 9.5 h. After cooling to room temperature, to this was added 2 M hydrochloric acid to stop the reaction and extracted twice with ethyl acetate. The organic layer was washed with saturated brine and then dried over anhydrous sodium sulfate. After removing anhydrous sodium sulfate by filtration, the filtrate was concentrated under reduced pressure with a rotary evaporator. The residue was purified by column chromatography (35 g, n-hexane/ethyl acetate=3/1→2/1) to give 3-benzyl-2-benzylsulfonylamino-5-(4-hydroxyphenyl)pyrazine (h-coelenterasulfonamide) (c-15) as a pale yellow solid (286 mg, 95.6%). $R_f$=0.27 (n-hexane/ethyl acetate=3/2). Mp. 144-147° C. (dec.). UV (MeOH) $\lambda_{max}$ (log ε) 336 (4.06), 290 (4.23), 277.5 (4.25). UV (pH 7.4 PB) $\lambda_{max}$ (log ε) 351.5 (4.09), 283 (4.34). $^1$H NMR (400 MHz, DMSO-$d_6$) δ 4.22 (s, 2H), 4.91 (s, 2H), 6.83-6.88 (AA'BB', 2H), 7.14-7.20 (m, 1H), 7.22-7.29 (m, 4H), 7.36 (s, 5H), 7.86-7.93 (AA'BB', 2H), 8.83 (s, 1H), 9.81 (s, 1H), 10.40 (s, 1H). $^{13}$C NMR (75.5 MHz, DMSO-$d_6$) δ 38.0, 59.6, 115.8 (2C), 126.2, 126.5, 127.7, 128.28 (2C), 128.33 (2C), 128.5 (2C), 128.9 (2C), 129.9, 130.9 (2C), 136.0, 138.2, 144.2, 145.8, 146.5, 158.8. IR (KBr, cm$^{-1}$) 527, 542, 604, 698, 835, 893, 912, 926, 935, 1117, 1130, 1188, 1213, 1244, 1267, 1321, 1402, 1452, 1495, 1516, 1595, 1609, 3055, 3221, 3522. HRMS (FAB$^+$) m/z 432.1385 (M+H, $C_{24}H_{22}N_3O_3S$ requires 432.1382).

Synthesis Example 9

3-Benzyl-2-bis(benzyl sulfonyl)amino-5-(4-methoxyphenyl)pyrazine (c-21)

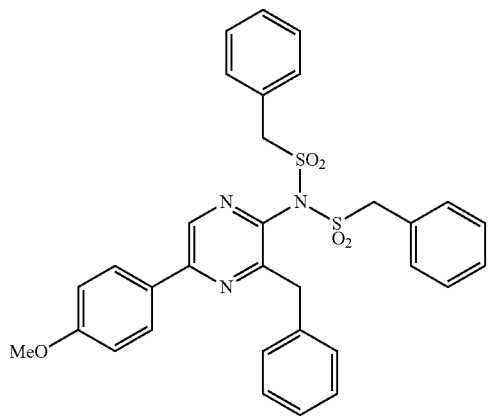 [SMILES: COc1ccc(-c2cnc(N(S(=O)(=O)Cc3ccccc3)S(=O)(=O)Cc3ccccc3)c(Cc3ccccc3)n2)cc1]

2-Amino-3-benzyl-5-(4-methoxyphenyl)pyrazine (c-11) (prepared by the method described in Adamczyk M. et al., Org. Prep. Proced. Int., 33, 477-485 (2001)) (200 mg, 687 μmol) was dissolved in anhydrous dichloromethane (2 mL) and to this was added triethylamine (145 μL, 1.04 mmol), and cooled to 0° C. To this was added benzylsulfonyl chloride (196 mg, 1.03 mmol) and stirred for an hour after warming to room temperature. To this were sequentially added triethylamine (145 μL, 1.04 mmol), anhydrous dichloromethane (1.0 mL) and benzylsulfonyl chloride (131 mg, 687 μmol) and stirred for an hour. Furthermore, to this were sequentially added triethylamine (145 μL, 1.04 mmol), anhydrous dichloromethane (1.0 mL) and benzylsulfonyl chloride (131 mg, 687 μmol) and stirred for 2 h. To this was added 2 M hydrochloric acid to stop the reaction and, after separating the aqueous layer and organic layer, the organic layer was washed once with saturated brine and once with saturated aqueous solution of sodium sulfate, and then dried over anhydrous sodium sulfate. After removing anhydrous sodium sulfate by filtration, the filtrate was concentrated under reduced pressure with a rotary evaporater. The residue was purified by silica gel column chromatography (23 g, n-hexane/ethyl acetate=4/1) to give 3-benzyl-2-bis(benzylsulfonyl)amino-5-(4-methoxyphenyl)pyrazine (c-21) as a yellow amorphous (320 mg, 77.6%). $R_f$=0.63 (n-hexane/ethyl acetate=3/2). Mp. 78-80° C. UV (MeOH) $\lambda_{max}$ (log ε) 332.5 (4.31), 299.5 (4.20), 277.5 (4.06). UV (pH 7.4 PB) $\lambda_{max}$ (log ε) 342.5 (4.29), 303 (4.18), 280.5 (4.15). $^1$H NMR (400 MHz, DMSO-$d_6$) δ 3.87 (s, 3H), 3.97 (s, 2H), 4.78 (s, 1H), 4.82 (s, 1H), 4.94 (s, 1H), 4.97 (s, 1H), 6.96-7.02 (AA'BB', 2H), 7.17 (d, J=7.2 Hz, 2H), 7.19-7.33 (m, 3H), 7.34-7.44 (m, 10H), 7.92-7.98 (AA'BB', 2H), 8.80 (s, 1H). $^{13}$C NMR (75.5 MHz, DMSO-d$_6$) δ 37.4, 55.4, 61.0 (1C×2), 114.7 (2C), 126.4, 126.8 (1C×2), 128.1 (2C), 128.78 (2C), 128.84 (2C×2), 129.0, 129.3, 129.6 (2C), 131.6 (2C×2), 137.6, 138.5, 140.1, 151.9, 155.4, 161.5. IR (KBr, cm$^{-1}$) 501, 611, 696, 773, 876, 922, 1028, 1144, 1163, 1250, 1354, 1373, 1422, 1431, 1454, 1495, 1514, 1607. HRMS (FAB$^+$) m/z 600.1639 (M+H, C$_{32}$H$_{30}$N$_3$O$_5$S$_2$ requires 600.1627).

Synthesis Example 10

5-(4-Acetoxyphenyl)-2-(4-acetoxyphenyl)acetylamino-3-benzylpyrazine (c-29)

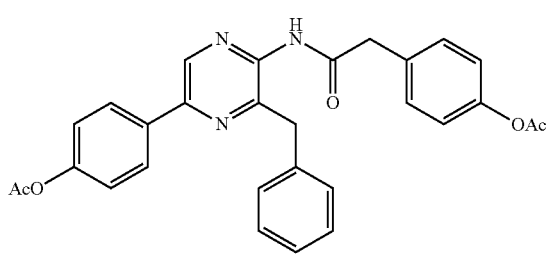 [SMILES: CC(=O)Oc1ccc(CC(=O)Nc2ncc(-c3ccc(OC(C)=O)cc3)nc2Cc2ccccc2)cc1]

Under an argon atmosphere, 3-benzyl-5-(4-hydroxyphenyl)-2-[(4-hydroxyphenyl)acetylamino]pyrazine (coelenteramide) (c-4) (prepared by the method described in Inouye, S. & Hosoya, T., Biochem. Biophys. Res. Commun., 386, 617-622 (2009)) (410 mg, 997 µmol) was dissolved in pyridine (11 mL) and cooled to 0° C. To this was added acetic anhydride (475 µL, 5.02 mmol) and stirred for 22 h after warming to room temperature. To this were added saturated aqueous solution of sodium bicarbonate and ethyl acetate to stop the reaction, and after separating the aqueous layer and organic layer, the organic layer was washed twice with water and once with saturated brine. The precipitate in the organic layer was collected by filtration and dried in vacuo to give 5-(4-acetoxyphenyl)-2-(4-acetoxyphenyl)acetylamino-3-benzylpyrazine (c-29) as a colorless solid (300 mg, 60.7%). R$_f$=0.28 (n-hexane/ethyl acetate=1/1). Mp. 225-227° C. UV (MeOH, 0.3% DMSO) λ$_{max}$ (log ε) 318 (4.14), 290 (4.12), 259 (4.19). $^1$H NMR (400 MHz, DMSO-d$_6$) δ 2.26 (s, 3H), 2.29 (s, 3H), 3.71 (s, 2H), 4.11 (s, 2H), 7.08 (t, J=8.6 Hz, 4H), 7.15 (t, J=7.8 Hz, 1H), 7.21 (t, J=7.8 Hz, 2H), 7.24-7.29 (AA'BB', 2H), 7.34-7.40 (AA'BB', 2H), 8.08-8.14 (AA'BB', 2H), 8.95 (s, 1H), 10.67 (s, 1H). $^{13}$C NMR (75.5 MHz, DMSO-d$_6$) δ 20.89, 20.92, 41.6, 121.8 (2C), 122.5 (2C), 126.3, 127.8 (2C), 128.3 (2C), 128.9 (2C), 130.3 (2C), 132.9, 133.2, 137.9, 138.1, 144.4, 147.5, 149.3, 150.6, 151.7, 169.1, 169.3, 169.9 (one carbon at benzyl position was unobservable due to overlapping with the septet peak of DMSO). IR (KBr, cm$^{-1}$) 515, 590, 654, 704, 854, 918, 1016, 1157, 1190, 1211, 1238, 1346, 1371, 1418, 1449, 1493, 1543, 1672, 1751, 3287. HRMS (FAB$^+$) m/z 496.1863 (M+H, C$_{29}$H$_{26}$N$_3$O$_5$ requires 496.1872).

Synthesis Example 11

5-(4-Acetoxyphenyl)-3-benzyl-2-(phenylacetylamino)pyrazine (c-30)

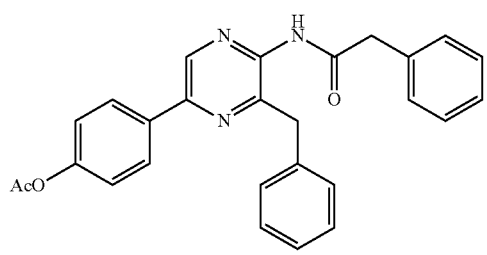 [SMILES: CC(=O)Oc1ccc(-c2cnc(NC(=O)Cc3ccccc3)c(Cc3ccccc3)n2)cc1]

Under an argon atmosphere, 5-(4-acetoxyphenyl)-2-amino-3-benzylpyrazine (c-19) (194 mg, 607 µmol) was dissolved in pyridine (2 mL) and to this was added 4-(dimethylamino)pyridine (7.8 mg, 64 µmol) and cooled to 0° C. To this was added phenylacetyl chloride (160 µL, 1.21 mmol) and stirred for 2 h after warming to room temperature. To this was added saturated aqueous solution of sodium bicarbonate to stop the reaction and after collecting the precipitate by filtration using a Kiriyama funnel, the residue was dried in vacuo to give 5-(4-acetoxyphenyl)-3-benzyl-2-(phenylacetylamino)pyrazine (c-30) as a colorless solid (53.9 mg, 20.3%). R$_f$=0.24 (n-hexane/ethyl acetate=3/2). Mp. 228-231° C. UV (MeOH, 0.3% DMSO) λ$_{max}$ (log ε) 318 (4.19), 290 (4.17), 259 (4.24). $^1$H NMR (400 MHz, DMSO-d$_6$) δ 2.29 (s, 3H), 3.68 (s, 2H), 4.07 (s, 2H), 7.01-7.08 (AA'BB', 2H), 7.11-7.22 (m, 3H), 7.23-7.29 (m, 3H), 7.31-7.38 (m, 4H), 8.07-8.14 (AA'BB', 2H), 8.93 (s, 1H), 10.57 (s, 1H). IR (KBr, cm$^{-1}$) 706, 851, 918, 1157, 1206, 1223, 1346, 1366, 1410, 1449, 1495, 1543, 1576, 1670, 1755, 3248. HRMS (FAB$^+$) m/z 438.1806 (M+H, C$_{27}$H$_{24}$N$_3$O$_3$ requires 438.1818).

Synthesis Example 12

5-(4-Acetoxyphenyl)-3-benzyl-2-(phenylthioacetylamino)pyrazine (c-31)

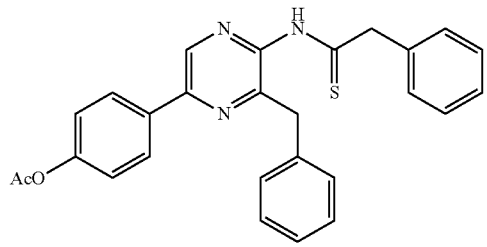 [SMILES: CC(=O)Oc1ccc(-c2cnc(NC(=S)Cc3ccccc3)c(Cc3ccccc3)n2)cc1]

Under an argon atmosphere, 3-benzyl-5-(4-hydroxyphenyl)-2-(phenylthioacetyl amino)pyrazine (h-coelenterathioamide) (c-14) (183 mg, 444 µmol) was dissolved in pyridine (2 mL) and cooled to 0° C. To this was added acetic anhydride (55 µL, 0.58 mmol) and stirred for 2 h after warming to room temperature. To this was further added acetic anhydride (25 µL, 0.26 mmol) and stirred at room temperature for 2.5 h. To this was added saturated aqueous solution of sodium bicarbonate and ethyl acetate to stop the reaction, and after separating the aqueous layer and organic layer, the organic layer was washed 3 times with water and once with brine and dried over anhydrous sodium sulfate. After removing anhydrous sodium sulfate by filtration, the filtrate was concentrated under reduced pressure with a rotary evaporator. After purifying the residue by silica gel column chromatography (22 g, n-hexane/ethyl acetate=2/1), the obtained solid was further purified by silica gel column chromatography (7 g, n-hexane/ethyl acetate=2/1) to give 5-(4-acetoxyphenyl)-3-benzyl-2-(phenylthioacetylamino)pyrazine (c-31) as a pale yellow solid (96.3 mg, 47.8%). $R_f$=0.36 (n-hexane/ethyl acetate=2/1). Mp. 143-145° C. UV (MeOH) $\lambda_{max}$ (log ε) 320 (4.30), 258 (4.41). UV (pH 7.4 PB) $\lambda_{max}$ (log ε) 346 (4.36), 274 (4.35). $^1$H NMR (400 MHz, DMSO-$d_6$) δ 2.29 (s, 3H), 3.95 (s, 2H), 4.14 (s, 2H), 7.00 (d, J=6.6 Hz, 2H), 7.12-7.24 (m, 3H), 7.26-7.32 (AA'BB', 3H), 7.36 (t, J=7.3 Hz, 2H), 7.51 (d, J=7.5 Hz, 2H), 8.12-8.18 (AA'BB', 2H), 9.04 (s, 1H), 12.23 (s, 1H). $^{13}$C NMR (75.5 MHz, DMSO-$d_6$) δ 20.9, 39.4, 51.6, 122.6 (2C), 126.4, 127.0, 128.0 (2C), 128.3 (2C), 128.4 (2C), 128.9 (2C), 129.0 (2C), 132.8, 136.8, 137.9, 138.6, 145.9, 149.0, 151.9, 152.4, 169.1, 204.7. IR (KBr, cm$^{-1}$) 700, 1128, 1165, 1179, 1200, 1238, 1368, 1389, 1416, 1441, 1493, 1508, 1730, 3265. HRMS (FAB$^+$) m/z 454.1583 (M+H, $C_{27}H_{24}N_3O_2S$ requires 454.1589).

Synthesis Example 13

5-(4-Acetoxyphenyl)-3-benzyl-2-(benzylsulfonylamino)pyrazine (c-32)

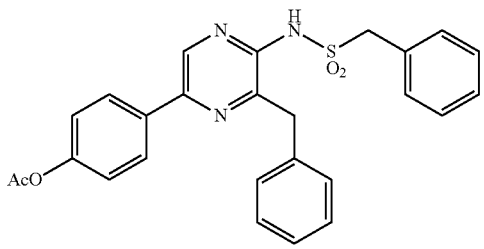 [SMILES: CC(=O)Oc1ccc(-c2cnc(NS(=O)(=O)Cc3ccccc3)c(Cc3ccccc3)n2)cc1]

Under an argon atmosphere, 5-(4-acetoxyphenyl)-2-amino-3-benzylpyrazine (c-19) (303 mg, 949 μmol) was dissolved in pyridine (3 mL) and cooled to 0° C. To this was added benzylsulfonyl chloride (362 mg, 1.90 mmol) and the mixture was stirred for 30 min at the same temperature. To this was further added benzylsulfonyl chloride (89.7 mg, 470 μmol) and the mixture was stirred for 30 min at the same temperature. To this was added saturated aqueous solution of sodium bicarbonate to stop the reaction and extracted 3 times with dichloromethane. The organic layer was washed once with water, once with 2 M hydrochloric acid and once with saturated aqueous solution of sodium sulfate, and then dried over anhydrous sodium sulfate. After removing anhydrous sodium saturation by filtration, the filtrate was concentrated under reduced pressure with a rotary evaporator. The residue was filtered through a Kiriyama funnel and recrystallized from ethyl acetate/methanol (1/1) to give 5-(4-acetoxyphenyl)-3-benzyl-2-(benzylsulfonylamino)pyrazine (c-32) as a colorless solid (124 mg, 27.6%). $R_f$=0.56 (n-hexane/ethyl acetate=1/1). Mp. 240-241° C. UV (MeOH, 0.3% DMSO) $\lambda_{max}$ (log ε) 324 (4.06), 286.5 (4.13), 264 (4.19). UV (pH PB, 0.3% DMSO) $\lambda_{max}$ (log ε) 338.5 (4.01), 290 (4.01), 273.5 (4.02). $^1$H NMR (400 MHz, DMSO-$d_6$) δ 2.29 (s, 3H), 4.25 (s, 2H), 4.92 (s, 2H), 7.14-7.21 (m, 1H), 7.23-7.28 (m, 6H), 7.35 (s, 5H), 8.03-8.12 (AA'BB', 2H), 8.93 (s, 1H), 10.55 (s, 1H). IR (KBr, cm$^{-1}$) 530, 700, 889, 920, 1157, 1179, 1204, 1223, 1325, 1420, 1454, 1748, 3267. HRMS (FAB$^+$) m/z 474.1486 (M+H, $C_{26}H_{24}N_3O_4S$ requires 474.1488).

Synthesis Example 14

5-(4-Acetoxyphenyl)-2-acetylamino-3-benzylpyrazine (c-33)

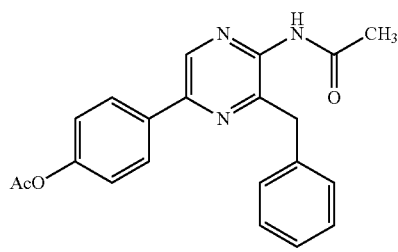

Under an argon atmosphere, 2-amino-3-benzyl-5-(4-hydroxyphenyl)pyrazine (coelenteramine) (c-5) (prepared by the method described in Adamczyk, M. et al., Org. Prep. Proced. Int., 33, 477-485 (2001)) (471 mg, 1.70 mmol) was dissolved in pyridine (3.6 mL) and chloroform (9 mL) and cooled to 0° C. To this was added acetyl chloride (910 μL, 12.8 mmol) and stirred for an hour after warming to room temperature. To this was added saturated aqueous solution of sodium bicarbonate to stop the reaction and extracted 3 times with dichloromethane. The organic layer was washed with aqueous solution of saturated sodium sulfate and dried over anhydrous sodium sulfate. After removing anhydrous sodium sulfate by filtration, the filtrate was concentrated under reduced pressure with a rotary evaporator. The residue was purified by silica gel column chromatography (45 g, n-hexane/ethyl acetate=1/1→1/3) to give 5-(4-acetoxyphenyl)-2-acetylamino-3-benzylpyrazine (c-33) as a pale yellow solid (355 mg, 57.8%). $R_f$=0.17 (n-hexane/ethyl acetate=1/1). Mp. 215.5-217° C. (dec.). UV (MeOH) $\lambda_{max}$ (log ε) 317 (4.09), 290 (4.08), 259 (4.15). UV (pH 7.4 PB) $\lambda_{max}$ (log ε) 315 (4.07), 292 (3.98), 253.5 (4.08). $^1$H NMR (400 MHz, DMSO-$d_6$) δ 2.05 (s, 3H), 2.29 (s, 3H), 4.18 (s, 2H), 7.15-7.22 (m, 3H), 7.23-7.29 (m, 4H), 8.09-8.14 (AA'BB', 2H), 8.94 (s, 1H), 10.31 (s, 1H). $^{13}$C NMR (75.5 MHz, DMSO-$d_6$) δ 20.9, 23.0, 39.9, 122.5 (2C), 126.3, 127.7 (2C), 128.3 (2C), 129.0 (2C), 133.2, 137.8, 138.2, 144.7, 147.3, 150.5, 151.6, 169.1, 169.2. IR (KBr, cm$^{-1}$) 706, 916, 1016, 1159, 1223, 1260, 1369, 1450, 1497, 1545, 1578, 1670, 1751, 3279. HRMS (FAB$^+$) m/z 362.1509 (M+H, $C_{21}H_{20}N_3O_3$ requires 362.1505).

Synthesis Example 15

2-Acetylamino-3-benzyl-5-(4-hydroxyphenyl)pyrazine (coelenteracetamide) (c-25)

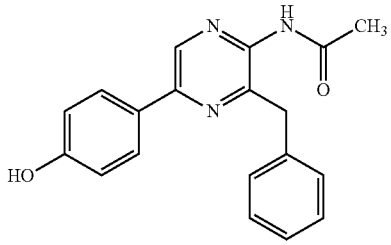 [SMILES: CC(=O)Nc1ncc(-c2ccc(O)cc2)nc1Cc1ccccc1]

5-(4-Acetoxyphenyl)-2-acetylamino-3-benzylpyrazine (c-33) (355 mg, 982 μmol) was dissolved in methanol (8 mL), to which was added 10% (w/v) aqueous solution of sodium hydroxide (1.8 mL) while stirring at room temperature and then stirred for an hour. To this was added 2 M hydrochloric acid to stop the reaction and extracted 3 times with ethyl acetate. The organic layer was washed with saturated brine and then dried over anhydrous sodium sulfate. After removing anhydrous sodium sulfate by filtration, the filtrate was concentrated under reduced pressure. After purifying the residue by column chromatography (37 g, n-hexane/ethyl acetate=1/2), the obtained solid was recrystallized from methanol to give 2-acetylamino-3-benzyl-5-(4-hydroxyphenyl)pyrazine (coelenteracetamide) (c-25) as a colorless solid (109 mg, 34.8%). $R_f$=0.23 (n-hexane/ethyl acetate=1/2). UV (MeOH) $\lambda_{max}$ (log ε) 332 (4.14), 294 (4.15), 275.5 (4.12). UV (pH 7.4 PB) $\lambda_{max}$ (log ε) 328 (4.14), 289.5 (4.03), 270 (4.08). $^1$H NMR (400 MHz, DMSO-$d_6$) δ 2.03 (s, 3H), 4.13 (s, 2H), 6.84-6.89 (AA'BB', 2H), 7.14-7.21 (m, 3H), 7.23-7.29 (m, 2H), 7.89-7.94 (AA'BB', 2H), 8.80 (s, 1H), 9.91 (s, 1H), 10.21 (s, 1H). IR (KBr, cm$^{-1}$) 592, 631, 702, 746, 837, 1128, 1157, 1173, 1211, 1231, 1279, 1314, 1368, 1435, 1497, 1518, 1543, 1582, 1591, 1611, 1672, 3026, 3073, 3254. HRMS (FAB$^+$) m/z 320.1399 (M+H, $C_{19}H_{18}N_3O_2$ requires 320.1399).

Synthesis Example 16

2-Acetylamino-3-benzyl-5-(4-methoxyphenyl)pyrazine (c-24)

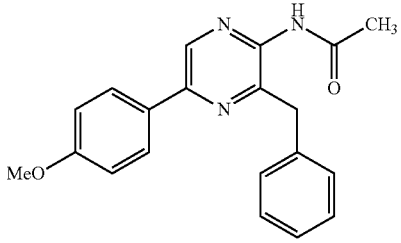 [SMILES: COc1ccc(-c2cnc(NC(C)=O)c(Cc3ccccc3)n2)cc1]

Under an argon atmosphere, 2-amino-3-benzyl-5-(4-methoxyphenyl)pyrazine (c-11) (prepared by the method described in Adamczyk, M. et al., Org. Prep. Proced. Int., 33, 477-485 (2001)) (199 mg, 681 μmol) was dissolved in anhydrous pyridine (1.4 mL) and chloroform (4 mL) and cooled to 0° C. To this was added acetyl chloride (365 μL, 5.13 mmol) and stirred for an hour after warming to room temperature. To this was added saturated aqueous solution of sodium bicarbonate to stop the reaction, and extracted 3 times with dichloromethane. The organic layer was washed with saturated aqueous solution of sodium sulfate and dried over anhydrous sodium sulfate. After removing anhydrous sodium sulfate by filtration, the filtrate was concentrated under reduced pressure with a rotary evaporator. The residue was recrystallized from methanol to give 2-acetylamino-3-benzyl-5-(4-methoxyphenyl)pyrazine (c-24) as a colorless solid (74.6 mg, 32.9%). $R_f$=0.14 (n-hexane/ethyl acetate=3/2). UV (MeOH) $\lambda_{max}$ (log ε) 329.5 (4.18), 293 (4.18), 274 (4.16). UV (pH 7.4 PB) $\lambda_{max}$ (log ε) 328 (4.11), 289.5 (4.01), 270.5 (4.05). $^1$H NMR (400 MHz, DMSO-$d_6$) δ 2.04 (s, 3H), 3.81 (s, 3H), 4.15 (s, 2H), 7.02-7.08 (AA'BB', 2H), 7.15-7.22 (m, 3H), 7.23-7.29 (m, 2H), 8.00-8.05 (AA'BB', 2H), 8.87 (s, 1H), 10.25 (s, 1H). IR (KBr, cm$^{-1}$) 698, 744, 833, 1032, 1157, 1175, 1213, 1256, 1285, 1327, 1368, 1416, 1450, 1499, 1543, 1587, 1609, 1670, 3258. HRMS (FAB$^+$) m/z 334.1557 (M+H, $C_{20}H_{20}N_3O_2$ requires 334.1556).

Synthesis Example 17

5-(4-Acetoxyphenyl)-3-benzyl-2-bis(methanesulfonyl)aminopyrazine (c-39)

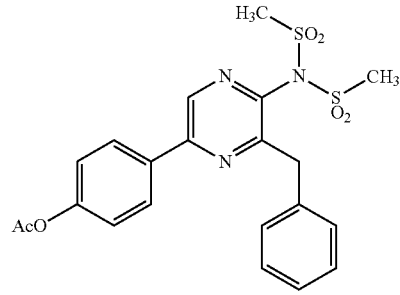 [SMILES: CC(=O)Oc1ccc(-c2cnc(N(S(C)(=O)=O)S(C)(=O)=O)c(Cc3ccccc3)n2)cc1]

Under an argon atmosphere, 5-(4-acetoxyphenyl)-2-amino-3-benzylpyrazine (c-19) (337 mg, 1.05 mmol) was dissolved in anhydrous dichloromethane (9 mL), and to this was added triethylamine (220 μL, 1.58 mmol) and stirred at room temperature. To this was added methanesulfonyl chloride (245 μL, 3.16 mmol) and stirred for 1.5 h at the same temperature. To this was added 2 M hydrochloric acid to stop the reaction and after separating the aqueous layer and organic layer, the organic layer was washed with saturated aqueous solution of sodium sulfate and dried over anhydrous sodium sulfate. After removing anhydrous sodium sulfate by filtration, the filtrate was concentrated under reduced pressure with a rotary evaporator. The residue was purified by silica gel column chromatography (28 g, n-hexane/ethyl acetate=3/1→3/2) to give 5-(4-acetoxyphenyl)-3-benzyl-2-bis(methanesulfonyl)aminopyrazine (c-39) as a yellow amorphous (241 mg, 48.3%). $R_f$=0.32 (n-hexane/ethyl acetate=3/2). Mp. 165.5-167° C. UV (MeOH) $\lambda_{max}$ (log ε) 306 (4.29), 293 (4.25), 259 (4.21). UV (pH PB) $\lambda_{max}$ (log ε) 336.5 (4.19), 264 (4.09). $^1$H NMR (400 MHz, DMSO-$d_6$) δ 2.29 (s, 3H), 3.59 (s, 6H), 4.36 (s, 2H), 7.20-7.26 (m, 1H), 7.26-7.35 (m, 6H), 8.11-8.17 (AA'BB', 2H), 9.14 (s, 1H). $^{13}$C NMR (75.5 MHz, DMSO-$d_6$) δ 20.9, 38.5, 43.1 (1C×2), 122.7 (2C), 126.6, 128.3 (2C), 128.6 (2C), 129.5 (2C), 132.1, 137.6, 139.2, 141.5, 151.4, 152.5, 155.6, 169.0. IR (KBr, cm$^{-1}$) 509, 523, 706, 756, 766, 912, 974, 1015, 1163, 1200, 1321, 1368, 1418, 1435, 1528, 1603, 1755, 3032. HRMS (FAB+) m/z 476.0936 (M+H, $C_{21}H_{22}N_3O_6S_2$ requires 476.0950).

Synthesis Example 18

3-Benzyl-5-(4-hydroxyphenyl)-2-(methanesulfonylamino)pyrazine (coelenteramesylamide) (c-34)

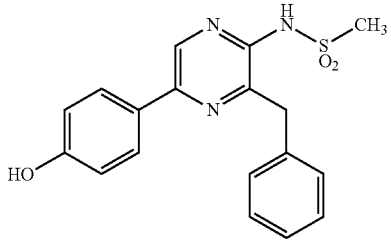 [SMILES: CS(=O)(=O)Nc1ncc(-c2ccc(O)cc2)nc1Cc1ccccc1]

5-(4-Acetoxyphenyl)-3-benzyl-2-bis(methanesulfonyl)aminopyrazine (c-39) (239 mg, 503 μmol) was suspended in methanol (5 mL) and to this was added 10% (w/v) aqueous solution of sodium hydroxide (1.2 mL) while stirring at room temperature and then stirred at 65° C. for 30 min. After cooling to room temperature, to this was added 2 M hydrochloric acid to stop the reaction and extracted twice with ethyl acetate. The organic layer was washed with saturated brine and dried over anhydrous sodium sulfate. After removing anhydrous sodium sulfate by filtration, the filtrate was concentrated under reduced pressure with a rotary evaporator. The residue was purified by column chromatography (23 g, n-hexane/ethyl acetate=1/1) to give 3-benzyl-5-(4-hydroxyphenyl)2-(methanesulfonylamino)pyrazine (coelenteramesylamide) (c-34) as a pale yellow solid (166 mg, 92.6%). $R_f$=0.30 (n-hexane/ethyl acetate=1/1). Mp. 208-209° C. (dec.). UV (MeOH) $\lambda_{max}$ (log ε) 335 (4.12), 290 (4.25), 276 (4.27). UV (pH 7.4 PB) $\lambda_{max}$ (log ε) 349 (4.14), 281 (4.38). $^1$H NMR (400 MHz, DMSO-$d_6$) δ 3.36 (s, 3H), 4.25 (s, 2H), 6.82-6.87 (AA'BB', 2H), 7.15-7.23 (m, 1H), 7.29 (d, J=5.0 Hz, 4H), 7.83-7.88 (AA'BB', 2H), 8.73 (s, 1H), 9.80 (s, 1H), 10.41 (s, 1H). $^{13}$C NMR (75.5 MHz, DMSO-$d_6$) δ 38.2, 42.7, 115.8 (2C), 126.4, 126.6, 127.7 (2C), 128.4 (2C), 129.0 (2C), 135.9, 138.1, 144.3, 146.0, 146.4, 158.8. IR (KBr, cm$^{-1}$) 521, 538, 588, 606, 700, 750, 827, 841, 889, 916, 939, 970, 1118, 1138, 1153, 1175, 1213, 1273, 1314, 1400, 1456, 1495, 1609, 3206. HRMS (FAB+) m/z 356.1060 (M+H, $C_{18}H_{18}N_3O_3S$ requires 356.1069).

Synthesis Example 19

3-Benzyl-5-(4-hydroxyphenyl)-2-[(4-methylphenyl)sulfonylamino]pyrazine (coelentera-p-tosylamide) (c-35)

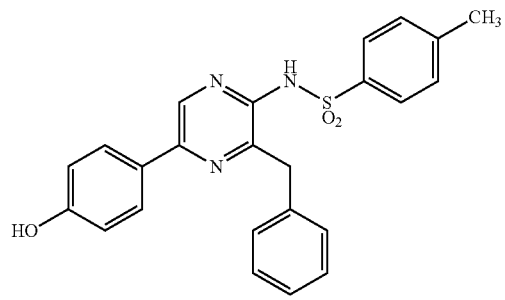

Under an argon atmosphere, 2-amino-3-benzyl-5-(4-hydroxyphenyl)pyrazine (coelenteramine) (c-5) (prepared by the method described in Adamczyk M. et al., Org. Prep. Proced. Int., 33, 477-485 (2001)) (199 mg, 718 μmol) was dissolved in pyridine (1.5 mL) and to this was added 4-(dimethylamino)pyridine (9.0 mg, 74 μmol) and cooled to 0° C. To this was added p-toluenesulfonyl chloride (410 mg, 2.15 mmol) and stirred for 2 h after warming to room temperature. To this were added 2 M hydrochloric acid and dichloromethane to stop the reaction and, after separating the aqueous layer and organic layer, it was extracted 3 times with dichloromethane and was washed with saturated aqueous solution of sodium sulfate and then dried over anhydrous sodium sulfate. After removing anhydrous sodium sulfate by filtration, the filtrate was concentrated under reduced pressure with a rotary evaporator. The residue was dissolved in methanol (5 mL) and to this was added 10% (w/v) aqueous, solution of sodium hydroxide (1.2 mL) while stirring at room temperature and stirred at 65° C. for 30 min. After cooling to room temperature, to this was added 2 M hydrochloric acid to stop reaction and extracted 3 times with ethyl acetate. The organic layer was washed with saturated brine and dried over anhydrous sodium sulfate. After removing anhydrous sodium sulfate by filtration, the filtrate was concentrated under reduced pressure with a rotary evaporator. The residue was purified by column chromatography (23 g, n-hexane/ethyl acetate=3/2) to give 3-benzyl-5-(4-hydroxyphenyl)-2-[(4-methylphenyl)sulfonylamino]pyrazine (coelentera-p-tosylamide) (c-35) as a yellow solid (155 mg, 37.1% (2 steps)). $R_f$=0.25 (n-hexane/ethyl acetate=3/2). Mp. 181-182.5° C. UV (MeOH) $\lambda_{max}$ (log ε) 336.5 (4.10), 291.5 (4.26), 277 (4.27). UV (pH 7.4 PB) $\lambda_{max}$ (log ε) 351 (4.14), 282.5 (4.37). $^1$H NMR (400 MHz, DMSO-$d_6$) δ 2.36 (s, 3H), 4.27 (s, 2H), 6.81 (d, J=8.7 Hz, 2H), 7.17-7.24 (m, 1H), 7.25-7.32 (m, 4H), 7.36 (d, J=7.6 Hz, 2H), 7.79 (t, J=8.7 Hz, 4H), 8.53 (s, 1H), 9.77 (s, 1H), 10.74 (s, 1H). IR (KBr, cm$^{-1}$) 474, 525, 546, 567, 610, 667, 698, 743, 816, 839, 876, 941, 1088, 1148, 1165, 1215, 1269, 1321, 1364, 1404, 1447, 1495, 1516, 1593, 1609, 3283. HRMS (FAB+) m/z 432.1382 (M+H, $C_{24}H_{22}N_3O_3S$ requires 432.1382).

Synthesis Example 20

5-(4-Acetoxyphenyl)-3-benzyl-2-bis(4-nitrophenylsulfonyl)aminopyrazine (c-40)

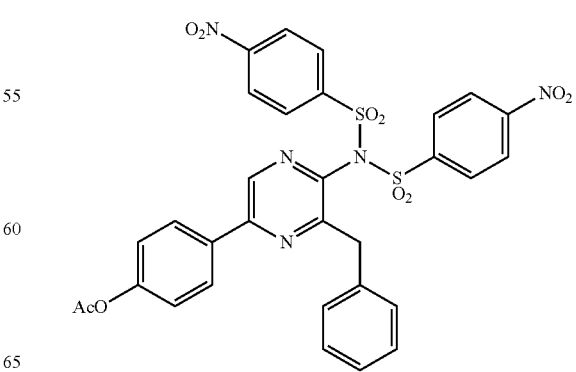

Under an argon atmosphere, 5-(4-acetoxyphenyl)-2-amino-3-benzylpyrazine (c-19) (140 mg, 438 µmol) was dissolved in pyridine (2 mL) and to this was added 4-(dimethylamino)pyridine (6.0 mg, 49 µmol). To this was added p-nitrobenzenesulfonyl chloride (293 mg, 1.32 mmol) while stirring at room temperature and stirred for 1.5 h at the same temperature. To this was further added p-nitrobenzenesulfonyl chloride (195 mg, 880 µmol) and stirred for 17 h. To this was added saturated aqueous solution of sodium bicarbonate to stop the reaction and the product was extracted twice with dichloromethane. The organic layer was washed once with water and once with saturated aqueous solution of sodium sulfate and then dried over anhydrous sodium sulfate. After removing anhydrous sodium sulfate by filtration, the filtrate was concentrated under reduced pressure. The residue was purified by column chromatography (24 g, n-hexane/ethyl acetate=4/1→3/1→7/3→ethyl acetate alone) to give 5-(4-acetoxyphenyl)-3-benzyl-2-bis(4-nitrophenylsulfonyl)aminopyrazine (c-40) as a dark brown solid (157 mg, 52.1%). $R_f$=0.62 (n-hexane/ethyl acetate=3/2). Mp. 227-229.5° C. (dec.). UV (MeOH, 0.3% DMSO) $\lambda_{max}$ (log ϵ) 309 (3.99), 258 (4.21). $^1$H NMR (400 MHz, DMSO-d$_6$) δ 2.30 (s, 3H), 4.22 (s, 2H), 7.19-7.27 (m, 1H), 7.29-7.35 (m, 6H), 8.05-8.10 (AA'BB', 4H), 8.14-8.19 (AA'BB', 2H), 8.39-8.44 (AA'BB', 4H), 9.13 (s, 1H). $^{13}$C NMR. (75.5 MHz, DMSO-d$_6$) δ 20.9, 38.0, 122.8 (2C), 124.8 (2C×2), 126.6, 128.3 (2C), 128.7 (2C), 129.6 (2C), 130.7 (2C×2), 131.9, 137.3, 139.8, 140.3, 142.1 (1C×2), 151.1 (1C×2), 151.9, 152.7, 156.2, 169.0. I,R (KBr, cm$^{-1}$) 548, 598, 617, 687, 737, 775, 810, 854, 880, 897, 916, 935, 1013, 1165, 1180, 1206, 1315, 1348, 1368, 1385, 1404, 1418, 1435, 1530, 1603, 1755, 3107. HRMS (FAR) m/z 690.0975 (M+H, C$_{31}$H$_{24}$N$_5$O$_{10}$S$_2$ requires 690.0965).

Synthesis Example 21

3-Benzyl-5-(4-hydroxyphenyl)-2-[(4-nitrophenyl)sulfonylamino]pyrazine (coelentera-p-nosylamide) (c-36)

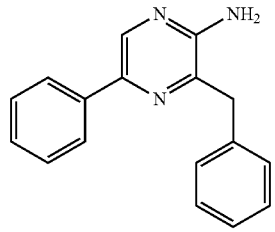

5-(4-Acetoxyphenyl)-3-benzyl-2-bis(4-nitrophenylsulfonyl)aminopyrazine (c-40) (151 mg, 219 µmol) was suspended in methanol (3 mL), and to this was added 10% (w/v) aqueous solution of sodium hydroxide aqueous (600 µL) while stirring at room temperature and then stirred at 65° C. for 30 min. To this were sequentially added methanol (1 mL) and 10% (w/v) aqueous solution of sodium hydroxide (400 µL) and stirred for an hour. After cooling to room temperature, to this was added 2 M hydrochloric to stop the reaction and extracted twice with ethyl acetate. The organic layer was washed with saturated brine and then dried over anhydrous sodium sulfate. After removing anhydrous sodium sulfate by filtration, the filtrate was concentrated under reduced pressure with a rotary evaporator. The residue was purified by column chromatography (8 g, n-hexane/ethyl acetate=3/2) to give 3-benzyl-5-(4-hydroxyphenyl)-2-[(4-nitrophenyl) sulfonylamino]pyrazine (coelentera-p-nosylamide) (c-36) as an orange solid (88.8 mg, 87.7%). $R_f$=0.13 (n-hexane/ethyl acetate=3/2). Mp. 176-177.5° C. (dec.). UV (MeOH) $\lambda_{max}$ (log ϵ) 338 (4.11), 276.5 (4.42). UV (pH 7.4 PB) $\lambda_{max}$ (log ϵ) 347 (4.15), 278.5 (4.49). $^1$H NMR (400 MHz, DMSO-d$_6$) δ 4.28 (s, 2H), 6.81 (d, J=8.7 Hz, 2H), 7.17-7.25 (m, 1H), 7.29 (s, 4H), 7.81 (d, J=8.6 Hz, 2H), 8.15 (d, J=8.6 Hz, 2H), 8.40 (d, J=8.4 Hz, 2H), 8.52 (s, 1H), 9.81 (s, 1H), 11.25 (s, 1H). IR (KBr, cm$^{-1}$) 633, 698, 748, 773, 827, 853, 970, 1084, 1121, 1231, 1263, 1277, 1350, 1395, 1501, 1514, 1528, 1611, 3227. HRMS (FAB$^+$) m/z 463.1086 (M+H, C$_{23}$H$_{19}$N$_4$O$_5$S requires 463.1076).

Synthesis Example 22

2-Amino-3-benzyl-5-phenylpyrazine (c-41)

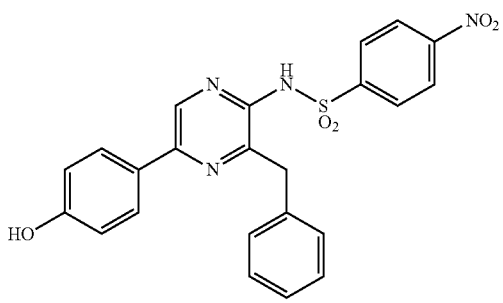 [SMILES: O=[N+]([O-])c1ccc(S(=O)(=O)Nc2ncc(-c3ccc(O)cc3)nc2Cc2ccccc2)cc1]

Under an argon atmosphere, 2-amino-3-benzyl-5-bromopyrazine (c-10) (1.66 g, 6.27 mmol) was dissolved in 1,2-dimethoxyethane (17 mL) and ethanol (13 mL) and to this were sequentially added 2 M aqueous solution of sodium carbonate (31.4 mL, 62.8 mmol), dichlorobis(triphenylphosphine) palladium(II) (221 mg, 315 µmol), and phenyl boronic acid (996 mg, 8.16 mmol) while stirring at room temperature and then stirred at 90° C. for 2.5 h. After cooling to room temperature, to this were added saturated brine and ethyl acetate to stop the reaction. The organic layer was washed with saturated brine and then dried over anhydrous sodium sulfate. After removing anhydrous sodium sulfate by filtration, the filtrate was concentrated under reduced pressure with a rotary evaporator. After purifying the residue by column chromatography (50 g, n-hexane/ethyl acetate=3/2→1/1), the obtained solid was recrystallized twice from ethyl acetate to give 2-amino-3-benzyl-5-phenylpyrazine (c-41) as a yellow solid (982 mg, 59.9%). $R_f$=0.30 (n-hexane/ethyl acetate=3/2). $^1$H NMR (400 MHz, DMSO-d$_6$) δ 4.07 (s, 2H), 6.41 (s, 2H), 7.18 (t, J=7.5 Hz, 1H), 7.24-7.31 (m, 3H), 7.34 (d, J=7.3 Hz, 2H), 7.40 (t, J=7.5 Hz, 2H), 7.90 (d, J=7.8 Hz, 2H), 8.41 (s, 1H). IR (KBr, cm$^{-1}$) 596, 664, 694, 716, 733, 754, 773, 908, 937, 1070, 1152, 1217, 1233, 1396, 1427, 1450, 1462, 1493, 1543, 1636, 3024, 3125, 3291, 3487. HRMS (EI$^+$) m/z 261.1269 (M, C$_{17}$H$_{15}$N$_3$ requires 261.1266).

Synthesis Example 23

3-Benzyl-2-bis(benzylsulfonyl)amino-5-phenylpyrazine (c-42)

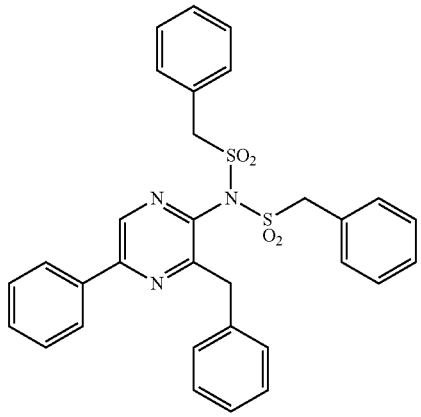 [SMILES: O=S(=O)(Cc1ccccc1)N(c1ncc(-c2ccccc2)nc1Cc1ccccc1)S(=O)(=O)Cc1ccccc1]

Under an argon atmosphere, 2-amino-3-benzyl-5-phenylpyrazine (c-41) (852 mg, 3.26 mmol) was dissolved in anhydrous dichloromethane (25 mL), and to this was added triethylamine (1.38 mL, 9.87 mmol), and cooled to 0° C. To this was added benzylsulfonyl chloride (1.87 g, 9.80 mmol) and stirred for 23.5 h after warming to room temperature. To this was added 2 M hydrochloric acid to stop the reaction and after separating the aqueous layer and organic layer, the organic layer was washed once with water and once with saturated hydrochloric acid and then dried over anhydrous sodium sulfate. After removing anhydrous sodium sulfate by filtration, the filtrate was concentrated under reduced pressure with a rotary evaporator. The residue was purified by silica gel column chromatography (56 g, n-hexane/ethyl acetate=4/1) to give 3-benzyl-2-bis(benzylsulfonyl)amino-5-phenylpyrazine (c-42) as a reddish orange amorphous (1.27 g, 68.2%). $R_f$=0.70 (n-hexane/ethyl acetate=3/2). Mp. 71.5-74.5° C. UV (MeOH) $\lambda_{max}$ (log $\epsilon$) 304 (4.20), 257 (4.15). UV (pH 7.4 PB) $\lambda_{max}$ (log $\epsilon$) 331 (4.13), 269 (4.12). $^1$H NMR (400 MHz, DMSO-d$_6$) δ 3.89 (s, 2H), 5.00 (s, 1H), 5.04 (s, 1H), 5.19 (s, 1H), 5.22 (s, 1H), 7.15 (d, J=7.0 Hz, 2H), 7.18-7.24 (m, 1H), 7.25-7.32 (m, 2H), 7.38-7.46 (m, 10H), 7.50-7.55 (m, 3H), 8.04-8.10 (m, 2H), 9.21 (s, 1H). $^{13}$C NMR (75.5 MHz, DMSO-d$_6$/CD$_3$OD=2/1) δ 38.5, 61.7 (1C×2), 127.0, 127.5, 127.8 (1C×2), 128.8 (2C), 129.4 (2C×2), 129.7 (2C), 129.9 (2C), 130.2 (2C), 131.3, 132.2 (2C), 135.3, 138.3, 139.6, 142.0, 153.0, 156.5. IR (KBr, cm$^{-1}$) 507, 538, 557, 611, 629, 694, 723, 748, 766, 779, 876, 920, 1144, 1163, 1252, 1354, 1375, 1427, 1454, 1495, 1530, 3032. HRMS (FAB$^+$) m/z 570.1526 (M+H, C$_{31}$H$_{28}$N$_3$O$_4$S$_2$ requires 570.1521).

Synthesis Example 24

3-Benzyl-2-benzylsulfonylamino-5-phenylpyrazine (dideoxycoelenterasulfonamide) (c-37)

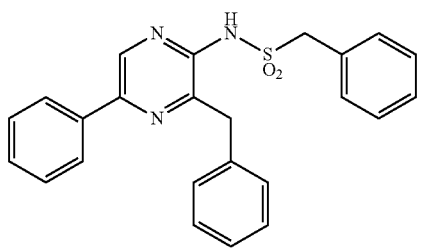 [SMILES: O=S(=O)(Cc1ccccc1)Nc1ncc(-c2ccccc2)nc1Cc1ccccc1]

3-Benzyl-2-bis(benzylsulfonyl)amino-5-phenylpyrazine (c-42) (1.15 g, 2.02 mmol) was suspended in methanol (24 mL), and to this was added 10% (w/v) aqueous solution of sodium hydroxide (5.7 mL) while stirring at room temperature and then stirred at 65° C. for 30 min. After cooling to room temperature, to this was added 2 M hydrochloric acid to stop the reaction and extracted twice with ethyl acetate. The organic layer was washed with saturated brine and then dried over anhydrous sodium sulfate. After removing anhydrous sodium sulfate by filtration, the filtrate was concentrated under reduced pressure with a rotary evaporator. The residue was recrystallized from ethyl acetate to give 3-benzyl-2-benzylsulfonylamino-5-phenylpyrazine (dideoxycoelenterasulfonamide) (c-37) as a colorless solid (662 mg, 78.9%). $R_f$=0.62 (n-hexane/ethyl acetate=3/2). Mp. 207-208.5° C. UV (MeOH, 0.3% DMSO) $\lambda_{max}$ (log $\epsilon$) 322.5 (4.01), 285.5 (4.08), 261 (4.14). UV (pH 7.4 PB, 0.3% DMSO) $\lambda_{max}$ (log $\epsilon$) 343 (4.01), 280.5 (4.07). $^1$H NMR (400 MHz, DMSO-d$_6$) δ 4.26 (s, 2H), 4.94 (s, 2H), 7.15-7.21 (m, 1H), 7.23-7.30 (m, 4H), 7.36 (s, 5H), 7.40-7.53 (m, 3H), 8.04 (d, J=7.0 Hz, 2H), 8.95 (s, 1H), 10.55 (s, 1H). $^{13}$C NMR (75.5 MHz, DMSO-d$_6$/CD$_3$OD=2/1) δ 38.5, 60.1, 126.7 (2C), 126.8, 128.8 (2C), 128.9, 129.0 (2C), 129.4 (2C), 129.5 (2C), 129.7, 130.4, 131.4 (2C), 136.3, 137.3, 138.5, 145.8, 146.3, 146.6. IR (KBr, cm$^{-1}$) 447, 515, 532, 546, 615, 664, 692, 748, 783, 889, 1117, 1157, 1179, 1323, 1400, 1425, 1450, 1495, 3034, 3267. HRMS (FAB$^+$) m/z 416.1429 (M+H, C$_{24}$H$_{22}$N$_3$O$_2$S requires 416.1433).

Synthesis Example 25

3-Benzyl-5-(4-methoxyphenyl)-2-[(4-methoxyphenyl)thioacetylamino]pyrazine (c-44)

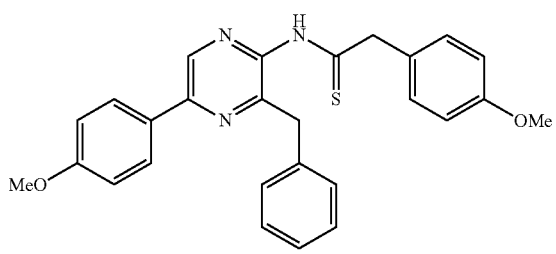 [SMILES: COc1ccc(CC(=S)Nc2ncc(-c3ccc(OC)cc3)nc2Cc2ccccc2)cc1]

Under an argon atmosphere, 3-benzyl-5-(4-methoxyphenyl)-2-[(4-methoxyphenyl)acetylamino]pyrazine (c-43) (prepared by the method described in Inouye, S. & Hosoya, T., Biochem. Biophys. Res. Commun., 386, 617-622 (2009)) (1.00 g, 2.28 mmol) was suspended in anhydrous toluene (30 mL) and to this was added Lawesson's reagent (552 mg, 1.37 mmol) while stirring at room temperature, and then heated to reflux for 17 h. After refluxing, it was cooled to room temperature, and concentrated under reduced pressure with a rotary evaporator. The residue was purified by silica gel column chromatography (100 g, dichloromethane/ethyl acetate=49/1) to give 3-benzyl-5-(4-methoxyphenyl)-2-[(4-methoxyphenyl)thioacetylamino]pyrazine (c-44) as a yellow oily substance (823 mg, 79.4%). $R_f$=0.43 (dichloromethane/ethyl acetate=19/1). $^1$H NMR (400 MHz, DMSO-d$_6$) δ 2.84 (s, 3H), 3.82 (s, 3H), 3.92 (s, 2H), 4.07 (s, 2H), 6.90-6.96

(AA'BB', 2H), 6.98-7.04 (AA'BB', 2H), 7.05-7.11 (AA'BB', 2H), 7.13-7.26 (m, 3H), 7.38-7.50 (m, 2H), 8.06-8.11 (AA'BB', 2H), 8.99 (s, 1H), 12.12 (s, 1H). $^{13}$C NMR (67.8 MHz, DMSO-d$_6$) δ 39.3, 50.8, 55.0, 55.3, 113.8 (2C), 114.5 (2C), 126.3, 127.6, 128.18 (2C), 128.21 (2C), 128.8, 128.9 (2C), 130.0 (2C), 137.8, 138.0, 145.0, 149.6, 152.1, 158.4, 160.8, 205.1. IR (KBr, cm$^{-1}$) 704, 835, 1030, 1113, 1175, 1250, 1292, 1304, 1319, 1371, 1422, 1439, 1493, 1510, 1607, 2835, 2932, 2957, 3150. HRMS (ESI$^+$) m/z 456.1747 ((M+H)$^+$, C$_{27}$H$_{26}$N$_3$O$_2$S$^+$ requires 456.1740).

Synthesis Example 26

3-Benzyl-5-(4-hydroxyphenyl)-2-[(4-hydroxyphenyl)thioacetylamino]pyrazine (coelenterathioamide) (c-45)

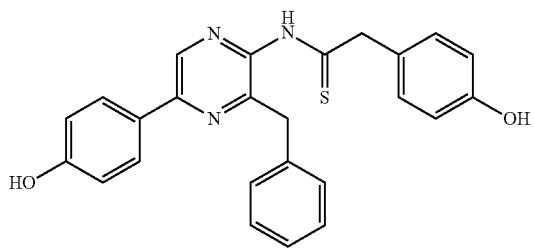 [SMILES: Oc1ccc(CC(=S)Nc2ncc(-c3ccc(O)cc3)nc2Cc2ccccc2)cc1]

Under an argon atmosphere, 3-benzyl-5-(4-methoxyphenyl)-2-[(4-methoxyphenyl)thioacetylamino]pyrazine (c-44) (823 mg, 1.81 mmol) was dissolved in anhydrous dichloromethane (30 mL) and to this was added 1.0 M solution of boron tribromide in dichloromethane (6.80 mL, 6.80 mmol) at room temperature and heated to reflux for 21 h. After cooling to room temperature, to this was added saturated aqueous solution of sodium bicarbonate and concentrated under reduced pressure with a rotary evaporator to remove dichloromethane. The resulting suspension was filtrated and the residue was dried to give the crude product (591 mg) as a red solid. The crude product was dissolved in ethyl acetate and to this was added n-hexane to form a precipitate. The solid was collected by filtration and dried in vacuo to give 3-benzyl-5-(4-hydroxyphenyl)-2-[(4-hydroxyphenyl)thioacetylamino]pyrazine (coelenterathioamide) (c-45) as an orange solid (514 mg, 66.6%). R$_f$=0.23 (n-hexane/ethyl acetate=1/1). Mp. 101-103° C. $^1$H NMR (400 MHz, DMSO-d$_6$) δ 3.90 (s, 2H), 4.00 (s, 2H), 6.71-6.77 (AABB', 2H), 6.85-6.91 (AA'BB', 2H), 6.97-7.03 (AA'BB', 2H), 7.12-7.25 (m, 3H), 7.27-7.34 (m, 2H), 7.94-8.00 (AA'BB', 2H), 8.91 (s, 1H), 9.34 (s, 1H), 9.94 (s, 1H), 12.05 (s, 1H). $^{13}$C NMR (67.8 MHz, DMSO-d$_6$) δ 50.9, 115.1 (2C), 115.8 (2C), 126.0, 126.2, 127.0, 128.18 (2C), 128.24 (2C), 128.9 (2C), 129.9 (2C), 137.4, 138.0, 144.6, 149.9, 152.0, 156.4, 159.3, 205.3 (one carbon at benzyl position was unobservable due to overlapping with septet peak of DMSO). IR (KBr, cm$^{-1}$) 515, 561, 706, 731, 837, 908, 935, 1063, 1130, 1171, 1238, 1315, 1371, 1443, 1514, 1609, 2808, 3026, 3159. HRMS (ESI$^+$) m/z 428.1434 ((M+H)$^+$, C$_{25}$H$_{22}$N$_3$O$_2$S$^+$ requires 428.1427).

Synthesis Example 27

5-(4-Acetoxyphenyl)-3-benzyl-2-bis(4-iodobenzylsulfonyl)aminopyrazine (c-46)

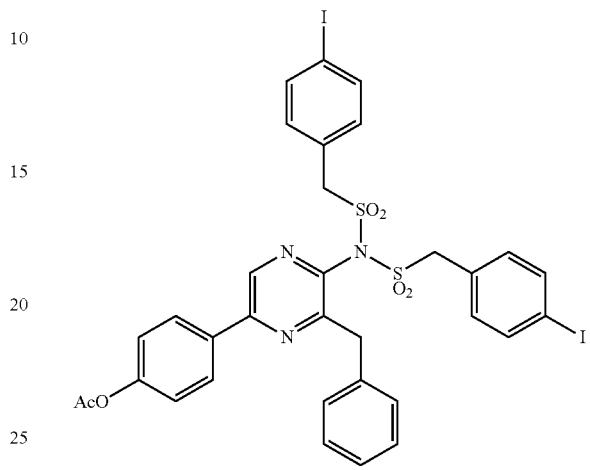

Under an argon atmosphere, 5-(4-acetoxyphenyl)-2-amino-3-benzylpyrazine (c-19) (681 mg, 2.13 mmol) was dissolved in anhydrous dichloromethane (40 mL), and to this was added triethylamine (1.20 mL, 8.53 mmol), and cooled to 0° C. To this was added 4-iodobenzylsulfonyl chloride (prepared by the method described in Liu, S. et al., Org. Lett., 3, 1571-1574 (2001)) (2.70 g, 8.53 mmol), and heated to reflux for 26 h after warming to room temperature. After cooling to room temperature, to this were added 2 M hydrochloric acid and dichloromethane and after separating the aqueous layer and organic layer, the organic layer was washed once with water and once with saturated brine, and dried over anhydrous sodium sulfate. After removing anhydrous sodium sulfate by filtration, the filtrate was concentrated under reduced pressure with a rotary evaporator. The residue was purified by silica gel column chromatography (100 g, n-hexane/ethyl acetate=4/1), to the obtained product was added dichloromethane, and filtered to remove insolubles. After this procedure was repeated 5 times, the filtrate was concentrated under reduced pressure with a rotary evaporator. The residue was recrystallized from ethyl acetate to give 5-(4-acetoxyphenyl)-3-benzyl-2-bis(4-iodobenzylsulfonyl)aminopyrazine (c-46) as a colorless solid (597 mg, 31.8%). R$_f$=0.21 (n-hexane/ethyl acetate=4/1). Mp. 166-167° C. $^1$H NMR. (400 MHz, DMSO-d$_6$) δ 2.30 (s, 3H), 3.89 (s, 2H), 5.00 (d, 2H, J=13.6 Hz), 5.19 (d, 2H, J=13.6 Hz), 7.11-7.17 (AA'BB', 2H), 7.19-7.34 (m, 9H), 7.78-7.83 (AA'BB', 4H), 8.07-8.15 (AA'BB', 2H), 9.19 (s, 1H). $^{13}$C NMR (67.8 MHz, DMSO-d$_6$) δ 20.9, 37.5, 60.5 (2C), 96.3, 126.4, 126.5 (2C), 128.1 (2C), 128.5 (2C), 129.5 (2C), 132.0, 133.6 (4C), 137.4, 137.7 (4C), 139.2, 140.9, 151.2, 152.5, 155.5, 168.9. IR (KBr, cm$^{-1}$) 519, 575, 627, 704, 775, 835, 912, 1013, 1057, 1159, 1200, 1254, 1356, 1377, 1483, 1601, 1757. Anal. Calcd. For C$_{33}$H$_{27}$I$_2$N$_3$O$_6$S$_2$: C, 45.06; H, 3.09; N, 4.78. Found: C, 45.18; H, 3.24; N, 4.78.

Synthesis Example 28

5-(4-Acetoxyphenyl)-3-benzyl-2-[(4-hydroxybenzyl)sulfonylamino]pyrazine (c-48)

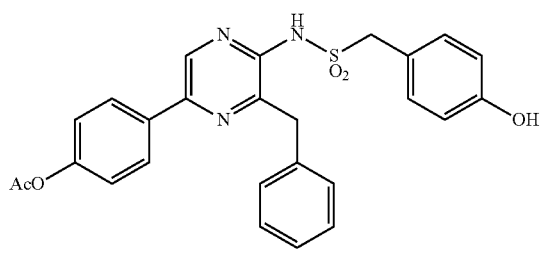 [SMILES: CC(=O)Oc1ccc(-c2cnc(NS(=O)(=O)Cc3ccc(O)cc3)c(Cc3ccccc3)n2)cc1]

Under an argon atmosphere, 5-(4-acetoxyphenyl)-3-benzyl-2-bis(4-iodobenzylsulfonyl)aminopyrazine (c-46) (402 mg, 457 μmol) was dissolved in dimethylsulfoxide (DMSO) (4 mL) and to this were sequentially added bis(pinacolato)diboron (284 mg, 1.12 mmol), potassium acetate (236 mg, 2.41 mmol), and [1,1'-bis(diphenylphosphino)ferrocene]dichloropalladium(II) dichloromethane complex (1:1) (32.7 mg, 40.1 μmol) at room temperature and then stirred at 80° C. for 18 h. After cooling to room temperature, to this was added water and extracted 3 times with ethyl acetate. The organic layer was washed 3 times with water and once with saturated brine, and then dried over anhydrous sodium sulfate. After removing anhydrous sodium sulfate by filtration, the filtrate was concentrated under reduced pressure. The residue was purified by silica gel column chromatography (50 g, n-hexane/ethyl acetate=2/1) to give a mixture of 5-(4-acetoxyphenyl)-3-benzyl-2-[4-{4-(4,4,5,5-tetramethyl-1,3,2-dioxaboran-2-yl)benzyl}sulfonylamino]pyrazine (c-47) and 5-(4-acetoxyphenyl)-3-benzyl-2-[(4-iodobenzyl)sulfonylamino]pyrazine.

The mixture obtained above was dissolved in acetone (10 mL), and to this was added a solution of oxone (247 mg, 401 μmol) in water (3 mL) at room temperature and stirred for 15 min at the same temperature. To this was added saturated aqueous solution of sodium bicarbonate to stop the reaction and extracted 3 times with dichloromethane. The organic layer was washed once with water and once with saturated brine, and then dried over anhydrous sodium sulfate. After removing anhydrous sodium sulfate by filtration, the filtrate was concentrated under reduced pressure with a rotary evaporator. The residue was purified by silica gel column chromatography (50 g, n-hexane/ethyl acetate=2/1, and 50 g, n-hexane/ethyl acetate=3/2) to give a colorless solid (68.5 mg), which was dissolved in ethyl acetate, followed by addition of n-hexane to form a precipitate. The precipitated solid was collected by filtration and dried in vacuo to give 5-(4-acetoxyphenyl)-3-benzyl-2-[(4-hydroxybenzyl)sulfonylamino]pyrazine (c-48) as a colorless solid (44.8 mg, 20.0%, 2 steps). $R_f$=0.45 (n-hexane/ethyl acetate=1/1). $^1$H NMR (400 MHz, DMSO-$d_6$) δ 2.30 (s, 3H), 4.26 (s, 2H), 4.81 (s, 2H), 6.68-6.79 (AA'BB', 2H), 7.08-7.32 (m, 9H), 8.02-8.14 (AA'BB', 2H), 8.94 (s, 1H), 9.55 (s, 1H), 10.45 (s, 1H). $^{13}$C NMR (67.8 MHz, DMSO-$d_6$) δ 20.9, 37.9, 59.1, 115.3 (2C), 119.8, 122.4 (2C), 126.3, 127.2 (2C), 128.3 (2C), 128.9 (2C), 132.0 (2C), 133.3, 136.8, 137.9, 145.0, 145.4, 145.5, 151.3, 157.7, 169.1. IR (KBr, cm$^{-1}$) 536, 598, 702, 841, 891, 920, 1015, 1153, 1204, 1233, 1327, 1373, 1422, 1454, 1514, 1599, 1746, 3269.

Synthesis Example 29

3-Benzyl-2-(4-hydroxybenzyl)sulfonylamino-5-(4-hydroxyphenyl)pyrazine (coelenterasulfonamide) (c-38)

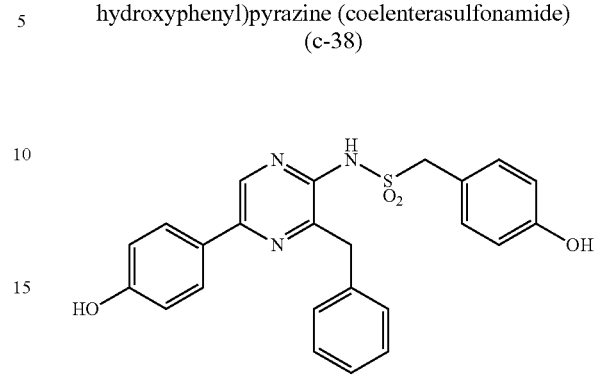

5-(4-Acetoxyphenyl)-3-benzyl-2-[(4-hydroxybenzyl)sulfonylamino]pyrazine (c-48) (105 mg, 214 μmol) was dissolved in methanol (2 mL) and to this was added 10% (w/v) aqueous solution of sodium hydroxide (1.0 mL) while stirring at room temperature and then stirred at 60° C. for 2 h. After cooling to room temperature, to this was added 2 M hydrochloric acid to stop the reaction, and extracted 3 times with ethyl acetate. The organic layer was washed with saturated brine and then dried over anhydrous sodium sulfate. After removing a anhydrous sodium sulfate by filtration, the filtrate was concentrated under reduced pressure with a rotary evaporator. The residue was purified by column chromatography (10 g, n-hexane/ethyl acetate=1/1). Recrystallization from n-hexane/ethyl acetate gave 3-benzyl-2-(4-hydroxybenzyl)sulfonylamino-5-(4-hydroxyphenyl)pyrazine (coelenterasulfonamide) (c-38) as a yellow solid (43.4 mg, 45.2%). $R_f$=0.29 (n-hexane/ethyl acetate=1/1). Mp. 194.5-196.5° C. $^1$H NMR (400 MHz, DMSO-$d_6$) δ 4.22 (s, 2H), 4.78 (s, 2H), 6.70-6.77 (AA'BB', 2H), 6.83-6.90 (AA'BB', 2H), 7.10-7.21 (m, 3H), 7.23-7.31 (m, 4H), 7.85-7.95 (AA'BB', 2H), 8.81 (s, 1H), 9.54 (s, 1H), 9.81 (s, 1H), 10.30 (s, 1H). $^{13}$C NMR. (67.8 MHz, DMSO-$d_6$) δ 38.0, 59.1, 115.4 (2C), 115.8 (2C), 119.9, 126.3, 126.6, 127.7 (2C), 128.3 (2C), 129.0 (2C), 132.0 (2C), 135.9, 138.2, 144.4, 145.7, 146.4, 157.7, 158.8. IR (KBr, cm$^{-1}$) 536, 602, 700, 835, 889, 1119, 1155, 1177, 1258, 1275, 1327, 1402, 1456, 1514, 1611, 3529, 3412, 3487. Anal. Calcd. For $C_{24}H_{21}N_3O_4S$: C, 64.41; H, 4.73; N, 9.39. Found: C, 64.28; H, 4.74; N, 9.28.

3. Determination of Fluorescence Properties

Example 1

The fluorescence quantum yield of each CTMD analog synthesized was determined by the following procedure. The fluorescence spectrum was measured at 25° C. using a spectrofluorometer FP-6500 of JASCO (JASCO Corp., Tokyo). Specifically, the CTMD analog was dissolved in methanol (MeOH) or in 67 mM phosphate buffer (PB) (pH 7.4) at a final concentration of 750 nM using a quartz cell (light path length of 10 mm). Measurement was performed 3 times at the excited wavelength of 330 nm, emission/excitation band width of 3 nm, response of 0.5 second and scanning rate of 100 nm/min. The average was taken as the fluorescence spectrum of the compound. The fluorescence quantum yield was determined after the spectrum was corrected.

Quinine sulfate was used as a standard for determining the fluorescence quantum yield. After quinine sulfate (Wako Pure Chemical Industries) was dissolved in 0.1N sulfuric acid aqueous solution, measurement was performed at the excitation light of 366 nm under the conditions for fluorescence measurements described above. The relative fluorescence quantum yield (fluorescence intensity) of the compound was calculated relative to the quantum yield of quinine sulfate as being 0.55.

nM. When the final concentration was 750 nM as in EXAMPLE 1, any fluorescence spectrum was not detected for c-14, c-31 and c-36 both in methanol and in a phosphate buffer, and not detected for c-25 in a phosphate buffer, in coelenteramide analogs of the present invention (n.d.: not detected). With respect to c-14, c-31, c-25 and c-36 that no fluorescence spectrum was detected, fluorescence spectra were measured under the same conditions as in EXAMPLE 1 except that the final concentration of these coelenteramide analogs was 30 μM. In a similar method, the fluorescence spectrum for C-4 was also measured at a final concentration

TABLE 1

| No. | Compound | $\lambda_{max}$ (MeOH)/nm | Fluorescence quantum yield (MeOH) | $\lambda_{max}$ (PB)/nm | Fluorescence quantum yield (PB) |
|---|---|---|---|---|---|
| c-4 | CTMD | 427.5 | 0.012 | 451 | 0.001 |
| c-29 | O—Ac2-CTMD | 376.5 | 0.086 | 386.5 | 0.029 |
| c-13 | hCTMD | 424.5 | 0.010 | 399 | 0.003 |
| c-16 | O—Me-hCTMD | 415 | 0.342 | 450 | 0.181 |
| c-30 | O—Ac-hCTMD | 373.5 | 0.008 | 391 | 0.040 |
| c-14 | hCTTD | n.d. | n.d. | n.d. | n.d. |
| c-17 | O—Me-hCTTD | 417.5 | 0.003 | 445 | 0.003 |
| c-31 | O—Ac-hCTTD | n.d. | n.d. | n.d. | n.d. |
| c-15 | hCTSD | 429.5 | 0.066 | 435.5 | 0.137 |
| c-18 | O—Me-hCTSD | 416.5 | 0.293 | 429 | 0.147 |
| c-32 | O—Ac-hCTSD | 404 | 0.234 | 420 | 0.239 |
| c-25 | CTAD | 425.5 | 0.009 | 446.5 | n.d. |
| c-24 | O—Me-CTAD | 415.5 | 0.345 | 450.5 | 0.199 |
| c-33 | O—Ac-CTAD | 375 | 0.085 | 384 | 0.154 |
| c-21 | O—Me-hCTdiSD | 417 | 0.303 | 421.5 | 0.059 |
| c-20 | O—Ac-hCTdiSD | 399.5 | 0.185 | 420 | 0.026 |
| c-39 | O—Ac-CTdiMsD | 381.5 | 0.079 | 419 | 0.096 |
| c-34 | CTMsD | 429 | 0.056 | 437 | 0.096 |
| c-35 | CTpTsD | 430.5 | 0.069 | 435 | 0.107 |
| c-42 | deoxy-hCTdiSD | 398.5 | 0.180 | 420.5 | 0.011 |
| c-37 | dideoxy-CTSD | 402.5 | 0.196 | 419.5 | 0.227 |
| c-40 | O—Ac-CTdipNsD | 407.5 | 0.004 | 415 | 0.021 |
| c-36 | CTpNsD | n.d. | n.d. | n.d. | n.d |
| | quinine/0.1N $H_2SO_4$ | 451 | 0.55 | 451 | 0.55 | ex. 366 nm

From TABLE 1, it was found that the coelenteramide analog of the present invention (c-14, c-17, c-31, c-15, c-18, c-32, c-21, c-20, c-39, c-34, c-35, c-42, c-37, c-40 or c-36) has different fluorescence properties from those of known CTMD (c-4) or h-CTMD (c-13).

In coelenteramide analogs of the present invention, c-15, c-18, c-32, c-21, c-20, c-39, c-34, c-35, c-42 and c-37 showed the fluorescence quantum yield of 0.090 or more in an organic solvent or in an aqueous solution, indicating that they showed a strong fluorescence intensity. In particular, c-15, c-18, c-32, c-21, c-20, c-35, c-42 or c-37 showed the fluorescence quantum yield of 0.100 or more in an organic solvent or an aqueous solution and was found to have especially strong fluorescence intensity.

It is also known that the fluorescence intensity in the most fluorescent compounds is markedly diminished in an aqueous solution even if they have strong fluorescence intensity in an organic solvent. It was found that especially c-18, c-32 or c-37 showed the fluorescence quantum yield of 0.100 or more both in an organic solvent and in an aqueous solution, and retained particularly strong fluorescence intensity.

Example 2

The fluorescence quantum yield determined in EXAMPLE 1 was estimated by measuring the fluorescence spectra when the final concentration of coelenteramide analogs was 750 of 30 μM. The fluorescence spectrum also for c-45 was measured in 50 mM Tris-HCl (pH 7.6) containing 10 mM $CaCl_2$ under the same conditions as in EXAMPLE 1 except that the final concentration was 18 μM.

Figure 2:
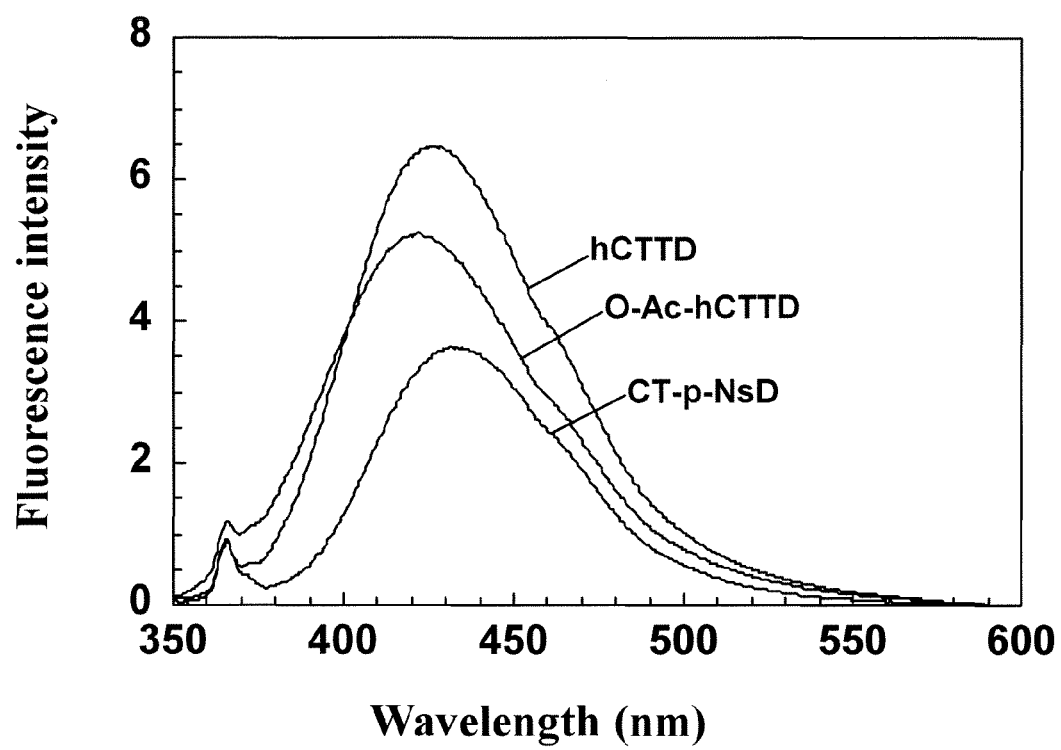
FIG. 2 shows the fluorescence spectra of coelenteramide analogs in methanol at a final concentration of 30 µM (EXAMPLE 2).
Figure 3:
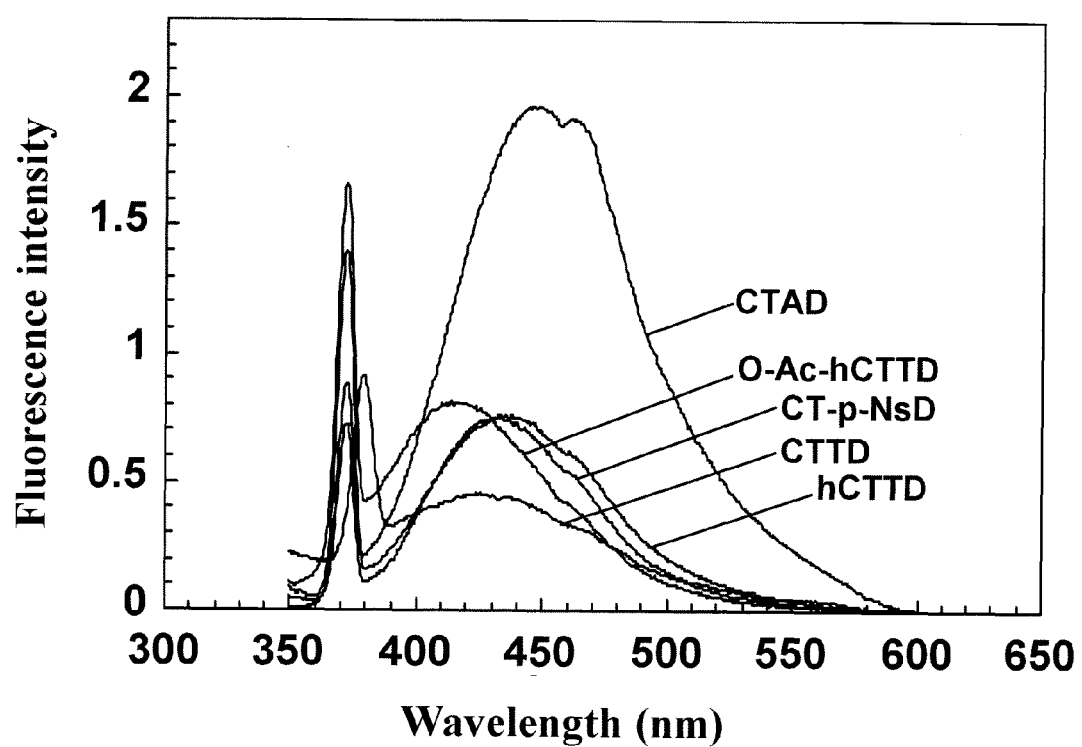
FIG. 3 shows the fluorescence spectra of coelenteramide analogs in a phosphate buffer at a final concentration of 30 µM (EXAMPLE 2).

The fluorescence spectra of c-14 (hCTTD), c-31 (O-Ac-h-CTTD) and c-36 (CT-p-NsD) in methanol are shown in FIG. 2. The fluorescence spectra of c-14 (hCTTD), c-31 (O-Ac-h-CTTD), C-25 (CTAD) and c-36 (CT-p-NsD) in the phosphate buffer are shown in FIG. 3. The fluorescence spectra of c-45 (CTTD) in 50 mM Tris-HCl (pH 7.6) containing 10 mM $CaCl_2$ are also shown in FIG. 3.

Furthermore, the fluorescence spectrum data of c-4, c-14, c-31, c-25 and c-36 are summarized in TABLE 2.

TABLE 2

| No. | Compound | $\lambda_{max}$ (MeOH)/nm | Fluorescence Intensity (MeOH) | $\lambda_{max}$ (PB)/nm | Fluorescence Intensity (PB) |
|---|---|---|---|---|---|
| c-4 | CTMD | 428.0 | 80.0 | 444.5 | 1.7 |
| c-14 | hCTTD | 428.0 | 6.5 | 435.5 | 1.4 |
| c-31 | O—Ac-hCTTD | 422.0 | 5.2 | 413.5 | 1.7 |
| c-25 | CTAD | — | — | 446.0 | 2.0 |
| c-36 | CT-p-NsD | 433.0 | 3.6 | 433.5 | 0.8 |

The results reveal that coelenteramide analogs of the present invention including c-14, c-31 and c-36 show the fluorescence intensity in an organic solvent and in an aqueous solution. Furthermore, it could be confirmed that c-45 had the fluorescence ability at least in an aqueous solution.

Since c-17 (hCTTD) was found to be the fluorescence intensity, it was considered that c-44 (CTTD) would have the fluorescence ability as in c-17.

As shown in EXAMPLES above, coelenteramide analogs of the present invention in the preferred embodiments have the fluorescence ability both in an organic solvent and in an aqueous solution and can be applied to a wide variety of usages such as bioassays, intramolecular imaging, etc.

Example 3

The fluorescence spectrum of c-38 was measured at 25° C. using a JASCO spectrofluorometer FP-6500 (JASCO Corp., Tokyo). Specifically, c-38 was dissolved in 50 mM Tris-HCl (pH 7.6) containing 10 mM $CaCl_2$ at a final concentration of 18 μM using a quartz cell (light path length of 10 mm). Measurement was performed 3 times at the excited wavelength of 330 nm, emission/excitation band width of 3 nm, response of 0.5 second and scanning rate of 100 nm/min. The average was taken as the fluorescence spectrum.

Figure 4:
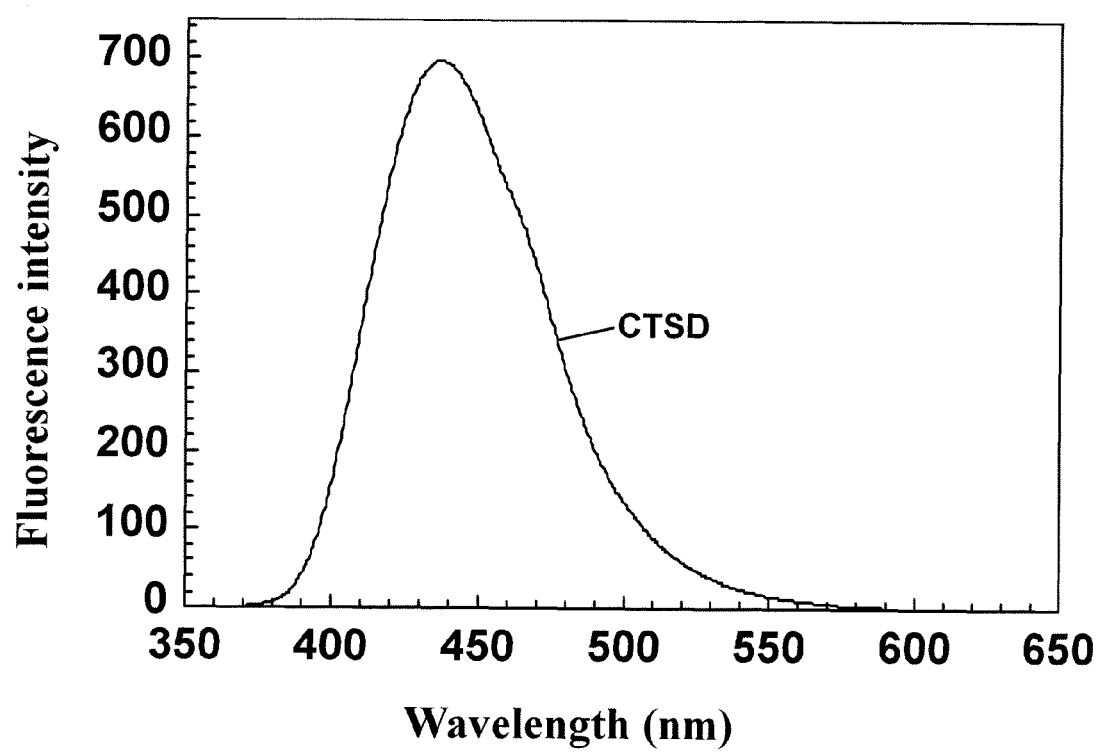
FIG. 4 shows the fluorescence spectrum of the c-38 compound (CTSD) in 50 mM Tris-HCl (pH7.6) containing 10 mM CaCl₂ at a final concentration of 18 µM (EXAMPLE 3).

The fluorescence spectrum of c-38 (CTSD) in 50 mM Tris-HCl (pH 7.6) containing 10 mM $CaCl_2$ is shown in FIG. 4.

FIG. 4 reveals that c-38 has the fluorescence capacity.

SEQUENCE LISTING FREE TEXT

[SEQ ID NO: 1] Nucleotide sequence of natural apoaequorin.
[SEQ ID NO: 2] Amino acid sequence of natural apoaequorin.
[SEQ ID NO: 3] Nucleotide sequence of natural apoclytin-I.
[SEQ ID NO: 4] Amino acid sequence of natural apoclytin-I.
[SEQ ID NO: 5] Nucleotide sequence of natural apoclytin-II.
[SEQ ID NO: 6] Amino acid sequence of natural apoclytin-II.
[SEQ ID NO: 7] Nucleotide sequence of natural apomitrocomin.
[SEQ ID NO: 8] Amino acid sequence of natural apomitrocomin.
[SEQ ID NO: 9] Nucleotide sequence of natural apobelin.
[SEQ ID NO: 10] Amino acid sequence of natural apobelin.
[SEQ ID NO: 11] Nucleotide sequence of natural apobervoin.
[SEQ ID NO: 12] Amino acid sequence of natural apobervoin.

The invention claimed is:

1. A compound represented by general formula (1) below:

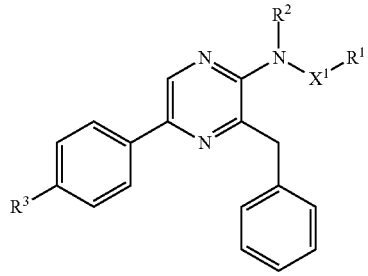

(1)

wherein:
R$^1$ is a substituted or unsubstituted aryl, a substituted or unsubstituted arylalkyl, a straight or branched alkyl which may optionally be substituted with an alicyclic group, an alicyclic group or a heterocyclic group;

R$^2$ is hydrogen or —(SO$_2$)R$^4$;

R$^3$ is hydrogen, hydroxy, methoxy or acetoxy;

R$^4$ is a substituted or unsubstituted aryl, a substituted or unsubstituted arylalkyl, or a straight or branched alkyl which may optionally be substituted with an alicyclic group; and, X$^1$ is —C(=S)— or —SO$_2$—.

2. The compound according to claim 1, wherein R$^1$ in the general formula (1) is phenyl, p-methylphenyl, p-hydroxyphenyl, p-methoxyphenyl, p-acetoxyphenyl, p-nitrophenyl, benzyl, α-hydroxybenzyl, 4-methylbenzyl, 4-hydroxybenzyl, 4-methoxybenzyl, 4-acetoxybenzyl, 4-nitrobenzyl, phenylethyl, methyl, ethyl, propyl, 2-methylpropyl, 2-methylpropanyl, cyclohexylmethyl, cyclohexylethyl, adamantylmethyl, cyclopentylmethyl, cyclohexyl or thiophen-2-yl.

3. The compound according to claim 1, wherein R$^2$ in the general formula (1) is hydrogen, benzenesulfonyl, p-toluenesulfonyl, 4-hydroxyphenylsulfonyl, 4-methoxyphenylsulfonyl, 4-acetoxyphenylsulfonyl, 4-nitrophenylsulfonyl, benzylsulfonyl, α-hydroxybenzylsulfonyl, 4-methylbenzylsulfonyl, 4-hydroxybenzylsulfonyl, 4-methoxybenzylsulfonyl, 4-acetoxybenzylsulfonyl, 4-nitrobenzylsulfonyl, phenylethylsulfonyl, methanesulfonyl, ethylsulfonyl, propylsulfonyl, 2-methylpropylsulfonyl, 2-methylpropanylsulfonyl, cyclohexylmethylsulfonyl, cyclohexylethylsulfonyl, adamantylmethylsulfonyl or cyclopentylmethylsulfonyl.

4. The compound according to claim 1, which is selected from the group consisting of the compounds described below:

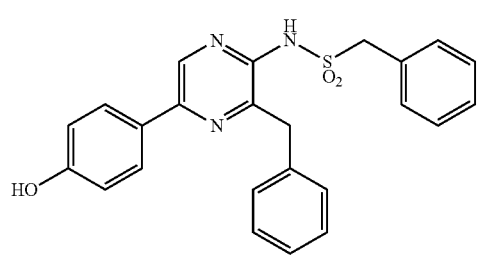

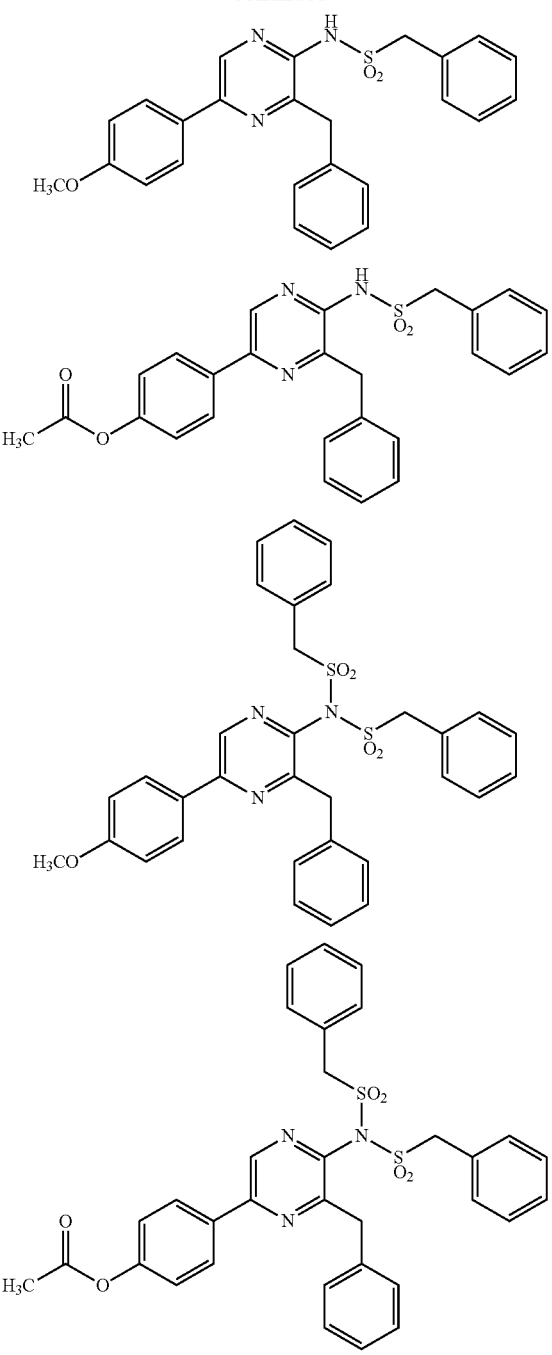

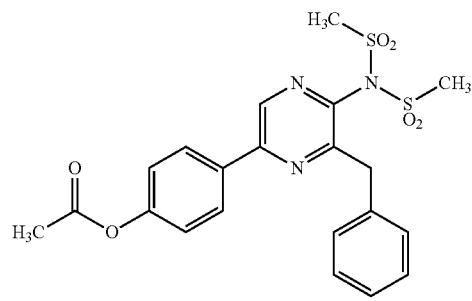

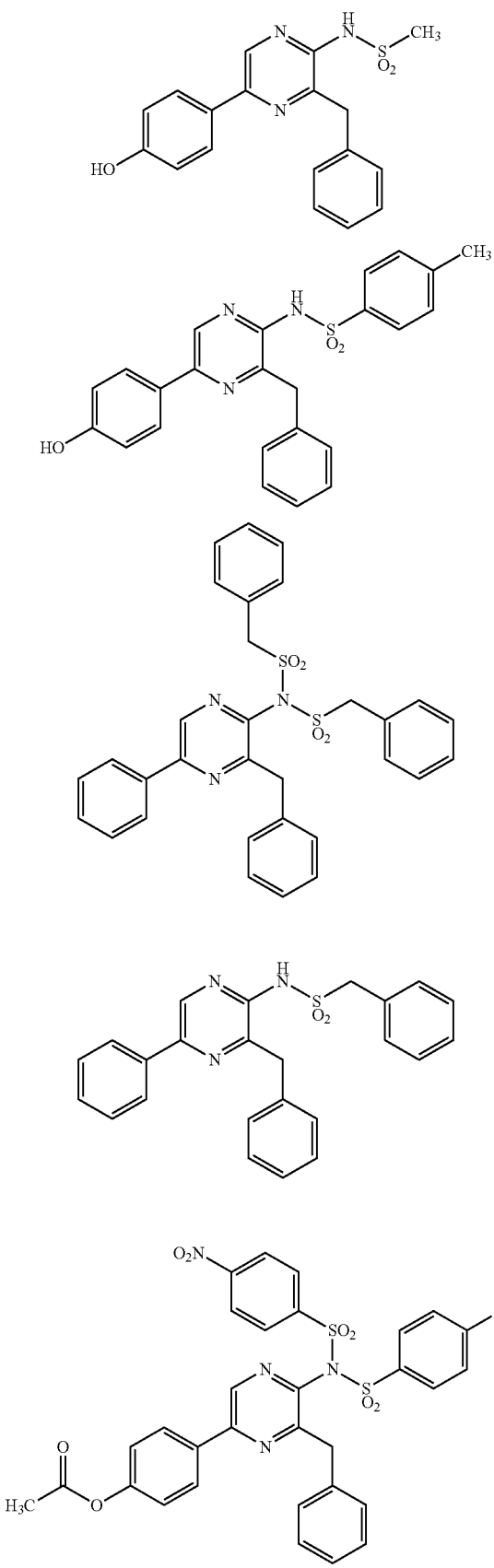
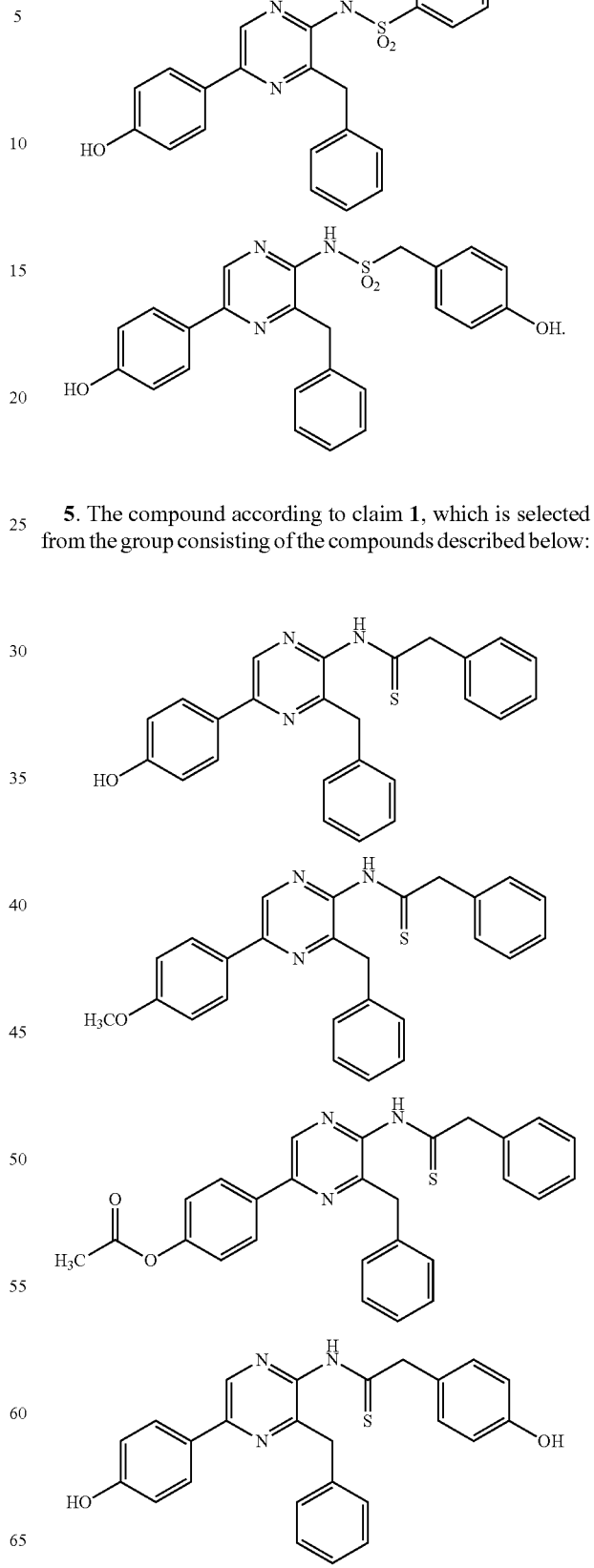
5. The compound according to claim 1, which is selected from the group consisting of the compounds described below:

-continued

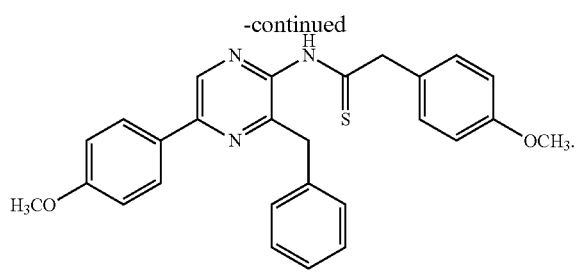

6. A blue fluorescent protein comprising the compound according to claim 1, the apoprotein of a calcium-binding photoprotein and a calcium ion or a divalent or trivalent ion substitutable for the calcium ion.

7. A process for producing a blue fluorescent protein, which comprises reacting the compound according to claim 1 with the apoprotein of a calcium-binding photoprotein in the presence of a calcium ion or a divalent or trivalent ion substitutable for a calcium ion.

8. The process according to claim 7, wherein the reaction is performed in the presence of a reducing agent.

9. A greenish fluorescent protein comprising the compound according to claim 1 and the apoprotein of a calcium-binding photoprotein.

10. A process for producing a greenish fluorescent protein, which comprises treating the blue fluorescent protein according to claim 6 with a chelating agent for removing a calcium ion or a divalent or trivalent ion substitutable for a calcium ion.

11. A process for producing a calcium-binding photoprotein, which comprises reacting the greenish fluorescent protein according to claim 9 with coelenterazine or an analog thereof.

12. The process according to claim 11, wherein the reaction of the fluorescent protein with coelenterazine or an analog thereof is performed in the presence of a reducing agent.

* * * * *